(12) United States Patent
Maimon et al.

(10) Patent No.: US 11,344,408 B2
(45) Date of Patent: May 31, 2022

(54) MECHANICALLY EXPANDING HEART VALVE AND DELIVERY APPARATUS THEREFOR

(71) Applicant: Edwards Lifesciences Corporation, Irvine, CA (US)

(72) Inventors: David Maimon, Atlit (IL); Boaz Manash, Givat Ada (IL); Eyal Leiba, N. Misgav (IL); Ziv Yohanan, Kfar Hahoresh (IL); Yair A. Neumann, Moshav Sede Varburg (IL); Anatoly Dvorsky, Haifa (IL); Jonathan Bar-Or, Jordan Valley (IL); Oren Cohen, Kadima (IL); Ofir Witzman, Kfar Saba (IL); Liron Tayeb, Peduel (IL); Elazar Levi Schwarcz, Netanya (IL); Noam Miller, Givatayim (IL); Tomer Saar, Pardes Hanna-Karkur (IL)

(73) Assignee: Edwards Lifesciences Corporation, Irvine, CA (US)

(*) Notice: Subject to any disclaimer, the term of this patent is extended or adjusted under 35 U.S.C. 154(b) by 269 days.

(21) Appl. No.: 16/813,637

(22) Filed: Mar. 9, 2020

(65) Prior Publication Data

US 2020/0297482 A1    Sep. 24, 2020

Related U.S. Application Data

(62) Division of application No. 15/831,197, filed on Dec. 4, 2017, now Pat. No. 10,603,165.
(Continued)

(51) Int. Cl.
*A61F 2/24* (2006.01)

(52) U.S. Cl.
CPC ............ *A61F 2/2418* (2013.01); *A61F 2/243* (2013.01); *A61F 2220/0041* (2013.01); *A61F 2250/001* (2013.01); *A61F 2250/0069* (2013.01)

(58) Field of Classification Search
CPC ........ A61F 2/24; A61F 2/2418; A61F 2/2427; A61F 2/243
See application file for complete search history.

(56) References Cited

U.S. PATENT DOCUMENTS 3,409,013 A    11/1968  Berry
3,548,417 A    12/1970  Kisher
(Continued)

FOREIGN PATENT DOCUMENTS

CN    1787793 A    6/2006
CN    105517509 A    4/2016
(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
(Continued)

*Primary Examiner* — Ryan J. Severson
(74) *Attorney, Agent, or Firm* — Klarquist Sparkman, LLP

(57) ABSTRACT

An assembly can comprise a radially expandable and compressible annular frame, at least one linear actuator assembly coupled to the frame and at least one locking mechanism coupled to the frame. The linear actuator can be configured to apply a distally directed force and/or a proximally directed force to the frame to radially expand or compress the frame. The locking mechanism can comprise a first
(Continued)

sleeve member connected to the frame at a first location, a second sleeve member having internal threads and being connected to the frame at a second location, and a first screw configured to engage the internal threads of the second sleeve member to retain the frame in a radially expanded state.

20 Claims, 40 Drawing Sheets

Related U.S. Application Data

(60) Provisional application No. 62/430,810, filed on Dec. 6, 2016.

(56) References Cited

U.S. PATENT DOCUMENTS

| | | | |
|---|---|---|---|
| 3,587,115 A | 6/1971 | Shiley | |
| 3,657,744 A | 4/1972 | Ersek | |
| 3,671,979 A | 6/1972 | Moulopoulos | |
| 3,714,671 A | 2/1973 | Edwards et al. | |
| 3,755,823 A | 9/1973 | Hancock | |
| 4,035,849 A | 7/1977 | Angell et al. | |
| 4,056,854 A | 11/1977 | Boretos et al. | |
| 4,106,129 A | 8/1978 | Carpentier et al. | |
| 4,222,126 A | 9/1980 | Boretos et al. | |
| 4,265,694 A | 5/1981 | Boretos et al. | |
| 4,297,749 A | 11/1981 | Davis et al. | |
| RE30,912 E | 4/1982 | Hancock | |
| 4,339,831 A | 7/1982 | Johnson | |
| 4,343,048 A | 8/1982 | Ross et al. | |
| 4,345,340 A | 8/1982 | Rosen | |
| 4,373,216 A | 2/1983 | Klawitter | |
| 4,406,022 A | 9/1983 | Roy | |
| 4,441,216 A | 4/1984 | Ionescu et al. | |
| 4,470,157 A | 9/1984 | Love | |
| 4,535,483 A | 8/1985 | Klawitter et al. | |
| 4,574,803 A | 3/1986 | Storz | |
| 4,592,340 A | 6/1986 | Boyles | |
| 4,605,407 A | 8/1986 | Black et al. | |
| 4,612,011 A | 9/1986 | Kautzky | |
| 4,643,732 A | 2/1987 | Pietsch et al. | |
| 4,655,771 A | 4/1987 | Wallsten | |
| 4,692,164 A | 9/1987 | Dzemeshkevich et al. | |
| 4,733,665 A | 3/1988 | Palmaz | |
| 4,759,758 A | 7/1988 | Gabbay | |
| 4,762,128 A | 8/1988 | Rosenbluth | |
| 4,777,951 A | 10/1988 | Cribier et al. | |
| 4,787,899 A | 11/1988 | Lazarus | |
| 4,787,901 A | 11/1988 | Baykut | |
| 4,796,629 A | 1/1989 | Grayzel | |
| 4,820,299 A | 4/1989 | Philippe et al. | |
| 4,829,990 A | 5/1989 | Thuroff et al. | |
| 4,851,001 A | 7/1989 | Taheri | |
| 4,856,516 A | 8/1989 | Hillstead | |
| 4,878,495 A | 11/1989 | Grayzel | |
| 4,878,906 A | 11/1989 | Lindemann et al. | |
| 4,883,458 A | 11/1989 | Shiber | |
| 4,922,905 A | 5/1990 | Strecker | |
| 4,966,604 A | 10/1990 | Reiss | |
| 4,979,939 A | 12/1990 | Shiber | |
| 4,986,830 A | 1/1991 | Owens et al. | |
| 4,994,077 A | 2/1991 | Dobben | |
| 5,007,896 A | 4/1991 | Shiber | |
| 5,026,366 A | 6/1991 | Leckrone | |
| 5,032,128 A | 7/1991 | Alonso | |
| 5,037,434 A | 8/1991 | Lane | |
| 5,047,041 A | 9/1991 | Samuels | |
| 5,059,177 A | 10/1991 | Towne et al. | |
| 5,080,668 A | 1/1992 | Bolz et al. | |
| 5,085,635 A | 2/1992 | Cragg | |
| 5,089,015 A | 2/1992 | Ross | |
| 5,152,771 A | 10/1992 | Sabbaghian et al. | |
| 5,163,953 A | 11/1992 | Vince | |
| 5,167,628 A | 12/1992 | Boyles | |
| 5,192,297 A | 3/1993 | Hull | |
| 5,266,073 A | 11/1993 | Wall | |
| 5,282,847 A | 2/1994 | Trescony et al. | |
| 5,295,958 A | 3/1994 | Shturman | |
| 5,332,402 A | 7/1994 | Teitelbaum | |
| 5,360,444 A | 11/1994 | Kusuhara | |
| 5,370,685 A | 12/1994 | Stevens | |
| 5,397,351 A | 3/1995 | Pavcnik et al. | |
| 5,411,055 A | 5/1995 | Kane | |
| 5,411,552 A | 5/1995 | Andersen et al. | |
| 5,443,446 A | 8/1995 | Shturman | |
| 5,480,424 A | 1/1996 | Cox | |
| 5,500,014 A | 3/1996 | Quijano et al. | |
| 5,545,209 A | 8/1996 | Roberts et al. | |
| 5,545,214 A | 8/1996 | Stevens | |
| 5,549,665 A | 8/1996 | Vesely et al. | |
| 5,554,185 A | 9/1996 | Block et al. | |
| 5,558,644 A | 9/1996 | Boyd et al. | |
| 5,571,175 A | 11/1996 | Vanney et al. | |
| 5,584,803 A | 12/1996 | Stevens et al. | |
| 5,591,185 A | 1/1997 | Kilmer et al. | |
| 5,591,195 A | 1/1997 | Taheri et al. | |
| 5,607,464 A | 3/1997 | Trescony et al. | |
| 5,609,626 A | 3/1997 | Quijano et al. | |
| 5,628,792 A | 5/1997 | Lentell | |
| 5,639,274 A | 6/1997 | Fischell et al. | |
| 5,665,115 A | 9/1997 | Cragg | |
| 5,716,417 A | 2/1998 | Girard et al. | |
| 5,728,068 A | 3/1998 | Leone et al. | |
| 5,749,890 A | 5/1998 | Shaknovich | |
| 5,756,476 A | 5/1998 | Epstein et al. | |
| 5,769,812 A | 6/1998 | Stevens et al. | |
| 5,800,508 A | 9/1998 | Goicoechea et al. | |
| 5,840,081 A | 11/1998 | Andersen et al. | |
| 5,855,565 A * | 1/1999 | Bar-Cohen | A61M 29/02 604/104 |
| 5,855,597 A | 1/1999 | Jayaraman | |
| 5,855,601 A | 1/1999 | Bessler et al. | |
| 5,855,602 A | 1/1999 | Angell | |
| 5,925,063 A | 7/1999 | Khosravi | |
| 5,957,949 A | 9/1999 | Leonhardt et al. | |
| 6,027,525 A | 2/2000 | Suh et al. | |
| 6,132,473 A | 10/2000 | Williams et al. | |
| 6,168,614 B1 | 1/2001 | Andersen et al. | |
| 6,171,335 B1 | 1/2001 | Wheatley et al. | |
| 6,174,327 B1 | 1/2001 | Mertens et al. | |
| 6,210,408 B1 | 4/2001 | Chandrasekaran et al. | |
| 6,217,585 B1 | 4/2001 | Houser et al. | |
| 6,221,091 B1 | 4/2001 | Khosravi | |
| 6,231,602 B1 | 5/2001 | Carpentier et al. | |
| 6,245,102 B1 | 6/2001 | Jayaraman | |
| 6,299,637 B1 | 10/2001 | Shaolian et al. | |
| 6,302,906 B1 | 10/2001 | Goicoechea et al. | |
| 6,338,740 B1 | 1/2002 | Carpentier | |
| 6,350,277 B1 | 2/2002 | Kocur | |
| 6,352,547 B1 | 3/2002 | Brown et al. | |
| 6,425,916 B1 | 7/2002 | Garrison et al. | |
| 6,440,764 B1 | 8/2002 | Focht et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,468,660 B2 | 10/2002 | Ogle et al. | |
| 6,482,228 B1 | 11/2002 | Norred | |
| 6,488,704 B1 | 12/2002 | Connelly et al. | |
| 6,527,979 B2 | 3/2003 | Constantz et al. | |
| 6,569,196 B1 | 5/2003 | Vesely | |
| 6,582,462 B1 | 6/2003 | Andersen et al. | |
| 6,605,112 B1 | 8/2003 | Moll et al. | |
| 6,652,578 B2 | 11/2003 | Bailey et al. | |
| 6,689,123 B2 | 2/2004 | Pinchasik | |
| 6,716,230 B2 * | 4/2004 | Whitman | A61M 29/02 606/198 |
| 6,716,244 B2 | 4/2004 | Klaco | |
| 6,730,118 B2 | 5/2004 | Spenser et al. | |
| 6,733,525 B2 | 5/2004 | Yang et al. | |
| 6,767,362 B2 | 7/2004 | Schreck | |
| 6,769,161 B2 | 8/2004 | Brown et al. | |

(56) References Cited

U.S. PATENT DOCUMENTS

| | | | |
|---|---|---|---|
| 6,783,542 B2 | 8/2004 | Eidenschink | |
| 6,830,584 B1 | 12/2004 | Seguin | |
| 6,878,162 B2 | 4/2005 | Bales et al. | |
| 6,893,460 B2 | 5/2005 | Spenser et al. | |
| 6,908,481 B2 | 6/2005 | Cribier | |
| 6,936,067 B2 | 8/2005 | Buchanan | |
| 7,011,681 B2 * | 3/2006 | Vesely | A61F 2/2409 623/1.11 |
| 7,018,406 B2 | 3/2006 | Seguin et al. | |
| 7,018,408 B2 | 3/2006 | Bailey et al. | |
| 7,096,554 B2 | 8/2006 | Austin et al. | |
| 7,097,658 B2 * | 8/2006 | Oktay | A61F 2/82 623/1.15 |
| 7,141,063 B2 * | 11/2006 | White | A61F 2/844 623/1.15 |
| 7,225,518 B2 | 6/2007 | Eidenschink et al. | |
| 7,276,078 B2 | 10/2007 | Spenser et al. | |
| 7,276,084 B2 | 10/2007 | Yang et al. | |
| 7,316,710 B1 | 1/2008 | Cheng et al. | |
| 7,318,278 B2 | 1/2008 | Zhang et al. | |
| 7,374,571 B2 | 5/2008 | Pease et al. | |
| 7,381,219 B2 * | 6/2008 | Salahieh | A61F 2/2418 623/2.11 |
| 7,393,360 B2 | 7/2008 | Spenser et al. | |
| 7,462,191 B2 | 12/2008 | Spenser et al. | |
| 7,510,575 B2 | 3/2009 | Spenser et al. | |
| 7,556,646 B2 * | 7/2009 | Yang | A61F 2/243 623/2.11 |
| 7,563,280 B2 | 7/2009 | Anderson et al. | |
| 7,585,321 B2 | 9/2009 | Cribier | |
| 7,618,446 B2 | 11/2009 | Andersen et al. | |
| 7,618,447 B2 | 11/2009 | Case et al. | |
| 7,655,034 B2 | 2/2010 | Mitchell et al. | |
| 7,785,341 B2 * | 8/2010 | Forster | A61F 2/2427 606/194 |
| 7,785,366 B2 | 8/2010 | Maurer et al. | |
| 7,959,665 B2 | 6/2011 | Pienknagura | |
| 7,959,672 B2 | 6/2011 | Salahieh et al. | |
| 7,988,724 B2 * | 8/2011 | Salahieh | A61F 2/2418 623/2.12 |
| 7,993,394 B2 | 8/2011 | Hariton et al. | |
| 8,029,556 B2 | 10/2011 | Rowe | |
| 8,075,611 B2 | 12/2011 | Millwee et al. | |
| 8,128,686 B2 | 3/2012 | Paul, Jr. et al. | |
| 8,167,932 B2 | 5/2012 | Bourang et al. | |
| 8,226,707 B2 * | 7/2012 | White | A61F 2/2409 623/1.24 |
| 8,291,570 B2 | 10/2012 | Eidenschink et al. | |
| 8,348,998 B2 | 1/2013 | Pintor et al. | |
| 8,430,925 B2 * | 4/2013 | Forster | A61F 2/2427 623/1.26 |
| 8,449,606 B2 | 5/2013 | Eliasen et al. | |
| 8,454,685 B2 | 6/2013 | Hariton et al. | |
| 8,647,378 B2 * | 2/2014 | Mews | A61B 17/8858 623/1.15 |
| 8,652,202 B2 * | 2/2014 | Alon | A61F 2/2418 623/2.11 |
| 8,652,203 B2 | 2/2014 | Quadri et al. | |
| 8,685,080 B2 * | 4/2014 | White | A61F 2/2418 623/1.26 |
| 8,747,463 B2 | 6/2014 | Fogarty et al. | |
| 9,039,756 B2 * | 5/2015 | White | A61F 2/844 623/1.24 |
| 9,078,781 B2 | 7/2015 | Ryan et al. | |
| 9,301,860 B2 * | 4/2016 | White | A61F 2/844 |
| 9,358,110 B2 * | 6/2016 | Paul | A61F 2/2427 |
| 9,387,076 B2 * | 7/2016 | Paul | A61F 2/90 |
| 9,566,178 B2 * | 2/2017 | Cartledge | A61F 2/2436 |
| 9,700,442 B2 * | 7/2017 | White | A61F 2/24 |
| 9,814,611 B2 * | 11/2017 | Cartledge | A61F 2/93 |
| 9,827,093 B2 * | 11/2017 | Cartledge | A61B 5/6862 |
| 10,603,165 B2 * | 3/2020 | Maimon | A61F 2/2418 |
| 10,869,759 B2 * | 12/2020 | Barash | A61F 2/2418 |
| 10,874,508 B2 * | 12/2020 | Cartledge | A61F 2/95 |
| 10,973,629 B2 * | 4/2021 | Levi | A61F 2/2418 |
| 11,013,595 B2 * | 5/2021 | Levi | A61F 2/2418 |
| 11,026,785 B2 * | 6/2021 | Barash | A61F 2/2418 |
| 2001/0021872 A1 | 9/2001 | Bailey et al. | |
| 2002/0026094 A1 | 2/2002 | Roth | |
| 2002/0032481 A1 | 3/2002 | Gabbay | |
| 2002/0138135 A1 | 9/2002 | Duerig et al. | |
| 2002/0143390 A1 | 10/2002 | Ishii | |
| 2002/0173842 A1 | 11/2002 | Buchanan | |
| 2003/0014105 A1 | 1/2003 | Cao | |
| 2003/0050694 A1 | 3/2003 | Yang et al. | |
| 2003/0100939 A1 | 5/2003 | Yodfat et al. | |
| 2003/0158597 A1 | 8/2003 | Quiachon et al. | |
| 2003/0212454 A1 | 11/2003 | Scott et al. | |
| 2004/0024452 A1 | 2/2004 | Kruse et al. | |
| 2004/0039436 A1 | 2/2004 | Spenser et al. | |
| 2004/0078074 A1 | 4/2004 | Anderson et al. | |
| 2004/0186558 A1 | 9/2004 | Pavcnik et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0010285 A1 | 1/2005 | Lambrecht et al. | |
| 2005/0075725 A1 | 4/2005 | Rowe | |
| 2005/0075728 A1 | 4/2005 | Nguyen et al. | |
| 2005/0096736 A1 | 5/2005 | Osse et al. | |
| 2005/0096738 A1 | 5/2005 | Cali et al. | |
| 2005/0188525 A1 | 9/2005 | Weber et al. | |
| 2005/0203614 A1 | 9/2005 | Forster et al. | |
| 2005/0203617 A1 | 9/2005 | Forster et al. | |
| 2005/0234546 A1 | 10/2005 | Nugent et al. | |
| 2006/0004469 A1 | 1/2006 | Sokel | |
| 2006/0025857 A1 | 2/2006 | Bergheim et al. | |
| 2006/0058872 A1 | 3/2006 | Salahieh et al. | |
| 2006/0074484 A1 | 4/2006 | Huber | |
| 2006/0108090 A1 | 5/2006 | Ederer et al. | |
| 2006/0149350 A1 | 7/2006 | Patel et al. | |
| 2006/0183383 A1 | 8/2006 | Asmus et al. | |
| 2006/0217794 A1 * | 9/2006 | Ruiz | A61F 2/2418 623/1.11 |
| 2006/0229719 A1 | 10/2006 | Marquez et al. | |
| 2006/0259136 A1 | 11/2006 | Nguyen et al. | |
| 2006/0259137 A1 | 11/2006 | Artof et al. | |
| 2006/0287717 A1 | 12/2006 | Rowe et al. | |
| 2007/0005131 A1 | 1/2007 | Taylor | |
| 2007/0010876 A1 | 1/2007 | Salahieh et al. | |
| 2007/0010877 A1 | 1/2007 | Salahieh et al. | |
| 2007/0112422 A1 | 5/2007 | Dehdashtian | |
| 2007/0162102 A1 | 7/2007 | Ryan et al. | |
| 2007/0203503 A1 | 8/2007 | Salahieh et al. | |
| 2007/0203575 A1 | 8/2007 | Forster et al. | |
| 2007/0203576 A1 | 8/2007 | Lee et al. | |
| 2007/0208550 A1 | 9/2007 | Cao et al. | |
| 2007/0213813 A1 | 9/2007 | Von Segesser et al. | |
| 2007/0233228 A1 | 10/2007 | Eberhardt et al. | |
| 2007/0260305 A1 | 11/2007 | Drews et al. | |
| 2007/0265700 A1 | 11/2007 | Eliasen et al. | |
| 2008/0021546 A1 | 1/2008 | Patz et al. | |
| 2008/0114442 A1 | 5/2008 | Mitchell et al. | |
| 2008/0125853 A1 | 5/2008 | Bailey et al. | |
| 2008/0154355 A1 | 6/2008 | Benichou et al. | |
| 2008/0183271 A1 | 7/2008 | Frawley et al. | |
| 2008/0208327 A1 | 8/2008 | Rowe | |
| 2008/0243245 A1 | 10/2008 | Thambar et al. | |
| 2008/0255660 A1 | 10/2008 | Guyenot et al. | |
| 2008/0275537 A1 | 11/2008 | Limon | |
| 2008/0294248 A1 | 11/2008 | Yang et al. | |
| 2009/0118826 A1 | 5/2009 | Khaghani | |
| 2009/0125118 A1 | 5/2009 | Gong | |
| 2009/0157175 A1 | 6/2009 | Benichou | |
| 2009/0276040 A1 | 11/2009 | Rowe et al. | |
| 2009/0281619 A1 | 11/2009 | Le et al. | |
| 2009/0287296 A1 | 11/2009 | Manasse | |
| 2009/0287299 A1 | 11/2009 | Tabor et al. | |
| 2009/0299452 A1 | 12/2009 | Eidenschink et al. | |
| 2009/0319037 A1 | 12/2009 | Rowe et al. | |
| 2010/0049313 A1 | 2/2010 | Alon et al. | |
| 2010/0082094 A1 | 4/2010 | Quadri et al. | |
| 2010/0168844 A1 | 7/2010 | Toomes et al. | |
| 2010/0185277 A1 | 7/2010 | Braido et al. | |

(56) References Cited

U.S. PATENT DOCUMENTS

| | | | |
|---|---|---|---|
| 2010/0198347 A1 | 8/2010 | Zakay et al. | |
| 2010/0204781 A1 | 8/2010 | Alkhatib | |
| 2011/0004299 A1 | 1/2011 | Essinger et al. | |
| 2011/0015729 A1 | 1/2011 | Jimenez et al. | |
| 2011/0066224 A1 | 3/2011 | White | |
| 2011/0066244 A1 | 3/2011 | Frasier et al. | |
| 2011/0137397 A1 | 6/2011 | Chau et al. | |
| 2011/0218619 A1 | 9/2011 | Benichou et al. | |
| 2011/0288632 A1* | 11/2011 | White | A61F 2/24 623/1.16 |
| 2011/0319991 A1 | 12/2011 | Hariton et al. | |
| 2012/0089223 A1 | 4/2012 | Nguyen et al. | |
| 2012/0101571 A1 | 4/2012 | Thambar et al. | |
| 2012/0123529 A1 | 5/2012 | Levi et al. | |
| 2012/0150289 A1* | 6/2012 | Forster | A61F 2/243 623/2.11 |
| 2012/0259409 A1 | 10/2012 | Nguyen et al. | |
| 2013/0023985 A1 | 1/2013 | Khairkhahan et al. | |
| 2013/0046373 A1 | 2/2013 | Cartledge et al. | |
| 2013/0150956 A1 | 6/2013 | Yohanan et al. | |
| 2013/0166017 A1 | 6/2013 | Cartledge et al. | |
| 2013/0190857 A1 | 7/2013 | Mitra et al. | |
| 2013/0274873 A1 | 10/2013 | Delaloye et al. | |
| 2013/0310926 A1 | 11/2013 | Hariton | |
| 2013/0317598 A1 | 11/2013 | Rowe et al. | |
| 2013/0331929 A1 | 12/2013 | Mitra et al. | |
| 2014/0194981 A1 | 7/2014 | Menk et al. | |
| 2014/0200661 A1 | 7/2014 | Pintor et al. | |
| 2014/0209238 A1 | 7/2014 | Bonyuet et al. | |
| 2014/0222136 A1 | 8/2014 | Geist et al. | |
| 2014/0277417 A1 | 9/2014 | Schraut et al. | |
| 2014/0277419 A1 | 9/2014 | Garde et al. | |
| 2014/0277424 A1 | 9/2014 | Oslund | |
| 2014/0277563 A1 | 9/2014 | White | |
| 2014/0296962 A1 | 10/2014 | Cartledge et al. | |
| 2014/0330372 A1 | 11/2014 | Weston et al. | |
| 2014/0343670 A1 | 11/2014 | Bakis et al. | |
| 2014/0343671 A1 | 11/2014 | Yohanan et al. | |
| 2014/0350667 A1 | 11/2014 | Braido et al. | |
| 2015/0073545 A1 | 3/2015 | Braido | |
| 2015/0073546 A1 | 3/2015 | Braido | |
| 2015/0135506 A1 | 5/2015 | White | |
| 2015/0157455 A1 | 6/2015 | Hoang et al. | |
| 2015/0209142 A1* | 7/2015 | Paul | A61F 2/2427 623/2.11 |
| 2017/0014229 A1 | 1/2017 | Nguyen-Thien-Nhon et al. | |
| 2018/0028310 A1 | 2/2018 | Gurovich et al. | |
| 2018/0153689 A1 | 6/2018 | Maimon et al. | |
| 2018/0325665 A1 | 11/2018 | Gurovich et al. | |
| 2018/0344456 A1 | 12/2018 | Barash et al. | |
| 2020/0297482 A1* | 9/2020 | Maimon | A61F 2/2418 |

FOREIGN PATENT DOCUMENTS

| | | |
|---|---|---|
| DE | 0144167 C | 9/1903 |
| DE | 2246526 A1 | 3/1973 |
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0850607 A1 | 7/1998 |
| EP | 1057460 A1 | 12/2000 |
| EP | 1088529 A2 | 4/2001 |
| EP | 1570809 A1 | 9/2005 |
| EP | 2438872 A1 | 4/2012 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9930646 A1 | 6/1999 |
| WO | 9933414 A1 | 7/1999 |
| WO | 0018333 A1 | 4/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0047139 A9 | 9/2001 |
| WO | 0164137 A1 | 9/2001 |
| WO | 0176510 A2 | 10/2001 |
| WO | 0222054 A1 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 03047468 A1 | 6/2003 |
| WO | 2005034812 | 4/2005 |
| WO | 2005055883 A1 | 6/2005 |
| WO | 2005084595 A1 | 9/2005 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008079962 A1 | 7/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009042196 A2 | 4/2009 |
| WO | 2009053497 A1 | 4/2009 |
| WO | 2009061389 A2 | 5/2009 |
| WO | 2009116041 | 9/2009 |
| WO | 2009149462 A2 | 12/2009 |
| WO | 2010011699 A2 | 1/2010 |
| WO | 2010121076 A2 | 10/2010 |
| WO | 2013106585 A1 | 7/2013 |
| WO | 2015085218 A1 | 6/2015 |
| WO | 2018106837 A1 | 6/2018 |
| WO | 2019040571 A1 | 2/2019 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

(56) References Cited

OTHER PUBLICATIONS

Uchida, "Modifications of Gianturco Expandable Wire Stents," American Journal of Roentgenology, vol. 150. pp. 1185-1187. 1986.

* cited by examiner

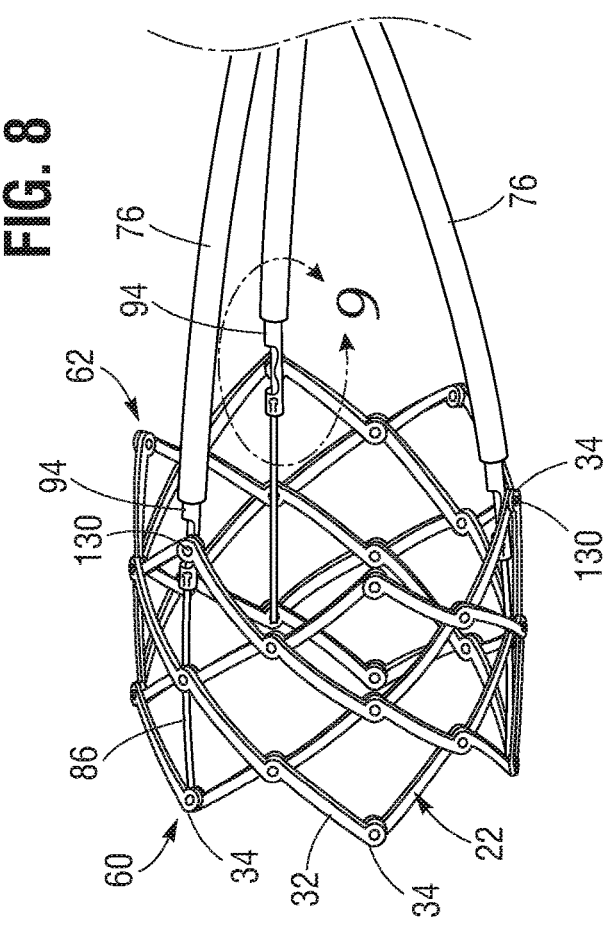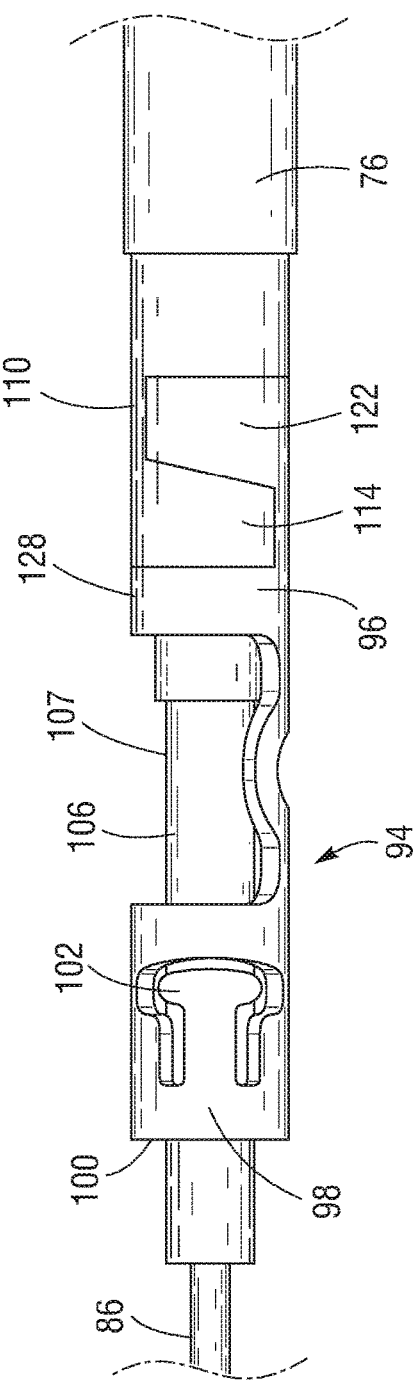

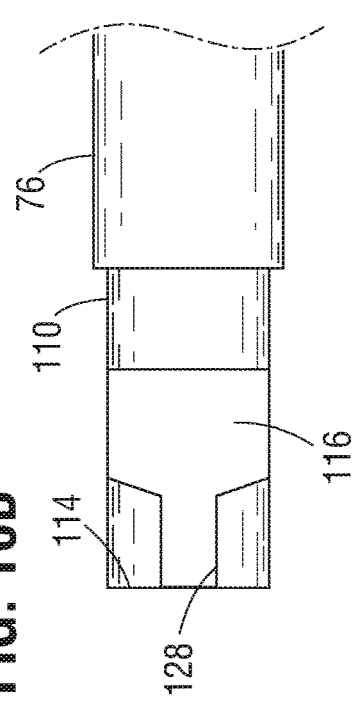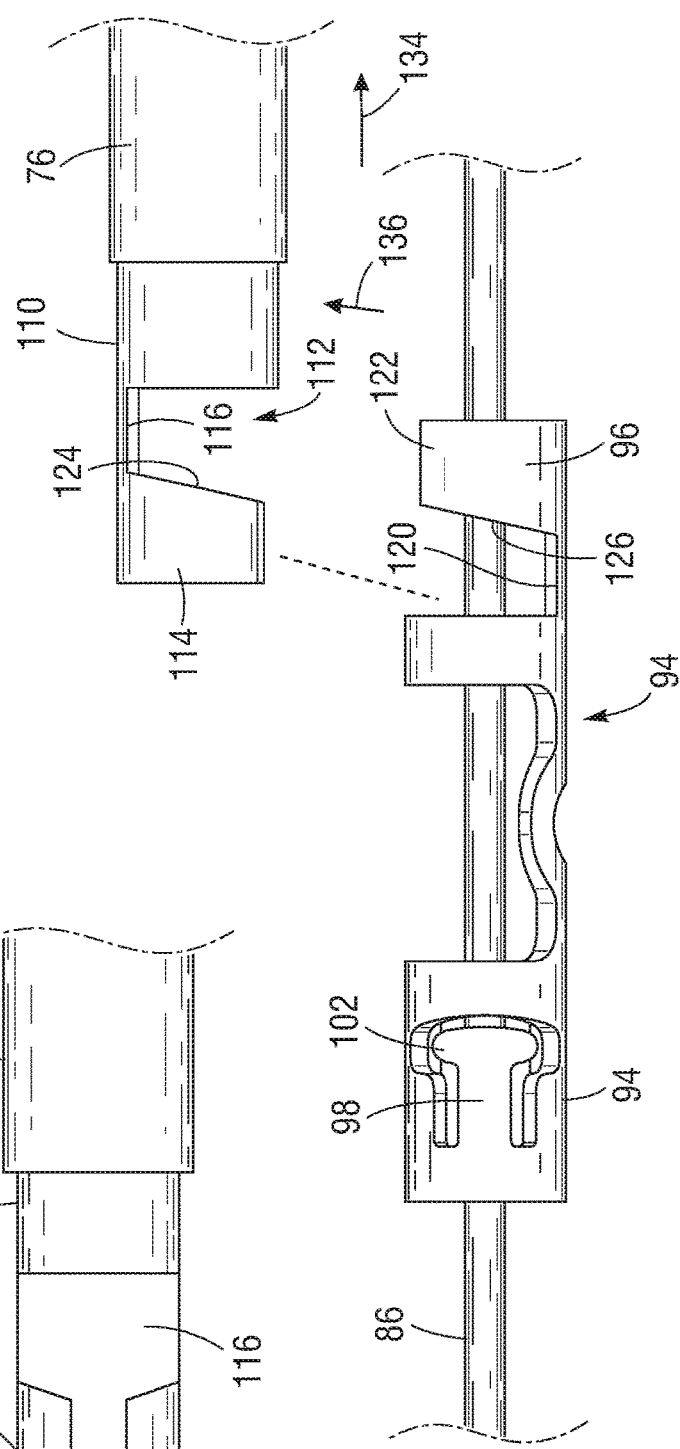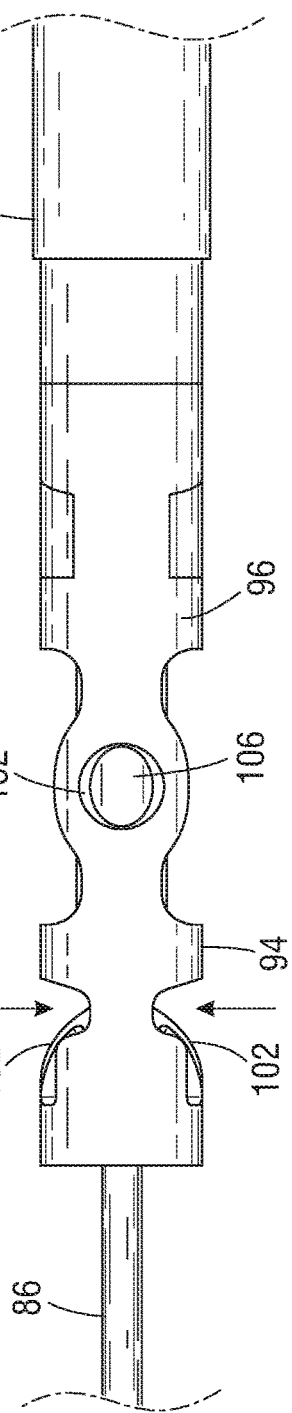

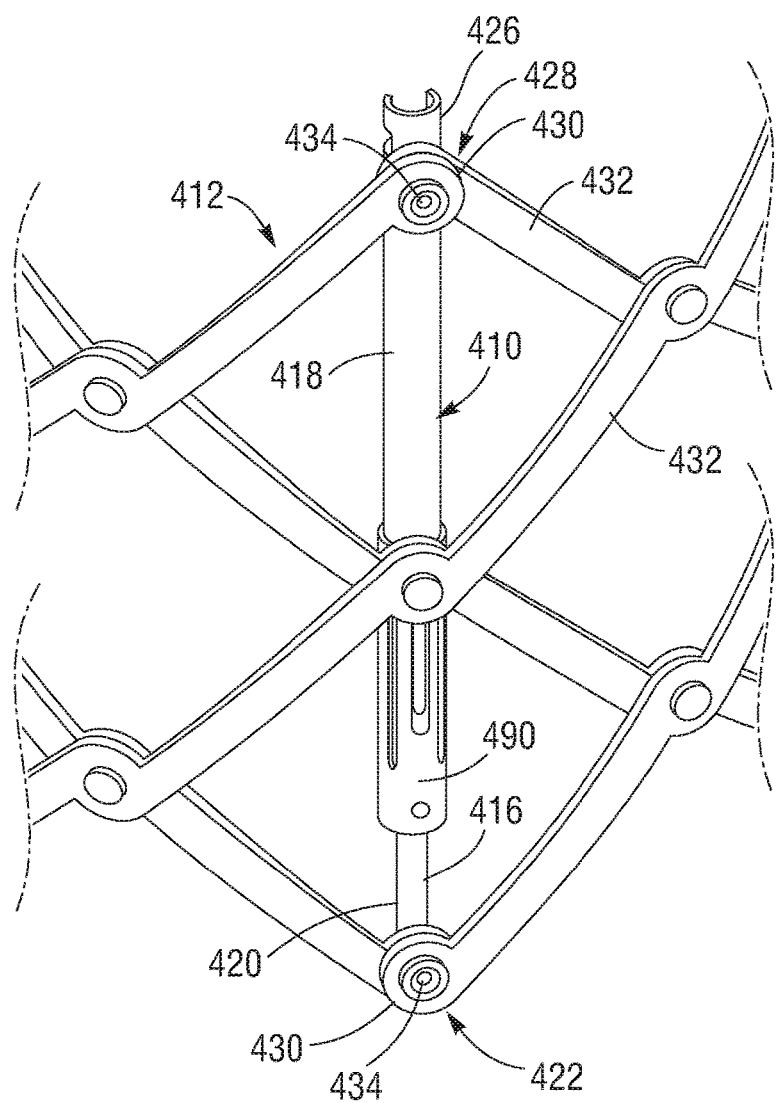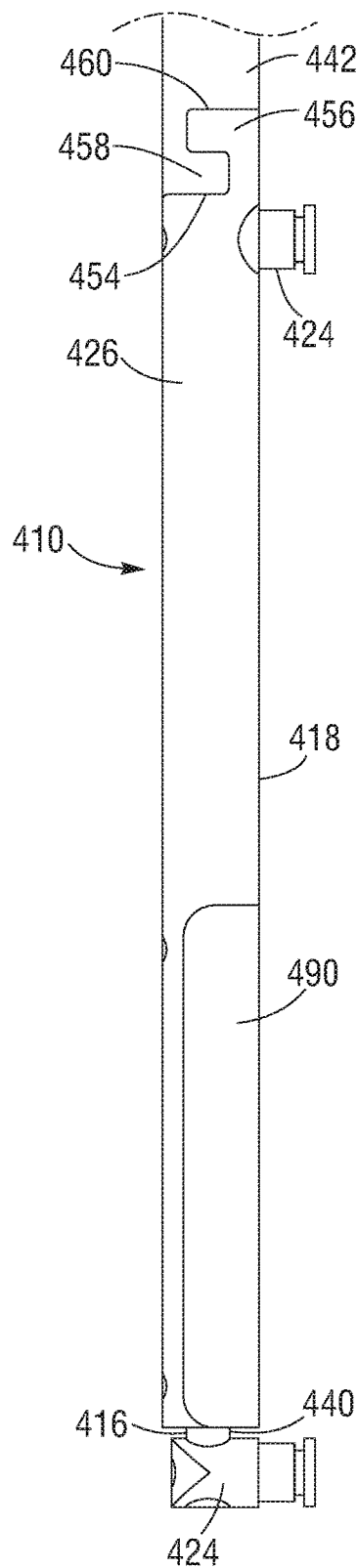

FIG. 16A
FIG. 16B
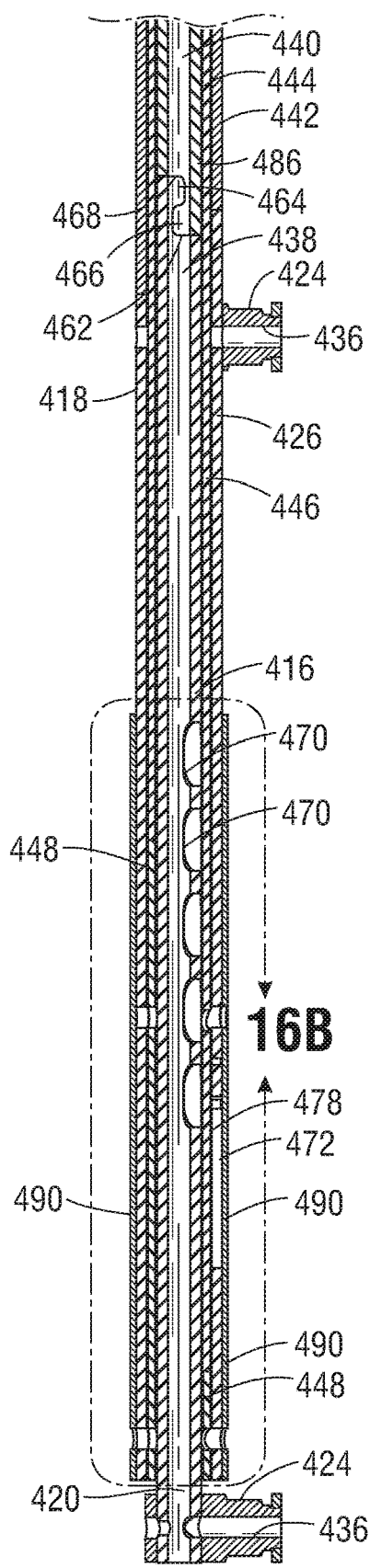
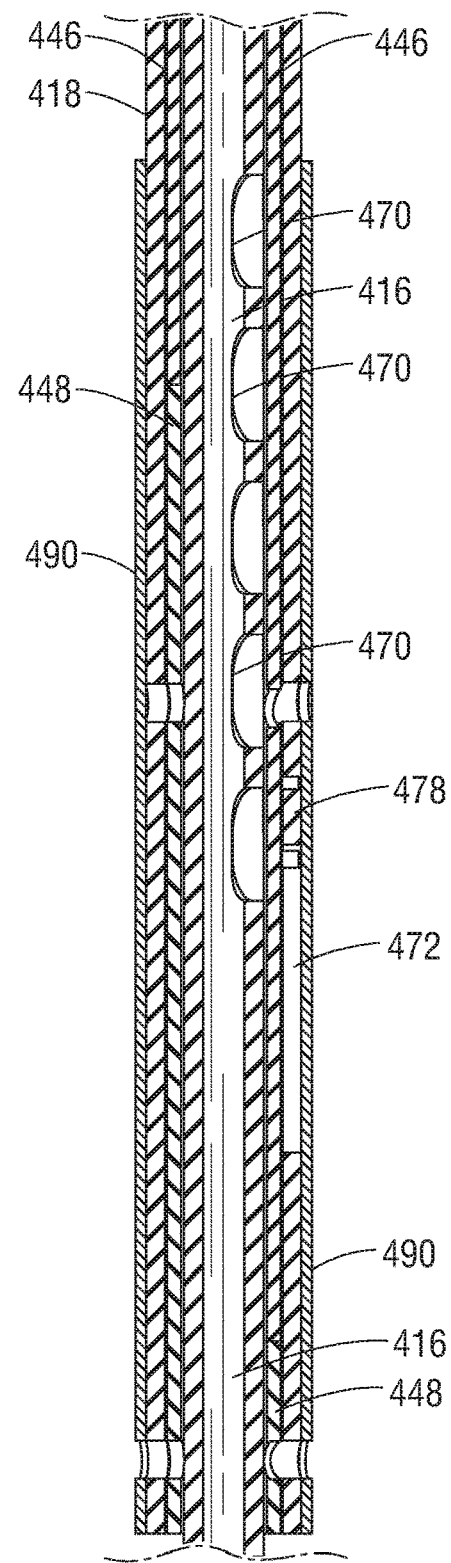

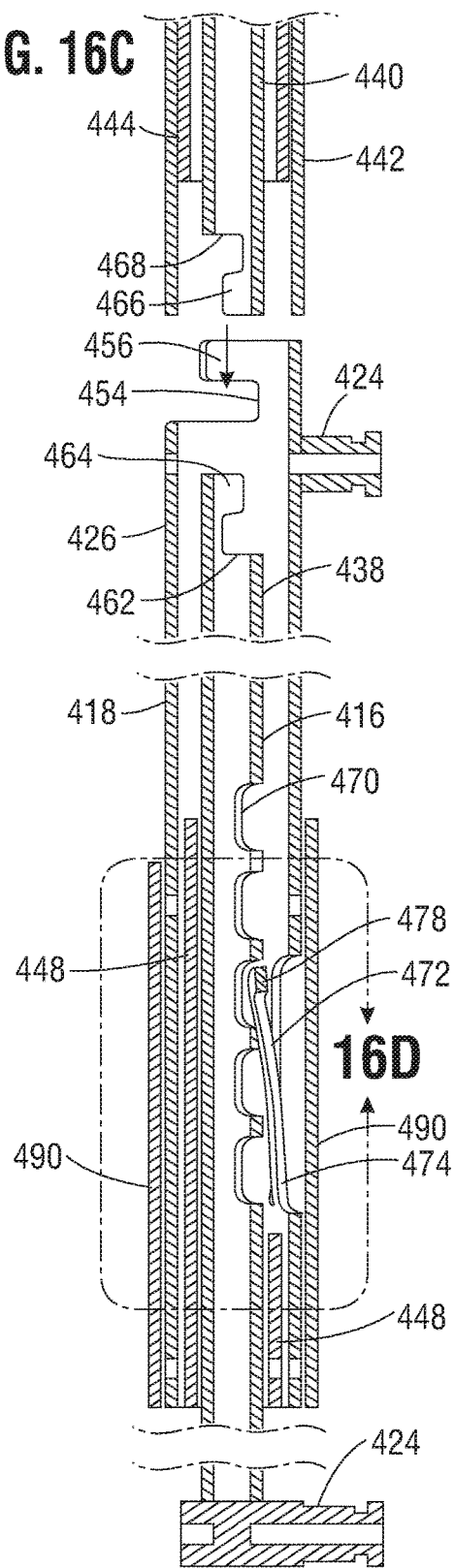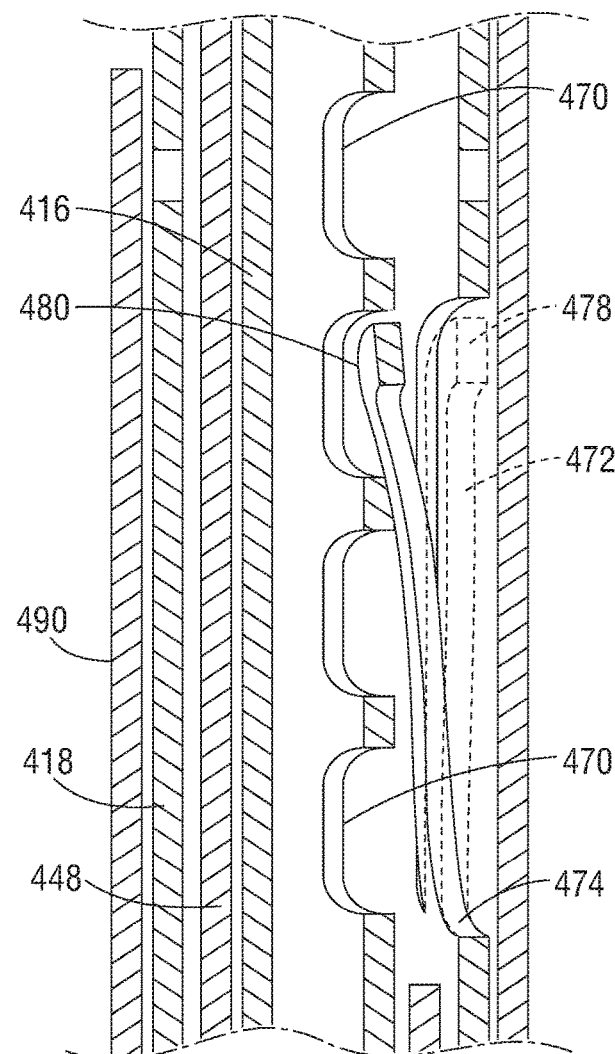

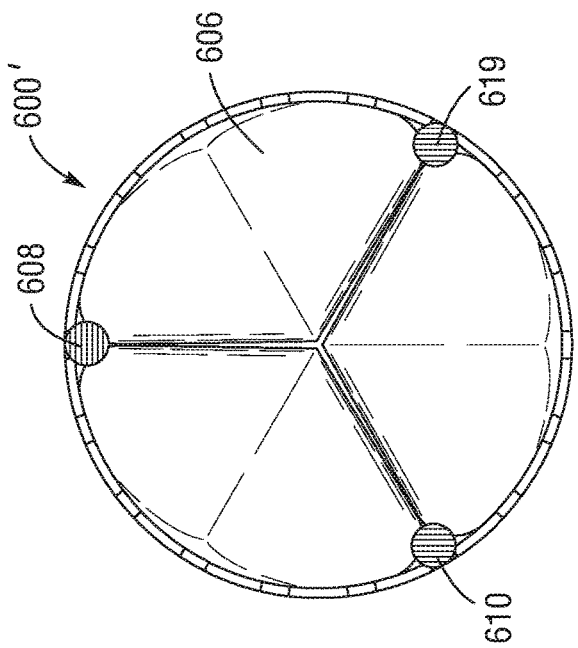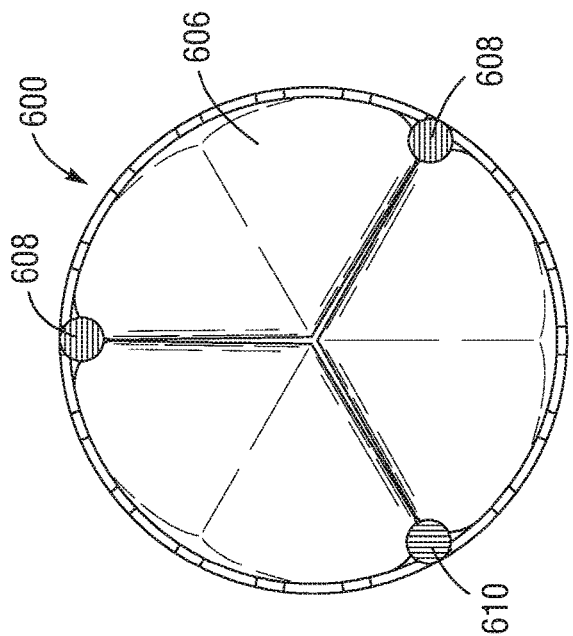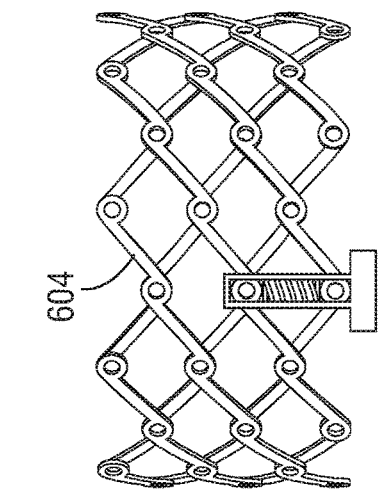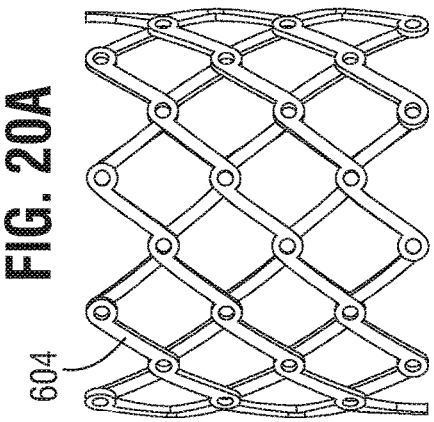

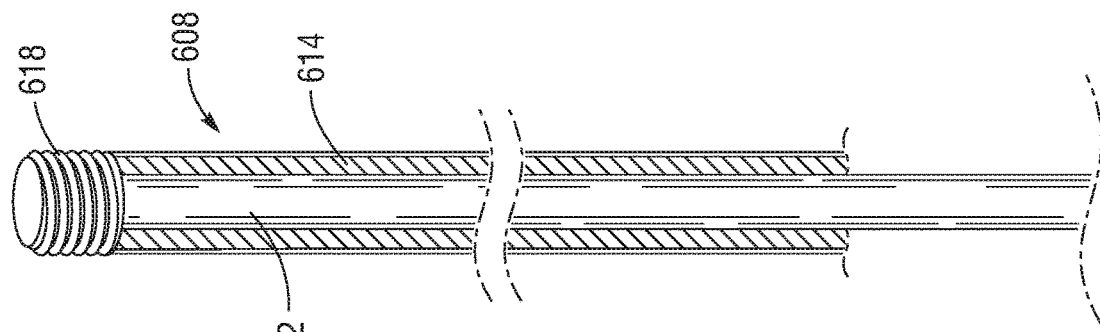
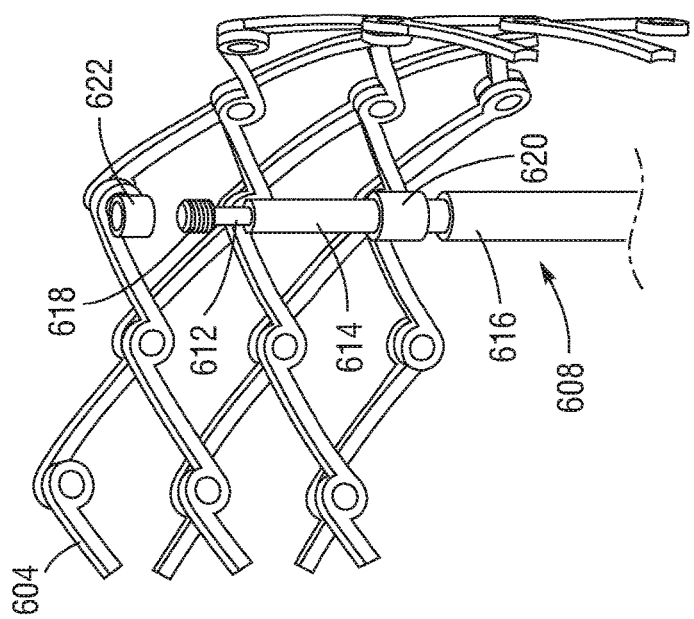

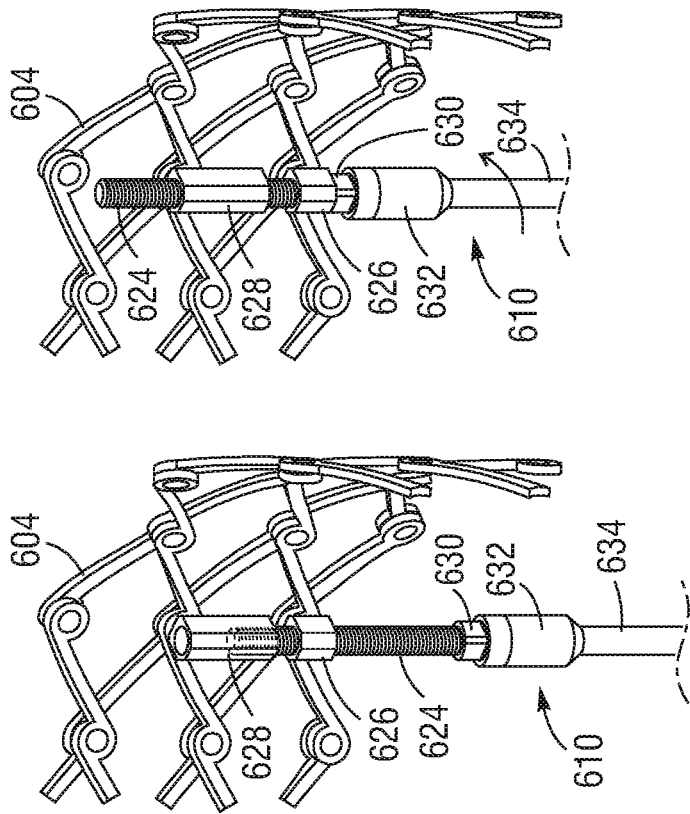

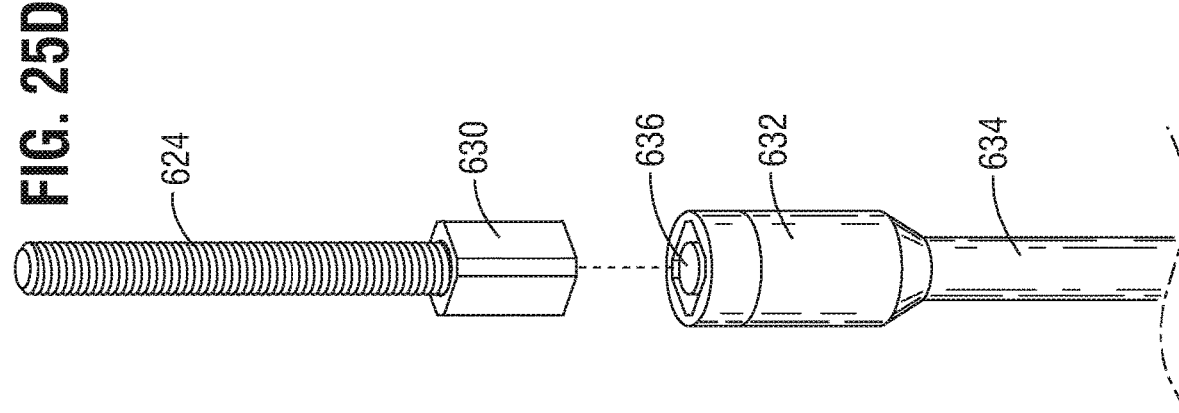
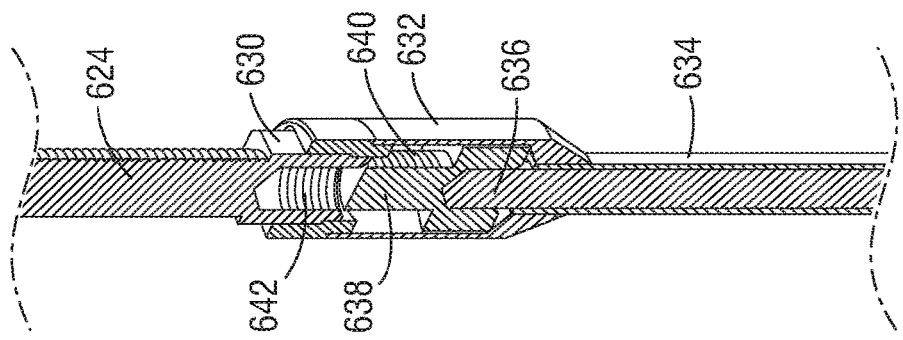
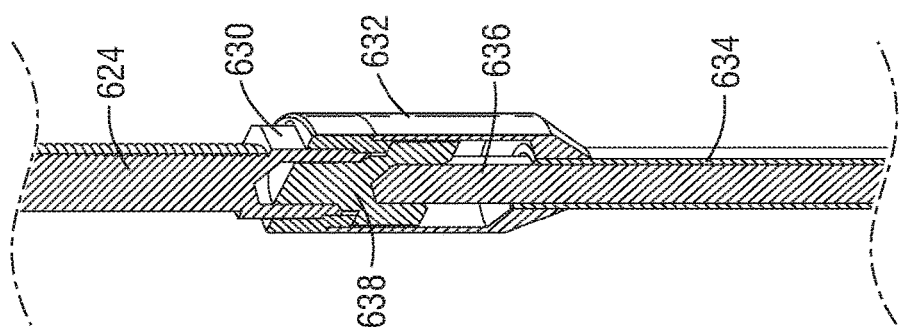
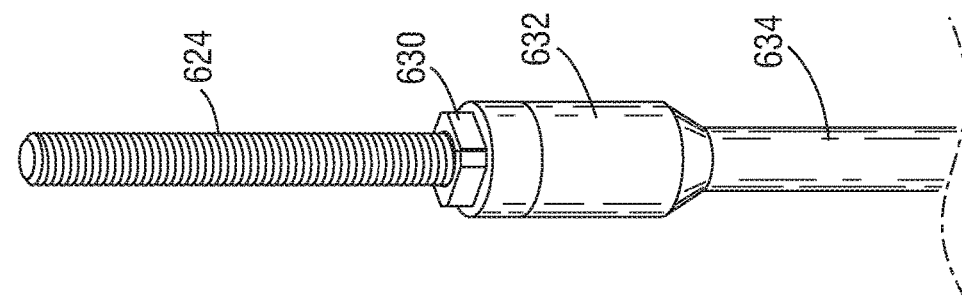

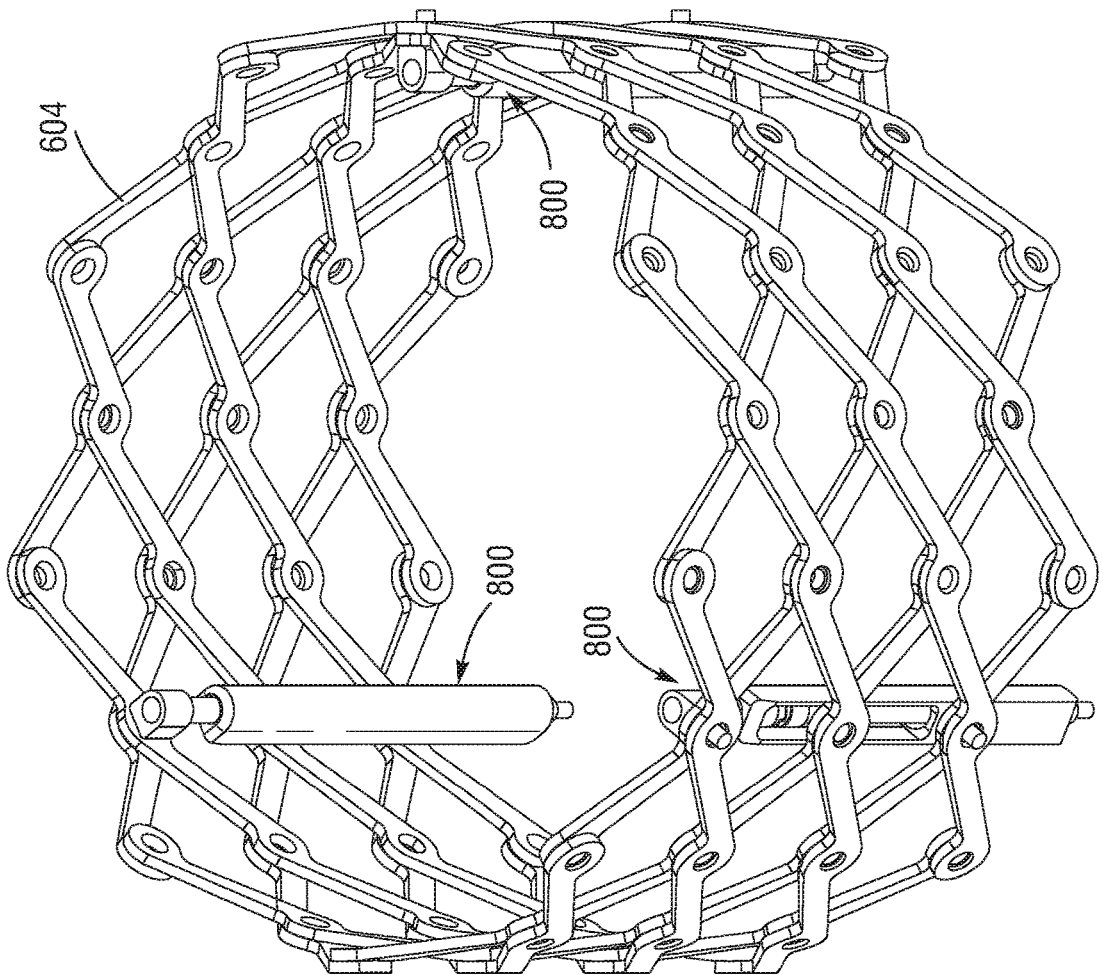
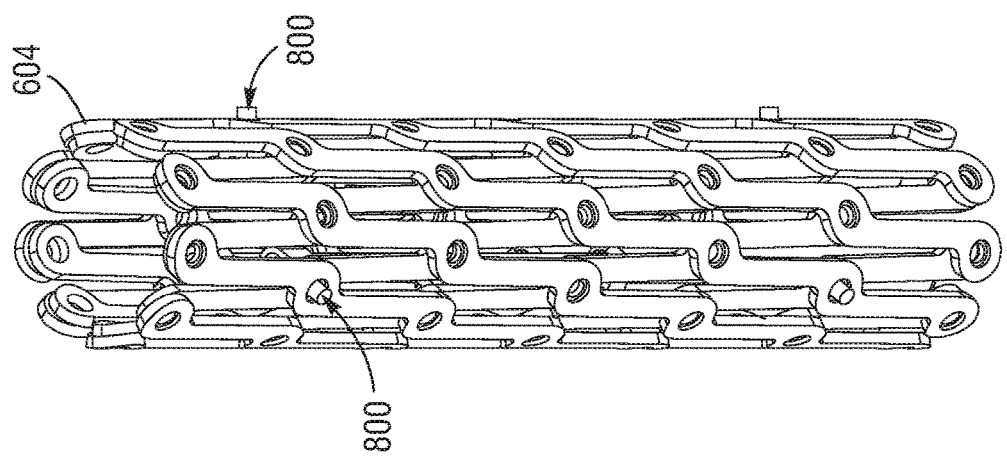

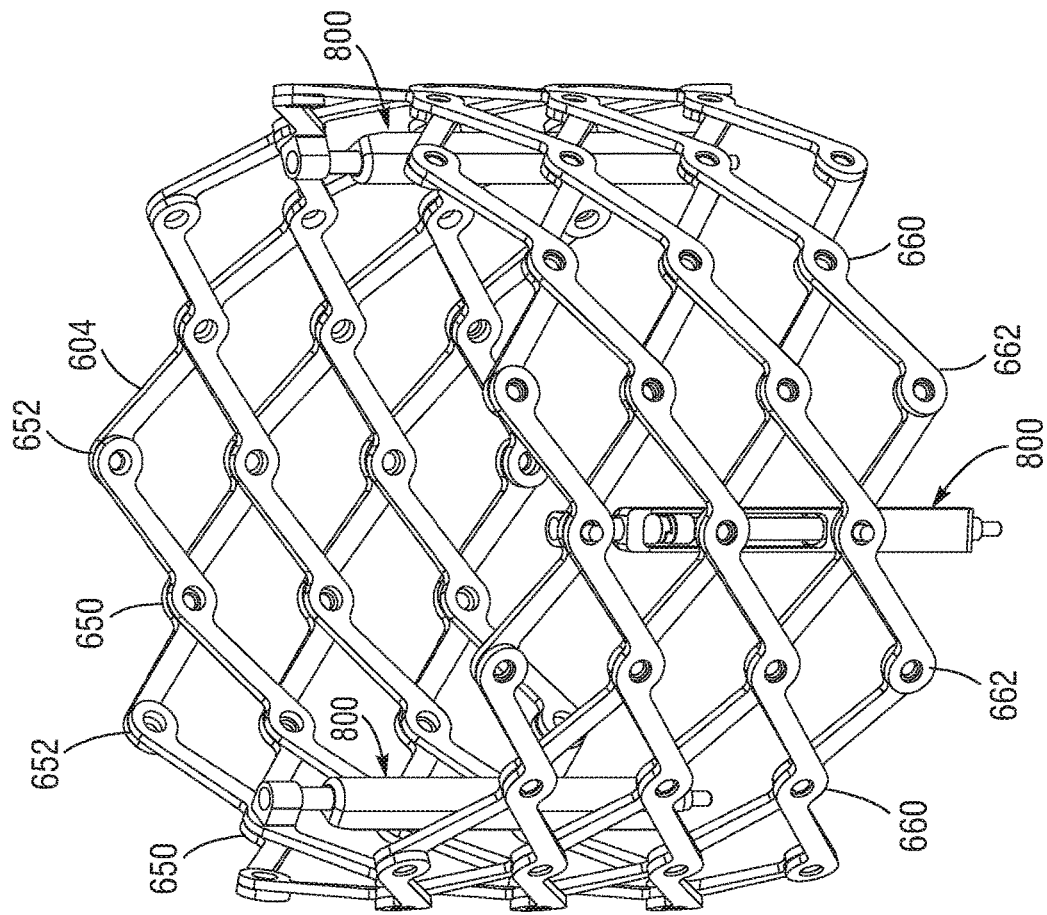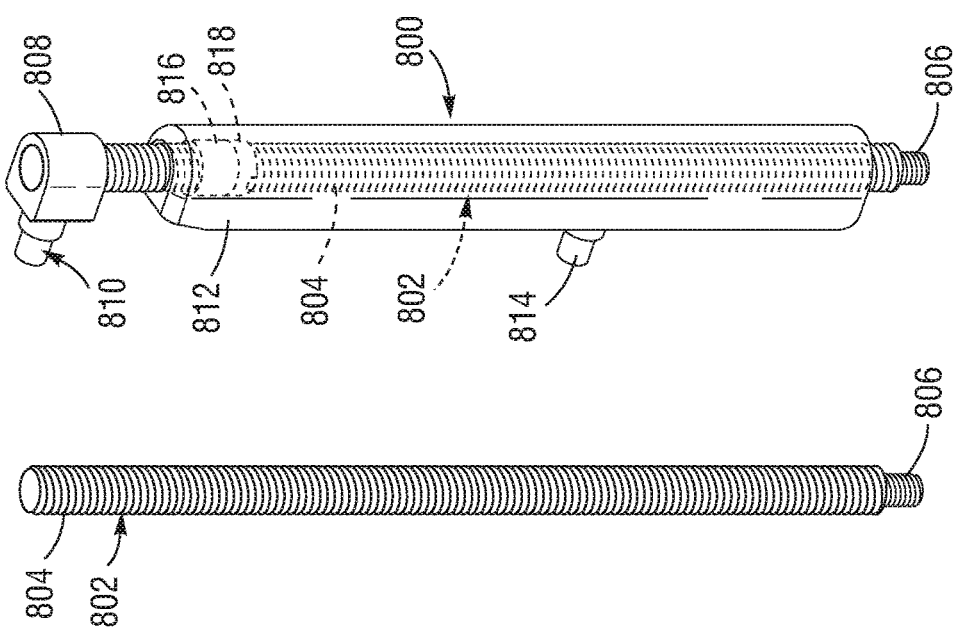

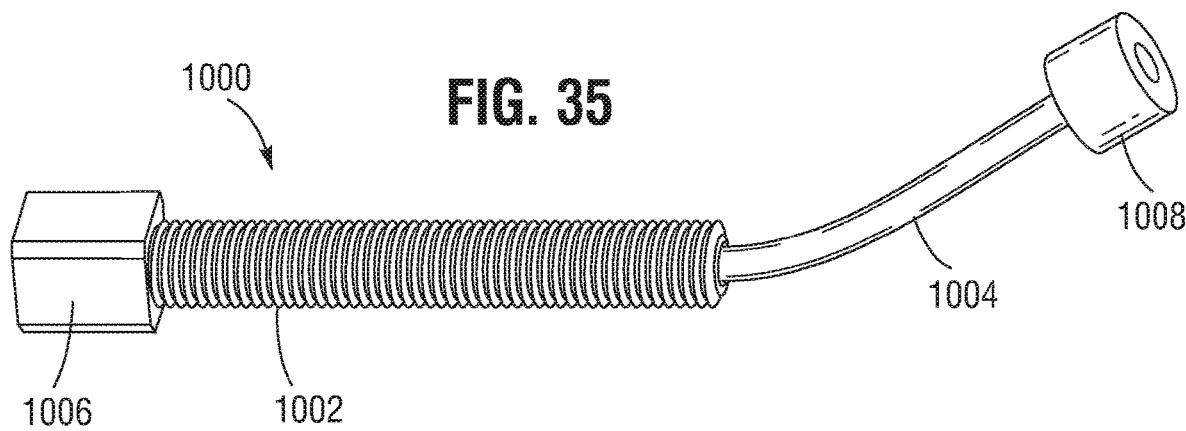

FIG. 52C 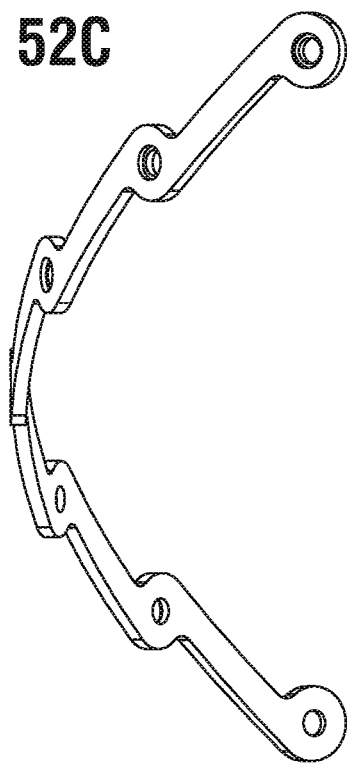 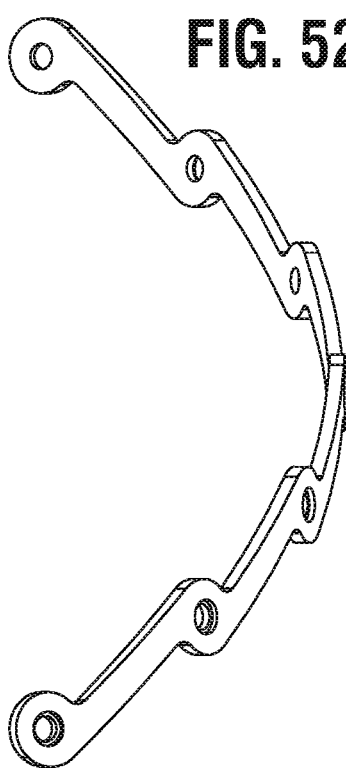 FIG. 52D
FIG. 52E
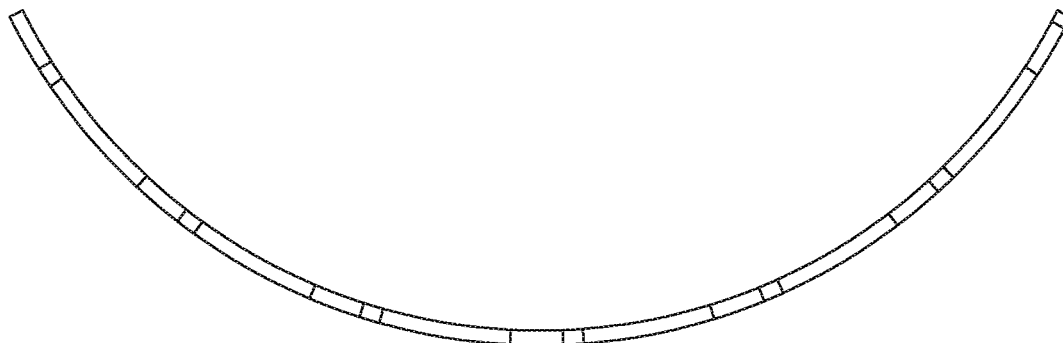
FIG. 52F
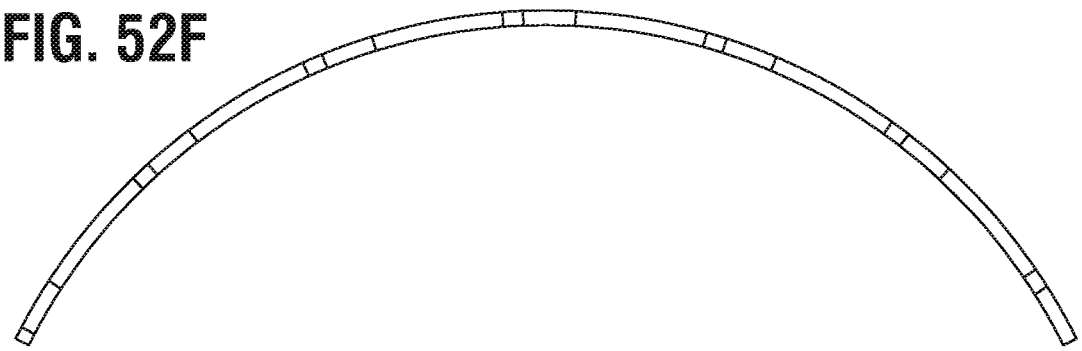

MECHANICALLY EXPANDING HEART VALVE AND DELIVERY APPARATUS THEREFOR

CROSS REFERENCE TO RELATED APPLICATIONS

This application is a divisional of U.S. application Ser. No. 15/831,197, filed Dec. 4, 2017, which claims the benefit of U.S. Provisional Appl. No. 62/430,810, filed Dec. 6, 2016, which applications are incorporated herein by reference in their entirety.

FIELD

The present disclosure relates to implantable, mechanically expandable prosthetic devices, such as prosthetic heart valves, and to methods and delivery assemblies for, and including, such prosthetic devices.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Because of the drawbacks associated with conventional open-heart surgery, percutaneous and minimally-invasive surgical approaches are garnering attention. In one technique, a prosthetic device is configured to be implanted in a less invasive procedure by way of catheterization. For example, a collapsible transcatheter prosthetic heart valve can be crimped to a compressed state and percutaneously introduced in the compressed state on a catheter and expanded to a functional size at the desired position by mechanical expansion or using a self-expanding frame or stent. Despite the recent advancements in percutaneous valve technology, there remains a need for improved transcatheter heart valves and delivery devices for such valves.

SUMMARY

Embodiments of improved prosthetic implant delivery assemblies and frames therefor are disclosed herein, as well as related methods and devices for such assemblies. In several embodiments, the disclosed assemblies are configured for delivering replacement heart valves into a heart of a patient.

In one aspect, the present disclosure provides a delivery assembly for a prosthetic implant. The delivery assembly can include a delivery apparatus and a prosthetic valve that can include a radially expandable and compressible expandable frame and a plurality of locking units coupled to the frame. The delivery apparatus can include a plurality of elongate positioning members releasably coupled to the locking units and a plurality of release members coaxially disposed with respect to, and engaged with, the locking units.

The positioning members can be moved axially to selectively expand or contract the prosthetic valve. When the prosthetic valve has been expanded to a desired size, the release members can be retracted from the locking units, causing the locking units to lock the prosthetic valve in the expanded state and causing the positioning members to decouple from the frame of the prosthetic valve.

In one representative embodiment, a prosthetic valve delivery assembly comprises a prosthetic valve and a delivery apparatus. The prosthetic valve can comprise a radially expandable and compressible expandable frame and a plurality of locking units coupled to the frame at circumferentially spaced locations. Each locking unit can comprise a respective first coupling member and a locking member. The delivery apparatus can comprise a plurality of elongate positioning members, each of the positioning members comprising a respective second coupling member at a distal end thereof, each second coupling member being releasably coupled to a respective first coupling member. The delivery apparatus can further comprise a plurality of elongate actuation members, each of the actuation members extending coaxially through one of the positioning members and having a distal end portion coupled to the frame. The delivery apparatus can further comprise a plurality of release members, each of the plurality of release members engaged with, such as extending over or through, one of the locking units. Moving the positioning members or the actuation members axially relative to one another causes the frame to expand or contract. Retracting the release members proximal to the locking members of the locking units causes the locking members to move to a locked position to resist contraction of the frame and retracting the release members proximal to the first coupling members of the locking units causes the first coupling members to decouple from the second coupling members, thereby permitting the positioning members to decouple from the locking units.

In some embodiments, the handle can be coupled to proximal end portions of the first and second actuation members. The handle can comprise a first actuator configured to produce axial movement of the positioning members. In some embodiments, the handle can comprise a second actuator configured to produce axial movement of the release members relative to the positioning members and the actuation members.

In some embodiments, each of the locking members can comprise a pair of deflectable locking jaws disposed about one of the actuation members. In some embodiments, each of the first coupling members can comprise a tab and a notch and each of the second coupling members can comprise a tab and a notch. The tab of the first coupling member can be received in the notch of the second coupling member and the tab of the second coupling member can be received in the notch of the first coupling member. In some embodiments, the tab of the second coupling member can comprise an axially extending slot.

In some embodiments, the actuation members can comprise a plurality of tethers. Ion some embodiments, a plurality of cutting members can be configured to sever the actuation members at locations proximal to the locking units. In some embodiments, each of the actuation members can comprise a plurality of longitudinally spaced apart protrusions configured to engage one of the locking members of one of the locking units.

In some embodiments, each of the locking units can comprise an elongate first member coupled to a proximal end of the frame and an elongate second member coupled to a distal end of the frame. The first and second members can be axially moveable relative to each other.

In some embodiments, each of the first members of the locking units can be releasably coupled to one of the positioning members and each of the second members can be releasably coupled to one of the actuation members. In some embodiments, retracting the release members proximal to the locking units can be effective to decouple the second members of the locking units from the actuation members.

In some embodiments, each of the first members of the locking units can comprise a first locking feature and each of the second members of the locking units can comprise a second locking feature. In these embodiments, retracting the release members proximal to the locking units can cause the first locking features to engage the second locking features to resist relative axial movement between the first and second members and contraction of the frame.

In some embodiments, each of the first locking features can comprise a deflectable locking bar and each of the second locking features can comprise at least one aperture sized to receive a locking bar. In some embodiments, the first member of each locking unit can be pivotably connected to an apex at the proximal end of the frame and the second member of each locking unit can be pivotably connected to an apex at the distal end of the frame. In some embodiments, the frame can comprise a plurality of interconnected struts having a plurality of linear segments that are laterally offset from each other in a direction perpendicular to the lengths of the struts.

In some embodiments, the struts can be connected to each other at locations between the linear segments. In some embodiments, the struts can be hingeably coupled to each other by pins extending through the struts at the locations between the linear segments. In some embodiments, each of the actuation members can extend coaxially through one of the positioning members. In some embodiments, each of the release members can extend through one of the locking units and coaxially between one of the positioning members and one of the actuation members. In some embodiments, the first coupling member of each of the plurality of locking units can comprise a radially-outwardly biased fin and wherein each of the release members is disposed about a positioning member and a first coupling member.

In another representative embodiment, a method of delivering a prosthetic valve comprises inserting a distal end of an elongate delivery apparatus into a patient, wherein the elongate delivery apparatus is releasably coupled to the prosthetic valve and the prosthetic valve comprises an expandable frame comprising a plurality of locking units. The method further comprises axially moving a plurality of elongate positioning members of the delivery apparatus to expand the prosthetic valve to an expanded state of a desired size, and removing a plurality of elongate release members from the plurality of locking units, causing the positioning members to decouple from the frame and the locking units to lock the frame in the expanded state. The elongate delivery apparatus can then be removed from the patient.

In some embodiments, removing the release members from the locking unit can allow first coupling members of the actuation members to decouple from corresponding second coupling members of the locking units. In some embodiments, axially moving a plurality of elongate actuation members of the delivery apparatus can comprise axially moving a first plurality of actuation members relative to a second plurality of actuation members of the delivery apparatus to expand the prosthetic valve, and removing the release members from the locking units can allow the first and second actuation members to decouple from the frame.

In another representative embodiment, a prosthetic valve comprises a radially expandable and compressible frame comprising a plurality of interconnected struts. Each strut has a first end, a second end, and a length extending from the first end to the second end. Each strut can comprise a plurality of linear segments that are laterally offset from each other in a direction perpendicular to the lengths of the struts. The prosthetic valve can further comprise a valvular structure, such as a plurality of leaflets, mounted to the frame and configured to regulate the flow of blood through the prosthetic valve.

In some embodiments, each of the plurality of struts is hingeably connected to at least another of the plurality of struts. In some embodiments, the prosthetic valve can further comprise a spacer disposed between a pair of connected struts. In some embodiments, the struts can be connected to each other by pins extending through the struts. In some embodiments, the frame can comprise a plurality of circumferentially spaced locking units configured to lock the frame in a radially expanded state.

In another representative embodiment, an assembly can comprise a prosthetic heart valve comprising a radially expandable and compressible annular frame, at least one linear actuator assembly coupled to the frame and at least one locking mechanism coupled to the frame. The at least one linear actuator assembly can be configured to apply a distally directed force and/or a proximally directed force to the frame to radially expand or compress the frame. The at least one locking mechanism can comprise a first sleeve member, a second sleeve member, and a first screw. The first sleeve member can be connected to the frame at a first location. The second sleeve member can have internal threads and can be connected to the frame at a second location. The first screw can be configured to engage the internal threads of the second sleeve member to retain the frame in a radially expanded state.

In some embodiments, the at least one linear actuator assembly can be releasably coupled to the frame. In some embodiments, the at least one linear actuator assembly can comprise an actuator member configured to be releasably coupled to the frame.

In some embodiments, the at least one linear actuator assembly can comprise a first threaded member connected to a distal end portion of the actuator member. The first threaded member can be configured to releasably engage a second threaded member connected to the frame.

In some embodiments, the first threaded member can comprise a second screw and the second threaded member can comprise an internally threaded nut. In some embodiments, the actuator member can comprise a cable. In some embodiments, the at least one linear actuator assembly can further comprise a sleeve positioned annularly around the actuator member.

In some embodiments, the assembly can further comprise an annular stopper connected to the frame. In these embodiments, the actuator member can extend through the stopper and the at least one linear actuator assembly can comprise a support tube positioned annularly around the actuator member and the stopper can be configured to engage a distal end of the support tube and prevent the support tube from moving distally beyond the stopper in an axial direction.

In some embodiments, the assembly can further comprise a locking tool configured to be releasably coupled to the first screw. The locking tool can comprise a tool head configured to engage and produce rotation of the first screw when the locking tool is coupled to the first screw such that the first screw moves axially through the first sleeve member and the second sleeve member.

In some embodiments, the first screw can have a screw head at its proximal end and the shape of the tool head can be configured to correspond to a shape of the screw head such that the tool head is operable to couple with the screw head such that rotation of the tool head causes rotation of the first screw.

In some embodiments, the screw head and the first sleeve member can be configured such that the screw head is prevented from moving distally beyond the first sleeve member in an axial direction.

In some embodiments, the at least one locking mechanism can further comprise an inner shaft extending partly within a lumen of the tool head. In these embodiments, the inner shaft can have a threaded surface at its distal end, the screw head can have internal threads, and the inner shaft can be configured such that its threaded surface engages the internal threads of the screw head.

In some embodiments, the first screw can further comprise a rigid portion and a flexible portion positioned between the screw head and the rigid portion. In some embodiments, the flexible portion of the first screw can comprise braded cable. In some embodiments, the flexible portion of the first screw can comprise hypotube.

In some embodiments, the first screw can further comprise a rigid portion connected to the screw head, a flexible portion connected to a distal end of the rigid portion, and a stopper connected to a distal end of the flexible portion.

In some embodiments, the assembly can further comprise a spring lock attached to the first sleeve member. In these embodiments, the spring lock can be configured to exert a radially inward directed force against the screw head to resist rotation of the screw.

In some embodiments, the assembly can further comprise a spring lock attached to the screw head. In these embodiments, the spring lock can be configured to exert a radially inward directed force against the first sleeve member to resist rotation of the screw.

In some embodiments, the assembly can further comprise a flange attached to the screw head. In these embodiments, the flange can be configured to bend against the first sleeve member to resist rotation of the screw.

In some embodiments, the assembly can further comprise a ratchet lock attached to a proximal end of the first sleeve member. In these embodiments, the ratchet lock can comprise teeth configured to allow rotation of the screw head in a first direction and prevent rotation of the screw head in a second direction.

In some embodiments, the assembly can further comprise a click lock attached to a proximal end of the first sleeve member. In these embodiments, the click lock can comprise teeth configured to resist rotation of the screw by an amount less than 90 degrees and to click when the screw is rotated 90 degrees.

In another representative embodiment, an assembly can comprise a prosthetic valve comprising a radially expandable and compressible annular frame and at least one expansion and locking mechanism. The at least one expansion and locking mechanism can comprise a linear actuator connected to the frame and a rotating member. The linear actuator can be configured to apply a distally directed force and/or a proximally directed force to the frame to radially expand or compress the frame. The rotating member can be coaxially positioned relative to the linear actuator and can be configured to retain the frame in a radially expanded state.

In some embodiments, the assembly can further comprise a first sleeve member and a second sleeve member. In these embodiments, the first sleeve member can be connected to the frame at a first location, the second sleeve member can have internal threads and can be connected to the frame at a second location, the linear actuator can be releasably coupled to the frame, the rotating member can be a screw configured to engage the internal threads of the second sleeve member, and the linear actuator can extend through a lumen of the screw.

In some embodiments, the assembly can further comprise a locking tool that is configured to be releasably coupled to the screw and rotate the screw such that the screw moves axially through the first sleeve member and the second sleeve member when the locking tool is coupled to the screw.

In some embodiments, the locking tool and the first sleeve member can be configured such that the locking tool is prevented from moving distally beyond the first threaded member in an axial direction.

In some embodiments, the screw can have a screw head at its proximal end. In these embodiments, the screw head and the first member can be configured such that the screw head is prevented from moving distally beyond the first sleeve member in an axial direction.

In some embodiments, the linear actuator can be an actuator screw having external threads and can be connected to the frame at a first location and the assembly can further comprise a sleeve connected to the frame at a second location. In these embodiments, the actuator screw can extend through a lumen of the sleeve, the rotating member can be a locking nut having internal threads configured to engage the threads of the actuator screw, and the sleeve and the locking nut can be configured such that the locking nut is prevented from moving distally beyond the sleeve in an axial direction.

In some embodiments, the actuator screw can comprise a first portion and a second portion. In these embodiments, a diameter of the second portion can be less than a diameter of the first portion.

In some embodiments, the assembly can further comprise an annular actuator member having internal threads configured to engage the threads of the second portion of the actuator screw such that when the internal threads of the actuator member are engaged with the threads of the second portion of the actuator screw, axial movement of the actuator member results in axial movement of the actuator screw.

In some embodiments, the assembly can further comprise a locking tool positioned within a lumen of the sleeve. In these embodiments, the locking tool can have a notched portion at its distal end configured to engage a corresponding notched portion at a proximal end of the locking nut such that rotation of the locking tool in a clockwise direction causes rotation of the locking nut in a clockwise direction.

In some embodiments, the locking tool can have an internally threaded surface to engage the threads of the actuator screw. In some embodiments, the assembly can further comprise a support tube positioned annularly around the locking tool. In these embodiments, a proximal end of the sleeve can be configured to engage a distal end of the support tube such that the support tube is prevented from moving distally beyond the proximal end of the sleeve in an axial direction.

In some embodiments, the assembly can further comprise a skirt. In these embodiments, the frame can comprise a plurality of rows of struts and the skirt can be positioned inside of at least one row of struts and outside of at least another row of struts.

In some embodiments, the assembly can further comprise a skirt. In these embodiments, the frame can comprise a plurality of rows of struts and the skirt can be positioned inside of at least one row of struts and outside at least another row of struts.

In another representative embodiment, an implantable prosthetic valve can comprise an annular frame and a skirt. The annular frame can comprise a plurality of rows of struts and can be radially collapsible and expandable between a radially collapsed configuration and a radially expanded configuration. The skirt can be weaved around the struts such that the skirt is positioned inside of at least one row of struts and outside of at least another row of struts.

In another representative embodiment, a method of implanting a prosthetic heart valve can comprise inserting the prosthetic heart valve into a patient's vasculature, the prosthetic heart valve being coupled to a distal end portion of a linear actuator, wherein the prosthetic heart valve comprises a frame in a radially compressed state, actuating the linear actuator to expand the frame to a radially expanded state, and rotating a screw to advance the screw through first and second members on the frame to retain the prosthetic valve in the radially expanded state.

In some embodiments, the act of rotating the screw can comprise rotating a locking tool coupled to the screw and then de-coupling the locking tool from the screw after the screw is advanced through the first and second members.

In some embodiments, the method can further comprise de-coupling the linear actuator from the frame. In some embodiments, the act of de-coupling the linear actuator can comprise unscrewing a threaded portion of the linear actuator from a corresponding threaded portion of the frame. In some embodiments, the act of actuating the linear actuator can comprise applying a proximally directed force to a distal portion of the frame with a cable.

The foregoing and other objects, features, and advantages of the invention will become more apparent from the following detailed description, which proceeds with reference to the accompanying figures.

BRIEF DESCRIPTION OF THE DRAWINGS

FIG. 8 is an enlarged perspective view of the distal end portion of the prosthetic valve delivery assembly of FIG. 1.

FIG. 9 is an enlarged side view of a locking unit and the distal end portion of a positioning member of the prosthetic valve delivery assembly of FIG. 1.

FIG. 10A is an enlarged side view of the locking and positioning member of FIG. 9, illustrating the positioning member decoupled from the locking unit.

FIG. 10B is enlarged side view of the distal end portion of the positioning member of FIG. 10A rotated 90 degrees from the orientation shown in FIG. 10A.

FIG. 11 is an enlarged side view of the locking unit and the positioning member of FIG. 9 rotated 90 degrees from the orientation shown in FIG. 9.

FIG. 14 is a perspective view of a portion of a frame of a prosthetic valve incorporating an alternative implementation of a locking unit.

FIG. 15 is an enlarged side view of the locking unit of FIG. 14.

FIG. 16A is a cross-sectional view of the locking unit of FIG. 14 shown in the fully contracted state corresponding to the fully radially expanded state of the prosthetic valve.

FIG. 16B is an enlarged cross-sectional view of a portion of the locking unit shown in FIG. 16A.

FIG. 16C is a cross-sectional view of the locking unit of FIG. 16A showing a release member retracted to release the locking unit from the delivery apparatus and lock the locking unit in the deployed state.

FIG. 16D is an enlarged cross-sectional view of a portion of the locking unit shown in FIG. 16C.

FIG. 19A shows a top view of the prosthetic valve delivery system of FIG. 18.

FIG. 19B shows a top view of another embodiment of a prosthetic heart valve delivery system.

FIG. 20A shows the frame of FIG. 18.

FIG. 20B shows the frame of FIG. 20A with a force exerted on the frame.

FIG. 20C shows the frame of FIG. 20A in a locked configuration.

FIG. 23A-23B show expanded views of the expansion mechanism.

FIGS. 24A-24D show expanded views of the locking mechanism.

FIG. 25A-25D show exploded views of the locking mechanism.

FIG. 27 is a perspective view of a prosthetic valve frame, shown in a radially collapsed state, having a plurality of expansion and locking mechanisms, according to another embodiment.

FIG. 28 is a perspective view of the frame and the expansion and locking mechanisms of FIG. 27, with the frame shown in a radially expanded state.

FIG. 29A is a perspective view of a screw of one of the expansion and locking mechanisms of FIG. 27.

FIG. 29B is a perspective view of one of the expansion and locking mechanisms of FIG. 27.

FIG. 29C is another perspective view of the frame and the expansion and locking mechanisms of FIG. 27, with the frame shown in a radially expanded state.

FIG. 35 shows another exemplary flexible screw that can be implemented in a prosthetic heart valve.

FIGS. 52A-52F show various views of a strut for a frame of a prosthetic valve, such as the frame of FIG. 51. FIG. 52A is an elevation view of the outside of the strut. FIG. 52B is an elevation view of the inside of the strut. FIG. 52C is an end view of the strut. FIG. 52D is an end view of the opposite end of the strut. FIGS. 52E-52F are top and bottom plan views of the strut, respectively.

FIG. 53A is a front elevation view of the frame, which is symmetrical about a central longitudinal axis. FIG. 53B is a front elevation view of the frame with the rear half of the frame removed for purposes of illustration. FIG. 53C is a top plan view of the frame. The bottom plan view is a mirror image of the top plan view. FIG. 53D is a perspective view of the frame.

DETAILED DESCRIPTION

Described herein are examples of prosthetic implant delivery assemblies and components thereof which can improve a physician's ability to control the size of a mechanically-expandable prosthetic implant, such as prosthetic valves (e.g., prosthetic heart valves or venous valves), stents, or grafts, as well as facilitate separation of the prosthetic implant from the delivery assembly, during the implantation procedure. The present disclosure also provides frames for use with such prosthetic implants. The frames can comprise struts shaped to reduce or eliminate pinching of the soft components of the prosthetic implant (e.g., leaflets of the implant) when the implant is radially compressed to a delivery configuration for delivery into a patient.

Figure 1:
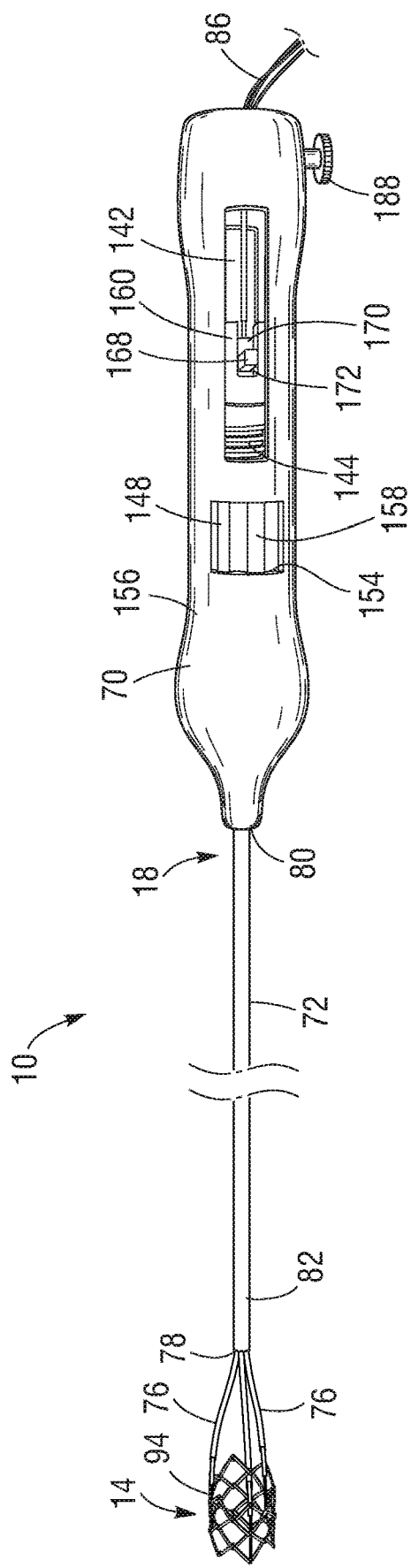
FIG. 1 is a side elevation view of an embodiment of a prosthetic valve delivery assembly.

FIG. 1 shows an example of a prosthetic implant delivery assembly 10 according to one embodiment of the present disclosure. The delivery assembly 10 can include two main components: a prosthetic heart valve 14 and a delivery apparatus 18. The prosthetic valve 14 can be releasably coupled to the delivery apparatus 18, as further described below. It should be understood that the delivery apparatus 18 and other delivery apparatuses disclosed herein can be used to implant prosthetic devices other than prosthetic valves, such as stents or grafts.

Figure 2:
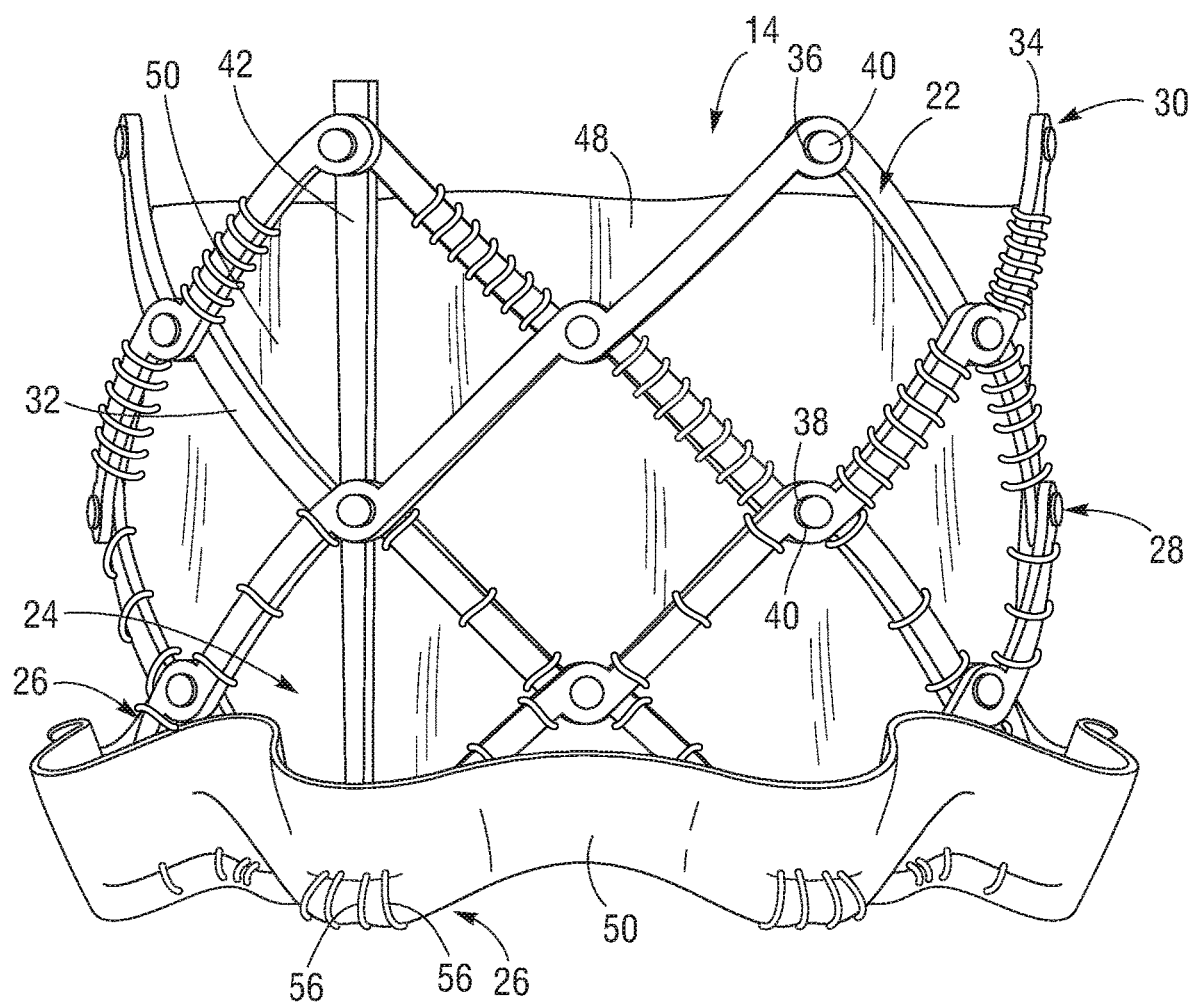
FIG. 2 is a side elevational view of a prosthetic valve, according to one embodiment.

FIG. 2 is a side elevational view of the prosthetic valve 14 shown in its deployed, radially expanded configuration. While only one side the prosthetic valve 14 is shown in the drawings, it should be appreciated that the opposite side is similar to the portion shown. The prosthetic valve 14 can include an annular stent or frame 22, and a valve structure 24 which can be coupled to the frame 22. The frame 22 can have an inflow end portion 26, an intermediate portion 28, and an outflow end portion 30. The prosthetic valve 14 can define a longitudinal axis extending through the inflow end portion 26 and the outflow end portion 30.

The frame 22 can be made of any of various suitable materials, such as stainless steel or a nickel titanium alloy ("NiTi"), for example Nitinol. The frame 22 can include a plurality of interconnected lattice struts 32 arranged in a lattice-type pattern and forming a plurality of apices 34 at the outflow end 30 of the prosthetic valve 14. The struts 32 can also form similar apices at the inflow end of the prosthetic valve (which are covered by a skirt 50 in FIG. 2). The lattice struts 32 are shown as positioned diagonally, or offset at an angle relative to, and radially offset from, the longitudinal axis of the prosthetic valve. In other implementations, the lattice struts 32 can be offset by a different amount than depicted in FIG. 2, or some or all of the lattice struts 32 can be positioned parallel to the longitudinal axis of the prosthetic valve 14.

The lattice struts 32 can be pivotably coupled to one another. In the illustrated embodiment, for example, the end portions of the struts 32 forming the apices 34 at the outflow end 30 and at the inflow end 26 of the frame 22 can have a respective opening 36. The struts 32 also can be formed with apertures 38 spaced apart along their lengths between the opposite ends of the struts. Respective hinges can be formed at the apices 34 and at the locations where struts 32 overlap each other between the ends of the frame via fasteners 40, which can comprise rivets or pins that extend through the apertures 36, 38. The hinges can allow the struts 32 to pivot relative to one another as the frame 22 is expanded or contracted, such as during assembly, preparation, or implantation of the prosthetic valve 14. For example, the frame 22 (and thus the prosthetic valve 14) can be manipulated into a radially compressed or contracted configuration (see, e.g., FIGS. 6 and 7) and inserted into a patient for implantation. Once inside the body, the prosthetic valve 14 can be manipulated into an expanded state (e.g., FIGS. 2 and 4) and then released from the delivery apparatus 18 (e.g., FIG. 1), as further described below.

The frame 22 can be formed using any suitable technique. Suitable techniques can include separately forming individual components (e.g., the struts 32 and fasteners 40) of the frame and then mechanically assembling and connecting the individual components to form the frame 22. The struts and fasteners can be formed, for example, by laser cutting those components from sheets or tubes of metal, or by electroforming (electroplating or electrodeposition) or physical vapor deposition. In some embodiments, electroforming or physical vapor deposition can be used to form subcomponents of the frame 22 or the entire frame 22 with pivotable connections between the struts. In one implementation, for example, electroforming or physical vapor deposition can be used to form struts 32 having integral fasteners 40. The individual struts can be assembled together into a frame by inserting the integral fasteners 40 of each strut through a corresponding aperture of an adjacent strut. In some embodiments, electroforming or physical vapor deposition can be used to form the entire frame in its final, cylindrical shape. In other embodiments, electroforming or physical vapor deposition can be used to form the entire frame in a flattened configuration, after which the ends of the flattened frame are connected to each other to form the final cylindrical shape of the frame.

In other embodiments, the lattice struts 32 are not coupled to each other with respective hinges (e.g., fasteners 40) but are otherwise pivotable or bendable relative to each other to permit radial expansion and contraction of the frame. For example, the frame 22 can be formed (e.g., via laser cutting, electroforming or physical vapor deposition) from a single piece of material (e.g., a metal tube).

In addition to the lattice struts 32, the frame 22 can include one or more longitudinally extending support struts 42. The support struts 42 can be circumferentially spaced about the frame 22 and coupled, including being pivotably coupled, to the lattice struts 32. The support struts 42 can be positioned parallel to, and radially spaced apart from, the longitudinal axis of the prosthetic valve. The support struts 42 can enhance the rigidity of the frame 22 and help the frame 22 maintain a uniform shape as it is expanded or contracted. In some implementations, the frame 22 does not include the support struts 42. The support struts 42 can be connected to the lattice struts 32 at the hinge joints formed by fasteners 40 that can extend through respective apertures in the lattice struts and the support struts.

Figure 3A:
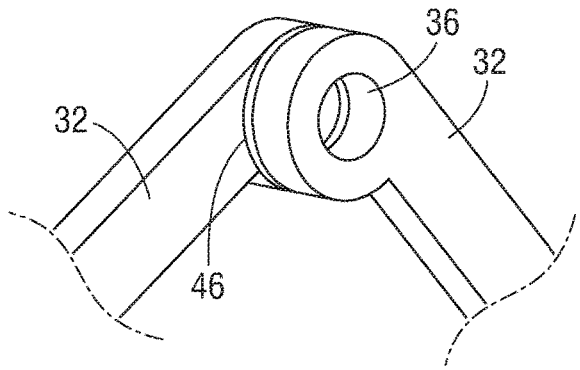
FIGS. 3A and 3B are enlarged perspective views and side views, respectively, of an embodiment of coupled frame struts useable in the prosthetic valve of FIG. 2.
Figure 3B:
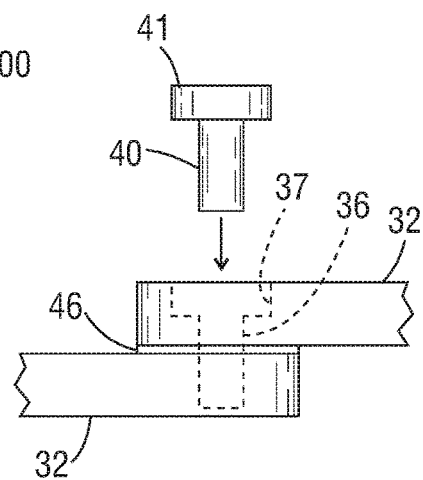

With reference to FIGS. 3A and 3B, a spacer 46, such as a washer or bushing, can be disposed in a joint between lattice struts 32, or a joint between lattice struts 32 and support struts 42 (not shown). When the lattice struts 32 and/or support struts 42 are pivotably coupled to one another, the spacers 46 can assist the lattice struts 32, or lattice struts 32 and support struts 42, in moving relative to one another. The spacer 46 can also act to space the lattice struts 32 from one another, or from the support struts 42. In some implementations, the frame 22 does not include the spacers 46, or the lattice struts 32, or lattice struts 32 and support struts 42, are spaced apart in a different manner.

In particular embodiments, the fasteners 40 do not extend radially outwardly from their respective apertures 36, 38 in the struts and can be contained completely within the apertures. As shown in FIG. 3B, for example, each of the apertures 36 on the radially outermost struts 32 can include a counter-bore or enlarged recessed portion 37 that is sized to receive the head portion 41 of a respective fastener 40 (e.g., a rivet). The head portion 41 can be received entirely within the counter-bore 37 and does not extend radially outwardly from the counter-bore, for example, the head portion 41 can be flush with the outer surface of the strut 32. Similarly, the apertures 38 also can be formed with counter-bores to receive the head portions 41 of the fasteners. In this manner, the fasteners 40 do not increase or contribute to the overall crimp profile of the prosthetic valve and do not interfere with or place undue stresses on the delivery sheath of the valve (e.g., sheath 82 in FIG. 1).

Returning to FIG. 2, the prosthetic valve 14 can include a valvular structure 24 to regulate the flow of blood through the prosthetic valve. The valvular structure 24 can comprise, for example, a leaflet assembly 48 comprising one or more leaflets made of a flexible material. The leaflets of the leaflet assembly 48 can be made from in whole or part, biological material (e.g., pericardial tissue, such as bovine or equine pericardium), bio-compatible synthetic materials, or other such materials, such as those described in U.S. Pat. No. 6,730,118, which is incorporated herein by reference.

The prosthetic valve can also include an annular skirt or sealing member 50 that can be secured to the outer surface of the inflow end portion 26 of the frame 22, for example, with sutures 56 adjacent the inflow end portion 26 of the frame 22. The inflow end portion of the leaflet assembly 48 can be secured to the frame 22 and/or the skirt 50, for example using sutures 56. The skirt 50 helps establish a seal with the native tissue at the implantation site to prevent or minimize perivalvular leakage. In alternative embodiments, the prosthetic valve can have a skirt or sealing member mounted on the inside of the frame or a skirt or sealing member mounted on the inside and outside of the frame. The skirt can be formed from natural tissue (e.g., pericardial tissue) or any of various biocompatible synthetic materials, including biocompatible fabrics (e.g., polyethylene terephthalate (PET) fabric).

Further details regarding transcatheter prosthetic heart valves, including the manner in which the valve structure 24 can be coupled to the frame 22 of the prosthetic valve 14, can be found, for example, in U.S. Pat. Nos. 6,730,118, 7,393,360, 7,510,575, 7,993,394, and 8,652,202, which are incorporated herein by reference in their entireties.

Figure 4:
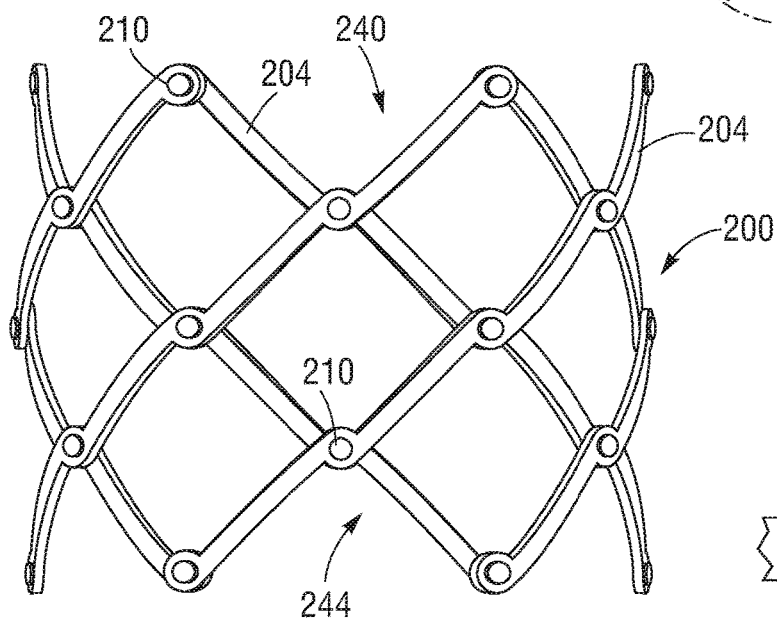
FIG. 4 is a side elevational view of another embodiment of a frame that can be used in the prosthetic valve of FIG. 2.

FIG. 4 is a side elevational view of a portion of a frame 200 that can be used with a prosthetic valve in at least certain embodiments of the present disclosure. While only one side of the frame 200 is depicted in FIG. 4, it should be appreciated that the opposite side can be similar to the portion shown. The frame 200 is similar to the frame 22 discussed above but does not include the longitudinal struts 42. The frame 200 can include a plurality of lattice struts 204. Each of the lattice struts 204 can include a plurality of apertures 208. The apertures 208 can be used to connect the lattice struts 204 to one another using fasteners 210, such as described above for the lattice struts 32 (FIG. 2). In other implementations, the apertures 208 and fasteners 210 can be omitted. For example, the lattice struts 204 can be fixedly connected to one another, such as by welding or adhesion, or by laser-cutting the individual struts of the frame from a metal tube. Although not shown in FIG. 4, a spacer may be included between the lattice struts 204, such as intermediate the portions of the lattice struts 204 having the apertures 208. In a particular example, the spacers can be configured as described above for the spacer 46. Similarly, if desired, the frame 200 can include support struts (not shown) that can be analogous to the support struts 42 (FIG. 2).

Figure 5:
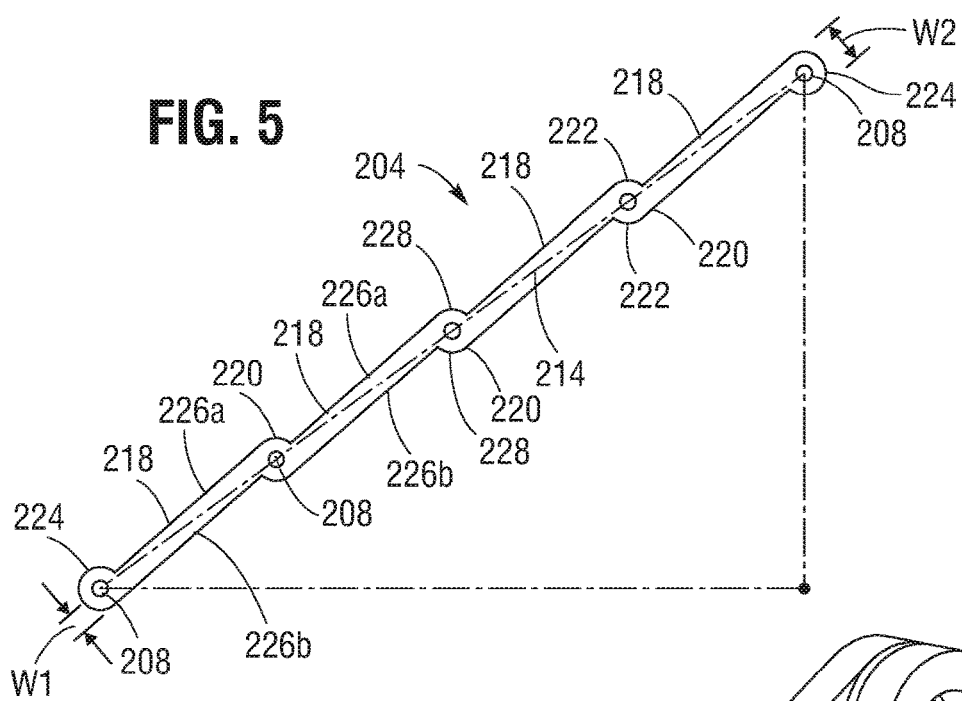
FIG. 5 is a side view of an embodiment of a strut for a frame of a prosthetic valve, such as the frame of FIG. 2, or the frame of the FIG. 4.

As best shown in FIG. 5, each lattice strut 204 can have an offset, or zig-zag, pattern defined by a plurality of offset linear portions or segments 218. The linear segments 218 in the illustrated embodiment are arranged end-to-end relative to each other with adjacent ends interconnected to each other by intermediate segments 220. The strut 204 can have enlarged end portions 224 that form the apices at the inflow and outflow end of the frame. Each linear segment 218 is slightly laterally offset from an adjacent linear segment 218 in a direction perpendicular to the overall length of the strut 204 to provide the zig-zag pattern to the strut. Each of the intermediate segments 220 and end portions 224 can have a respective aperture 208 at its geometric center for receiving a fastener 210.

The amount of offset of each linear segment 218 relative to an adjacent linear segment along the length of the strut 204 can be constant such that an imaginary line 214 can pass through the aperture 208 of each intermediate segment 220 along the entire length of the strut. In alternative embodiments, the amount of offset between two adjacent linear segments 218 can vary along the length of the strut. For example, the amount of offset between linear segments 218 adjacent the outflow end of the frame can be greater than the amount of offset between linear segments 218 adjacent the inflow end of the frame, or vice versa.

The linear segments 218 can include at least substantially flat or linear opposing longitudinal edges 226a, 226b extending between curved or rounded edges 228 of the intermediate segments 220. In alternative embodiments, the opposing edges 228 of the intermediate segments 220 can be substantially flat or linear edges that extend at an angle between respective ends of the edges 226a, 226b of the liner segments 218.

As best shown in FIG. 5, the width W1 of each liner segment 218 is defined as the distance measured between the opposing edges 226a, 226b of a segment 218. In the illustrated embodiment, the width W1 is constant along the length of the strut 204. As such, each longitudinal edge 226a is laterally offset from an adjacent longitudinal edge 226a of an adjacent linear segment 218, and each longitudinal edge 226b is laterally offset from an adjacent longitudinal edge 226b of an adjacent linear segment 218. The width W2 of each intermediate segment 220 and end portion 224 can be greater than the width W1 of the linear segments 218.

In alternative embodiments, the width W1 of each linear segment 218 can vary along the length of a strut. For example, the width W1 of a linear segment 218 adjacent the inflow end of the frame can be greater than the width W1 of a linear segment 218 adjacent the outflow end of the frame, or vice versa. Further, where the width W1 of the linear segments 218 vary along the length of a strut 204, a linear segment can have one longitudinal edge 226a or 226b that is collinear with a longitudinal edge of an adjacent linear segment on the same side of the strut, while the other longitudinal edge 226a, 226b is laterally offset from the longitudinal edge of an adjacent linear strut on the same side of the strut. In other words, the strut 204 can have an overall zig-zag or offset pattern by virtue of the varying widths W1 of the linear segments.

Figure 6:
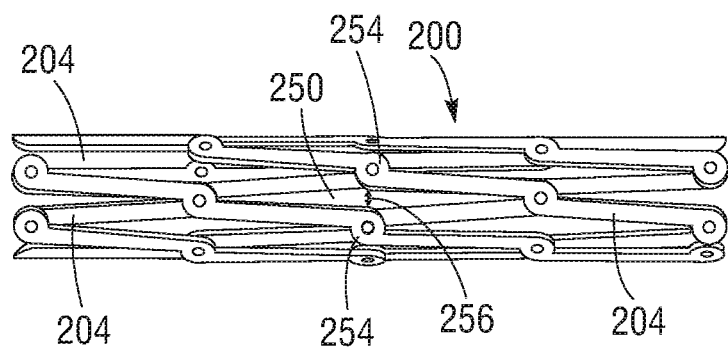
FIG. 6 is a side view of the frame of FIG. 4 shown in a radially compressed state.
Figure 7:
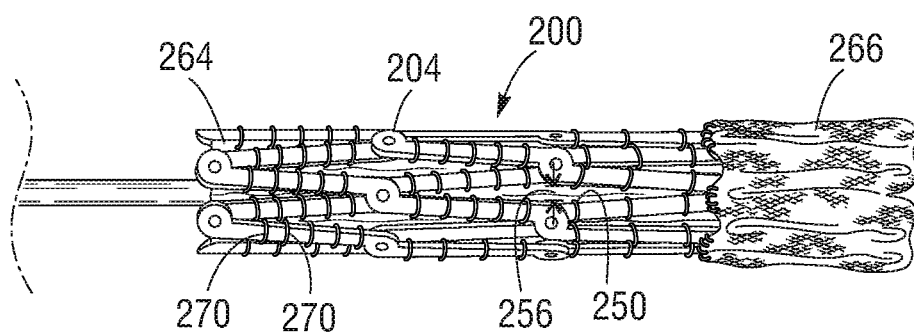
FIG. 7 is a side view of a prosthetic valve incorporating the frame of FIG. 4 shown in a radially compressed state.

The offset, or zig-zag, pattern of the strut segments 218 can help space apart the struts 204 in the circumferential direction when the frame 200 is in a radially compressed state, as shown in FIGS. 6 and 7. As shown, the open lattice structure of the frame 200 defining open cells 250 between the struts 204 can be preserved even when the frame 200 is fully compressed or contracted. For example, with reference to FIG. 6, although the width of the cells 250 along the length of the frame 200 can vary between adjacent struts, a gap 256 remains at the middle of a cell 250 between two adjacent pivot joints 254.

When the frame 200 is incorporated in a prosthetic valve (e.g., the prosthetic valve 14), the spaced-apart nature of the struts 204, including the gaps 256, can assist in protecting the soft components of the prosthetic valve as the frame 200 is expanded and contracted. FIG. 7, for example, shows a prosthetic valve comprising the frame 200, a skirt 266 mounted on the outside of the frame 200 and a leaflet assembly 264 mounted inside of the frame 200. An inner skirt (not shown) also can be mounted inside of the frame. The skirt 266 and leaflet assembly 264 can be coupled to the frame 200, such as with sutures 270. The sutures 270 can extend through the material of the skirt 266 and/or the leaflet assembly 264 and radially about the struts 204. The gaps 256 created by the offset configuration of the struts 204 can protect the leaflets 264, the skirt 266, and/or the sutures 270 from being pinched or sheared between adjacent struts 204 when the prosthetic valve is radially compressed. In this manner, the soft components of the prosthetic valve are protected against damage that can occur from contact with the metal struts of the frame.

The delivery apparatus 18 of FIG. 1 is particularly suited for implanting the prosthetic valve 14 or any of the other prosthetic valves disclosed herein. However, it should be noted that any of the prosthetic valves disclosed herein can be implanted using other suitable delivery apparatuses. For example, any of the prosthetic valves disclosed herein can be crimped over an inflatable balloon of a conventional balloon catheter. Once delivered to the implantation site, the balloon can be inflated to expand the prosthetic valve to its fully functional size.

Referring again to FIG. 1, the delivery apparatus 18 can include a handle 70, an elongate shaft 72 extending distally from the handle 70, a plurality of first actuation members 76 (also referred to as elongate positioning members or actuator members), such as in the form of positioning tubes, extending through the shaft and distally outwardly from a distal end 78 of the shaft 72, a plurality of release members 106 (FIG. 9) extending through respective positioning members 76, and a plurality of second actuation members 86 (also referred to as "tethers") extending through respective release members 106. The positioning members 76 can be at least partially disposed radially within, and extend axially through, one or more lumens of the shaft 72. For example, the positioning members 76 can extend through a central lumen of the shaft 72 or through separate respective lumens formed in the shaft 72.

Figure 13:
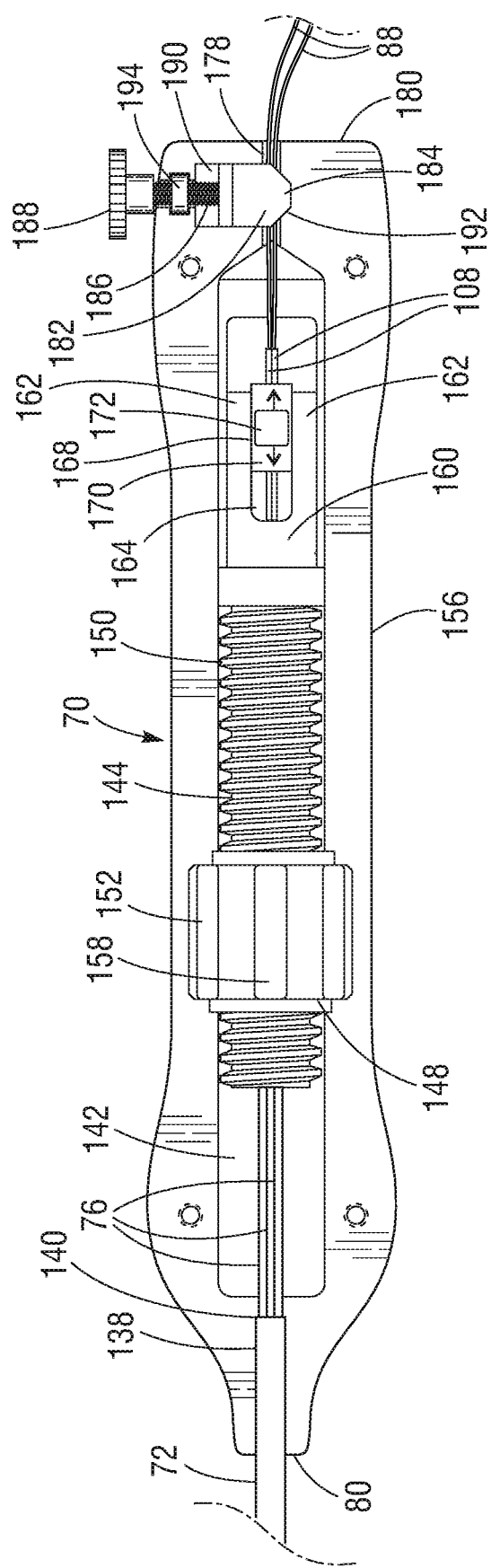
FIG. 13 is an enlarged cross-sectional view of the handle of the prosthetic valve delivery assembly of FIG. 1.

The shaft 72 can have a distal end portion 82 that can function as a sheath for containing or housing the prosthetic valve 14 in a radially compressed state for delivery through a patient's vasculature. In this regard, the distal end portion 82 can have a lumen that is sized to receive the prosthetic valve 14 in a radially compressed state. As shown in FIG. 13, the proximal end portion of the shaft 72 can extend into an axially extending bore 138 formed in the distal end portion of the handle 70. The proximal end portion of the shaft 72 can be retained within the axial bore 138 through pressure or frictional contact with the bore 138, using an adhesive, a clamp, a fastener, by thermally bonding the catheter 72 to the bore 138, or by some other technique or mechanism.

The positioning members 76 have distal end portions that can be releasably connected to the prosthetic valve 14 via respective release-and-locking units 94 (as best shown in FIG. 8). As shown in FIG. 13, the positioning members 76 can extend through the shaft 72, and proximally beyond a proximal end 140 of the shaft, and into a central bore 142 of the handle 70. A lead screw 144 can be disposed within the central bore 142 of the handle 70. The proximal ends of the positioning members 76 can be secured to the lead screw 144, such as being received within a bore (not shown) of the lead screw 144, where they can be secured by pressure or frictional contact with the bore of the lead screw 144, using an adhesive, a clamp, a fastener, thermal bonding, or another suitable technique or mechanism.

As shown in FIGS. 8 and 9, each actuation member 86 can extend through a lumen of a respective positioning member 76. The actuation members 86 can be coupled at their distal end portions to the distal end 60 of the frame 22. For example, the distal end portion of each actuation member 86 can be connected to an apex 34 at the distal end 60 of the frame, such as by welding, an adhesive, or a mechanical fastener. Each actuation member 86 can also extend through a lumen of a respective locking unit 94 that can be coupled to the frame 22, such as to an apex 34 at a proximal end 62 of the frame. The actuation members 86 can extend proximally into and through the handle 70. Proximal end portions 88 of the actuation members 86 can be releasably retained by a clamping member 182 mounted in or on the handle 70 (FIG. 13).

The actuation members 86 function to apply a proximally directed pulling force to the distal end 60 of the frame in cooperation with the positioning members 76 that apply a distally directed pushing force to the proximal end 62 of the frame to effect radially expansion of the frame 22. In particular embodiments, the actuation members 86 can comprise a relatively flexible but relatively non-elastic material that can effectively transfer pulling forces generated at the handle 70 to the distal end of the frame 22. For example, the actuation members 86 can comprise wires, sutures, strings, or similar materials. In other embodiments, the actuation members 86 can be relatively stiffer component, such as shaft or rod, that can transfer proximally directed pulling forces to the frame as well as distally directed pushing forces to the frame.

The release members 106 have distal end portions 107 that extend coaxially through respective locking units 94 (FIG. 9) and proximal end portions 108 that extend into the handle 70 (FIG. 13). The proximal end portions 108 of the release members 106 can extend through the lead screw 144 and can be secured to a release knob 168 within the handle 70.

Referring to FIGS. 1 and 13, a threaded actuator nut 148 can be disposed about the lead screw 144. Internal threads (not shown) of the threaded actuator nut 148 can engage threads 150 of the lead screw 144. An outer surface 152 of the threaded actuator nut 148 can extend through an aperture or window 154 formed in the outer surface 156 of the handle 70. The outer surface 152 of the threaded actuator nut 148 can include a texture, such as ridges 158, to aid a user in grasping and rotating the threaded actuator nut 148.

Rotation of the threaded actuator nut 148 in a first direction can cause the lead screw 144 to translate axially in the distal direction relative to the handle 70, thereby causing the positioning members 76 to translate distally through the lumen of the shaft 72. Rotation of the threaded actuator nut 148 in the opposite direction can cause the lead screw 144 to translate proximally relative to the handle, thereby causing the positioning members 76 to retract or translate proximally through the lumen of the shaft 72.

In particular implementations, the number and spacing of the threads 150 of the lead screw 144 (and thus the mating threads of the threaded actuator nut 148), and the axial length of the lead screw 144, can be selected to provide a desired degree of travel for the positioning members 76 and the release members 106. For example, the desired degree of travel can be sufficient to allow the frame 22 (and thus the prosthetic valve 14) to be manipulated between a fully expanded state (such as shown in FIGS. 2 and 8) and a fully contracted or compressed state (such as shown in FIGS. 6 and 7), including states in between being fully compressed or contracted and fully expanded, as further described below.

The release-and-locking units 94 (also referred to as "locking units") in the illustrated embodiment are configured to releasably connect the positioning members 76 to the frame 22 of the prosthetic valve 14 and to selectively secure the actuation members 86 to retain the prosthetic valve 14 in a deployed and expanded state. With reference to FIGS. 8-11, the locking units 94 can comprise a generally cylindrical body 96, which can be secured to the frame 22 of the prosthetic valve 14 by a fastener 130 (e.g., a pin or rivet). The fastener 130 can extend through an aperture 132 (FIG. 11) formed in the body 96 and through one or more corresponding apertures 36 in the frame struts 32 forming the apices 34 of the frame (FIG. 8).

The body 94 can comprise a locking feature, such as in the form of a clamp 98, disposed adjacent a distal end 100 of the locking unit 94 for selectively engaging an actuation member 86. The clamp 98 can comprise, for example, a pair of diametrically opposed jaws 102 that are biased radially inwardly toward each other (as best shown in FIG. 11). A release member 106 can be disposed within a lumen of each locking unit 94 to retain the jaws 102 of the clamp in a non-engaged or non-locking state during delivery of the prosthetic valve 14 (FIG. 9). Each release member 106 can extend proximally through a respective positioning member 76 to the handle 70. As discussed above, the proximal end portions 108 of the release members can be secured to a release knob 168 in the handle (FIG. 13). Each actuation member 86 can extend proximally through a lumen of a respective release member 106 into the handle 70.

In particular implementations, the release members 106 can be made from any suitable biocompatible metallic material or a polymeric material. In some examples, the material can be selected to allow the release members 106 to be easily moveable relative to the jaws 102 during valve deployment, as further described below. For example, the release members 106 can be made from a lubricious or low friction material (e.g., PTFE) or can have an outer layer made from a lubricious or low friction material (e.g., PTFE).

When the release members 106 are disposed within the locking units 94 extending between the jaws 102, the jaws 102 are held in an unlocked stated and are prevented from contacting the actuation members 86. In the unlocked state, the actuation members 86 and the positioning members 76 can move freely in the axial direction with respect to one another to control radial expansion and compression of the prosthetic valve 14. When the prosthetic valve 14 is to be released from the delivery apparatus 18, the release members 106 can be retracted proximally relative to the locking units 94 and the positioning members 76. As shown in FIGS. 10A and 11, once the release members 106 are removed from engagement with the jaws 102, the jaws 102 can move to a locked or engaged state engaging the actuation members 86, thus securing the actuation members 86 from further axial movement, thus retaining the frame 22 of the prosthetic valve 14 in a desired expanded state.

Referring back to FIG. 10, the locking units 94 can be releasably coupled to the positioning members 76 by the release members 106. In the illustrated embodiment, for example, a distal end portion 110 of each positioning member 76 can include a coupling portion 112 that can include a tab 114 and a notch 116. Each locking unit 94 can include a corresponding notch 120 configured to receive the tab 114 of the positioning member 76. Similarly, each locking unit 94 can include a tab 122 to be inserted into, and received by, the notch 116 of a respective positioning member 76. The tabs 114, 122 and notches 120, 116, along with the release member 106, collectively can form a releasable, interlocking joint. The engagement of the tabs 114, 122 with the notches 120, 116 prevent axial separation of the positioning member 76 from the locking unit 94, while the release member 106, which extends through the tabs 114, 122 in the locked state, prevents lateral separation of the positioning member 76 from the locking unit 94.

As shown in FIG. 10B, the tab 114 of the positioning member 76 can include an axially extending slot 128. The slot 128 can be sized to allow the tab 114 to be placed around the actuation member 86 or removed from the actuation member 86 by passing the actuation through the slot 128. However, the slot 128 desirably is narrower than the diameter of the release member 106 to prevent lateral separation of the positioning member 76 from the locking unit 94 when the release member 106 is in a position extending through the tabs 114, 122 as depicted in FIG. 9. As noted above, retraction of the release member 106 from the jaws 102 of the clamp 98 allows the jaws to engage the actuation member 86. Further retraction of the release member 106 until the distal end of the release member 106 is proximal to the tab 122 and the notch 116 allows the distal end portion 110 of the positioning member 76 to be separated from the locking unit 94 in a lateral direction (in a direction perpendicular to the length of the locking unit and the positioning member), as depicted in FIG. 10A. As the positioning member 76 moves in a lateral direction away from the locking unit 94, the actuation member 86 can pass through the slot 128 in the tab 114.

As further shown in FIG. 10A, the tabs 114, 122 can be formed with respective inclined cam surfaces 124, 126, respectively, to facilitate the separation of the positioning member 76 from the locking unit 94. Each cam surface 124, 126 is inclined relative to the longitudinal axis of the positioning member 76 at angle less than 90 degrees. As such, applying a proximally directed force to the positioning member 76 in the direction of arrow 134 (such as by applying a pulling force to the positioning member at handle 70) causes the positioning member 76 to slide laterally away from the locking unit 94 in the direction of arrow 136.

The locking units 94 and/or the positioning members 76 can include a cutting mechanism to cut the portions of the actuation members 86 that extends proximally beyond the jaws 102 of the clamps 98 after the prosthetic valve is expanded and the release members are retracting to actuate the clamps. For example, a blade, or other cutting surface, can be placed across the slot 128, such that the actuation members 86 can be severed when they pass through the slot 128 during lateral separation of the positioning member 76 away from the locking unit 94.

In another example, the locking units 94 can include a clamping member that can include cutting jaws (such as sharpened or serrated jaws) positioning proximal to the jaws 102. The cutting jaws, like the jaws 102, can be retained in an open position away from the actuation member by the release member 106. When the release member 106 is retracted out of engagement with the cutting jaws, the cutting jaws can deflect radially inwardly against the actuation member 86, thereby severing it at that location. In further examples, a separate cutting device can be used to sever the actuation members 86 at a desired location after the positioning members 76 are released from the prosthetic valve 14, and optionally, after the delivery apparatus 18 is removed from the body.

Referring again to FIGS. 1 and 13, the lead screw 144 includes an extension portion 160 that extends proximally from the threaded portion of the lead screw. The extension portion 160 can comprise two leg portions 162 defining a U-shaped aperture or slot 164 between the leg portions 162. The release knob 168 can comprise a slidable member 170 disposed between the leg portions 162 and a user-engageable portion 172 extending radially outwardly from the slidable member 170. The proximal end portions 108 of the release members 106 can be fixedly secured to the slidable member 170, such as with a suitable adhesive, such that axial movement of the slidable member 170 in the distal and proximal directions causes corresponding movement of the release members.

The release knob 168 can be configured to be movable with, and also independently of, the lead screw 144. As noted above, axial movement of the lead screw 144 causes corresponding movement of the positioning members 76. Thus, when the release knob 168 is retained relative to the extension portion 160 of the lead screw 144, axial movement of the lead screw 144 causes the release knob 168 and the release members 106 to move with the positioning members 76, such as during deployment and expansion of the prosthetic valve. When the release knob 168 is not retained relative to the extension portion 160 of the lead screw 144, the release knob 168 can be translated axially relative to the extension portion, thereby effecting axial movement of the release members 106 relative to the positioning members 76 to actuate the clamping mechanism 98 of the locking unit 94 and release the positioning members 76 from the frame 22 of the prosthetic valve.

Various mechanisms can be used to selectively and releasably retain the release knob 168 axially relative to the extension portion 160 of the lead screw 144. For example, a moveable pin or similar mechanism can be inserted through the slidable member 170 and one or both leg portions 162 of the extension portion 160 to retain the axial position of the slidable member 170 relative to the lead screw 144. Removing the pin from the slidable member 170 and/or the leg portions 162 allows axial movement of the release knob 168 relative to the lead screw.

In another embodiment, the slidable member 170 can be configured to move between a first position where it is frictionally engaged by the extension portion 160 and a second position where the slidable member 170 is no longer frictionally engaged by the extension portion 160. In the first position, the axial movement of the lead screw 144 causes corresponding movement of the release knob 168. In the second position, the release knob 168 can be moved axially independently of the lead screw 144 in the distal and proximal directions.

The actuation members 86 can extend proximally beyond the proximal end portions 108 of the release members 106 and through an axially extending bore or opening 178 formed in the proximal end portion 180 of the handle 70. The actuation members 86 can be selectively secured relative to the handle 70 using a clamping, or retaining, mechanism 182. The retaining mechanism 182 can comprise a plug member 184, a screw member 186 connected at one end of the plug member 184, and knob 188 connected to the opposite end of the screw member 186. The plug member 184 can be positioned in a radially bore 184 formed in the proximal end portion 180 of the handle 70. The plug member 184 can include a triangular or trapezoidal lower surface that can be placed in, and removed from, contact with a corresponding shaped surface 192 of the radial bore 190. In other implementations, the plug member 184 can have a different shape. The screw member 186 extends through a captured nut 194 such that rotation of the knob 188 causes the plug member 184 to move toward or away from the surface 192 of the radial bore 190.

When the knob 188 is fully tightened (such as by rotating the knob 188 in a first direction), the lower surface of the plug member 184 can clamp the actuation members 86 against the surface 192, thereby securing the actuation members 86 against movement relative to the handle 70, the shaft 72, the locking units 94, and the frame 22 of the prosthetic valve. When the knob 190 is rotated in the opposite direction, the plug member 184 can move away from the surface 192 and the actuation members 86, allowing the actuation members to move relative to the handle 70, the shaft 72, the locking units 94, and the frame 22 of the prosthetic valve.

To use the delivery apparatus 18 to delivery and implant the prosthetic valve 14 at a desired location within the heart (e.g., the native aortic valve), the prosthetic valve 14 is connected to the positioning members 76 using the locking units 94 and the release members 106, as shown in FIGS. 8 and 9. The release knob 168 is retained relative to the lead screw 144 to prevent relative movement between the positioning members 76 and the release members 106. The prosthetic valve 14 can then be radially compressed or crimped to a compressed state, as shown in FIG. 7. The compressed prosthetic valve 14 can be loaded into the sheath 82 of the shaft 72.

Conventional techniques and devices can be used to insert and advance the delivery apparatus 18 and the prosthetic valve 14 through a patient's vasculature to the desired implantation site. For example, a prosthetic aortic valve can be delivered in a retrograde approach by advancing the delivery apparatus through a femoral artery and the aorta to the native aortic valve. At or adjacent the implantation site, the prosthetic valve 14 can be deployed from the sheath 82 by rotating the actuator nut 148 in a direction to cause the lead screw 144 to move distally relative to the handle 70. This causes the positioning members 76 and the release members 106 to move distally relative to the shaft 72. The positioning members 76 push the prosthetic valve 14 distally relative to the shaft 72. The actuator nut 148 can be rotated until the prosthetic valve is deployed from the distal end of the sheath 82. In some implementations, the inherent resiliently of the frame 22 may cause the prosthetic valve to at least partially expand when advanced from the sheath 82.

As the prosthetic valve 14 is deployed from the sheath 82, the retaining mechanism 182 can be in a release position allowing the actuation members 86 to move distally with the prosthetic valve. In this manner, the actuation members 86 do not apply any expansion forces to the prosthetic valve as it is being deployed from the sheath. To apply an expansion force to the prosthetic valve, the retaining mechanism 182 is tightened to retain the actuation members 86 relative to the handle 70. Continued rotation of the actuator nut 148 causes the positioning members 76 to continue to apply a distally directed force on the proximal end of the frame 22 while the actuation members 86 (which are now restrained by the retaining mechanism 182) become taught and apply a proximally directed force on the distal end of the frame 22. The application of these forces causes the frame 22 to foreshorten axially and expand radially.

In some embodiments, the retaining mechanism 182 can be kept in the locked or engaged position against the actuation members 86 during valve deployment so long as the actuation members are long enough and contain enough slack to avoid applying any expansion force on the prosthetic valve as it is advanced from the sheath 82. For example, the lengths of the actuation members 86 can be selected to avoid applying any expansion force on the prosthetic valve as it is advanced from the sheath 82 and after the prosthetic valve is fully deployed from the sheath, the actuation members 86 become taught and begin to apply an expansion force on the frame opposite the expansion force of the positioning members 76 to expand the prosthetic valve.

If re-positioning or complete withdrawal of the prosthetic valve from the body is required, the user can rotate the actuator nut 148 in the opposite direction, which causes the positioning members 76 to pull the prosthetic valve back into the sheath 82. The action of the distal end portions 110 of the positioning members 76 being retracted into the sheath 82 causes the prosthetic valve to compress radially. If desired or needed, the prosthetic valve can be partially compressed without being retracted into the sheath and then re-positioned and re-expanded by rotating the actuator nut 148. In some cases, the prosthetic valve can be completely retracted back into the sheath 82 for re-positioning or complete withdrawal of the prosthetic valve from the body.

Once the prosthetic valve is expanded and positioned at the desired location, the release members 106 can be retracted from the locking units 94. This can be accomplished by releasing the release knob 168 from the lead screw 144 and retracting the release knob 168 proximally, which causes the release members 106 to retract relative to the locking units 94. When the distal ends of the release members 106 are proximal to the jaws 102 of the clamping mechanism 98, the jaws can engage the actuation members 86 to retain the prosthetic valve in the expanded state. Further retraction of the release members 106 past the tabs 122 of the locking units 94 allows the positioning members 76 to be released from the locking units. Retraction of the positioning members 76 by rotation of the actuator nut 148 or retracting the handle 70 causes the distal end portions 110 of the positioning members to pull free of the locking units 94. As discussed above, the portions of the actuation members 86 proximal to the clamping mechanisms 98 can be severed and removed from the body. Thereafter, the delivery apparatus can be withdrawn from the body.

Figure 12A:
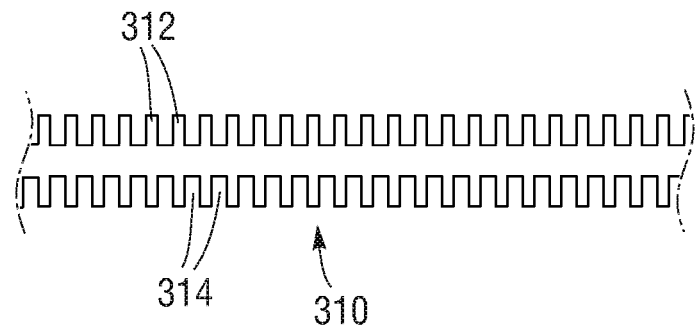
FIG. 12A is a schematic diagram of an actuation member having locking features that can be used with the prosthetic valve delivery assembly of FIG. 1, according to one embodiment.
Figure 12B:
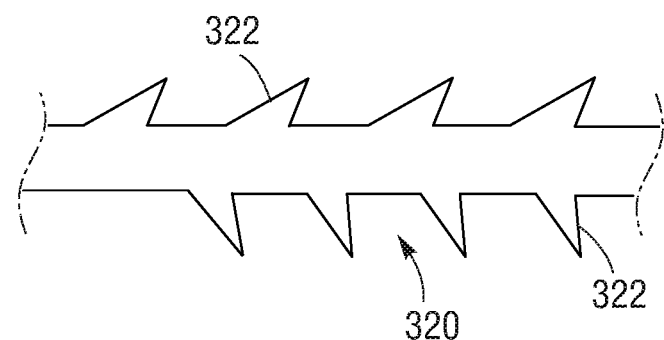
FIG. 12B is a schematic diagram of another embodiment of an actuation member having locking features that can be used with the prosthetic valve delivery assembly of FIG. 1.
Figure 12C:
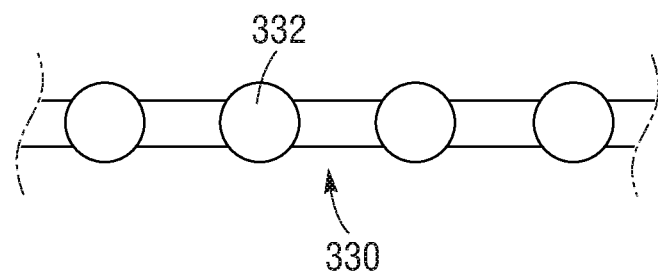
FIG. 12C is a schematic diagram of another embodiment of an actuation member having locking features that can be used with the prosthetic valve delivery assembly of FIG. 1.

In alternative embodiments, the distal end portions of the actuation members 86 can have locking features to promote locking engagement of the jaws 102 of the clamping mechanism 98 with the actuation members 86. FIGS. 12A, 12B, and 12C, for example, show actuation members 310, 320, 330, respectively, that can be used with the locking unit 94 of FIG. 9. With reference to FIG. 12A, the actuation member 310 can include locking features in the form of a plurality of spaced-apart ribs or projections 312 and slots 314 between adjacent ribs. The jaws 102 of the clamp 98 can extend into the slots 314, helping secure the actuation member 86 against movement relative to the clamp 98 in a direction opposite the tension being applied to the actuation member by the user. In other words, the actuation member 86 and the clamp 98 can function as a ratchet that allows the actuation member 86 to be pulled through the clamp 98 in a first direction to expand the frame 22 but the engagement of the jaws 102 in the slots 314 resist movement of the actuation member 86 in a second, opposite direction.

As shown in FIG. 12B, an actuation member 320 can include a plurality of spaced-apart angled barbs 322 that can engage the jaws 102 of the clamp 98. With reference to FIG. 12C, an actuation member 330 can include a plurality of spaced-apart spherical protrusions 332, such as beads, that can engage the jaws 102 of the clamp 98. The barbs 322 and the protrusions 332, like the ribs 312, allow movement of the actuation member through the jaws 102 in a first direction but resist movement in a second, opposite direction.

FIGS. 14, 15, and 16A-16D illustrate an alternative release-and-locking unit 410 that can be used with a prosthetic implant delivery assembly, including, for example, the prosthetic implant delivery assembly 10 of FIG. 1. The locking unit 410 can be incorporated in any radially expandable frame of a prosthetic valve or other type of prosthetic implant, including, for example, the frame 22 of FIG. 2 or the frame 200 of FIG. 4.

With reference to FIG. 14, the locking unit 410 can be coupled to a frame 412. The frame 412 can have a construction similar to the frame 200. One or more locking units 410 can be coupled to the frame 412 at circumferentially spaced apart locations, similar to the locking units 94 described above. In particular embodiments, the frame 412 can have three such locking units 412 coupled to the frame, in the manner shown in FIG. 1 with respect to the locking units 94.

The locking unit 410 generally can comprise an inner member 416, such an inner tubular member, and an outer member 418, such as an outer tubular member, concentrically disposed about the inner member 416. The inner member 416 and the outer member can be moveable longitudinally relative to each other in a telescoping manner to radially expand and contract the frame 412, as further described below. As best shown in FIGS. 14 and 16A, the inner member 416 can have a distal end portion 420 coupled to a distal end 422 of the frame 412 with a coupling element 424. The outer member 418 can have a proximal end portion 426 coupled to a proximal end 428 of the frame 412 with a respective coupling element 424.

The inner member 416 and the outer member 418 can telescope relative to each other between a fully contracted state (as shown in FIG. 15) corresponding to a fully radially expanded state of the prosthetic valve and a fully extended state (wherein the inner member 416 is fully extended from the outer member 418) corresponding to a fully radially compressed state of the prosthetic valve. The locking unit 410 allows the prosthetic valve to be fully expanded or partially expanded to different diameters and retains the prosthetic valve in the partially or fully expanded state.

Each of the coupling elements 424 desirably is connected to a respective apex 430 at the proximal or distal end of the frame. Each apex 430 can be formed by the adjacent end portions of two struts 432 that are pivotably connected to each other with a fastener 434 (e.g., a rivet or pin) that extends through corresponding apertures in the struts. Each coupling element 424 can be pivotably connected to a respective apex 430 by a corresponding fastener 434 that extends into an opening or bore 436 (FIG. 16A) of the coupling element 424. The fastener 434 in the illustrated embodiment therefore connects the end portions of the struts 432 to a coupling element 424 while allowing the struts to pivot relative to each other and the coupling element 424.

In alternative embodiments, the end portions of the struts 432 can be secured to each other and the coupling element without a pinned connection. For example, the frame can be laser cut from a metal tube without pinned connections at each apex and the coupling elements or the end portions of the inner and outer members 416, 418 can be connected to the frame at or adjacent respective apices, such as by welding or sutures.

As further shown in FIG. 16A, a proximal end portion 438 of the inner member 416 can be releasably coupled to an inner actuation member, or shaft, 440 that extends the length of the delivery apparatus to a handle at the proximal end of the delivery apparatus (the handle is not shown but can be similar to the handle 70 of FIG. 1). The proximal end portion 426 of the outer member 418 can be releasably coupled to an outer actuation member, or shaft, 442 that extends the length of the delivery apparatus to the handle at the proximal end of the delivery apparatus. The proximal end portions of the inner actuation member 440 and the outer actuation member 442 can be operatively connected to respective actuators or control mechanisms (e.g., rotatable or slidable knobs) in the handle to effect longitudinal movement of the actuation members 440, 442 relative to each other. The inner actuation member 440 can extend coaxially through the outer actuation member 442. The pair of inner and outer actuation members 440, 442 can extend through an outer shaft (not shown, but can be similar to the shaft 72 of FIG. 1) along with other pairs of inner and outer actuation members extending from the other locking units 410. All pairs of inner and outer actuation members 440, 442 can be operatively connected to a common actuator or control mechanism on the handle.

The inner and outer actuation members 440, 442, respectively, are configured to apply proximally and distally directed forces to the inner and outer members 416, 418, respectively, to effect radial expansion and contraction of the frame 412. For example, to expand the frame, the outer actuation member 442 can be moved distally while the inner actuation member 440 is held stationary, thereby causing the outer member 418 to move distally over the inner member 416. As a result, a distally directed force is applied to the proximal end 428 of the frame 412, causing the frame to foreshorten axially and expand radially. Expansion of the frame 412 can also be accomplished by moving the inner actuation member 440 proximally while the outer actuation member 442 is held stationary. Alternatively, the frame 412 can be expanded by moving the inner actuation member 440 proximally and simultaneously moving the outer actuation member 442 distally. The frame 412 can be radially contracted by reversing the direction of movement of the inner and outer actuation members 440, 442.

A release member 444 can extend coaxially between the inner actuation member 440 and the outer actuation ember 442 along the length of the delivery apparatus. A distal end portion 446 of the release member 444 can extend coaxially between the inner member 416 and the outer member 418 of the locking unit 410. The proximal end portion of the release member 444 (not shown) can be operatively connected to a corresponding actuator or control mechanism (e.g., a rotatable or slidable knob) on the handle to effect longitudinal movement of the release member relative to the inner and outer actuation members 440, 442. The locking unit 410 can include a centering tube 448 coaxially disposed between the inner member 416 and the outer member 418 distal to the release member 444. The centering tube 448 helps maintain the outer member 418 in coaxial alignment with respect to the inner member 416 and can be secured, such as by welding, to the outer member 418. The proximal end portions of release members 444 extending from all locking units 410 on the frame can be operatively connected to a common actuator or control mechanism on the handle.

As noted above, the proximal end portion 426 of the outer member 418 can be releasably coupled to the outer actuation member 442. As best shown in FIG. 15, the releasable coupling can be formed by, for example, a notch 454 and a tab 456 formed in the proximal end portion 426 of the outer member 418 and configured to releasably engage a corresponding tab 458 and a notch 460 of the outer actuation member 442. During delivery and expansion of the prosthetic valve, the release member 444 extends through the notches 454, 460 and tabs 456, 458, and can prevent the tab 456 from disengaging from the notch 460, and the tab 458 from disengaging from the notch 454, similar to the tabs 114, 120 and notches 116, 120 of FIG. 10A. When the prosthetic valve is to be released from the delivery apparatus, the release member 444 can be moved proximally of the notches 454, 460 and tabs 456, 458, allowing them to disengage and the outer member 418 and the outer actuation member 442 to disengage and decouple from each other.

The proximal end portion 438 of the inner member 416 can be releasably coupled to the inner actuation member 440 in a similar fashion. For example, the inner member 416 can be coupled to the inner actuation member 440 using a notch 462 and a tab 464 formed in the proximal end portion 438 of the inner member 416 and configured to releasably engage a corresponding tab 466 and a notch 468 of the inner actuation member 440. During implantation and expansion, the release member 444 can extend coaxially over the notches 462, 468 and tabs 464, 466, preventing the inner member 416 and the inner actuation member 440 decoupling. When the prosthetic valve is to be released from the delivery apparatus, the release member 444 can be moved proximally of the notches 462, 468 and tabs 464, 466, allowing them to disengage and the inner member 416 and the inner actuation member 440 to disengage and decouple from each other.

The inner and outer members 416, 418 can include corresponding locking features to retain the frame 412 in an expanded state. In the illustrated embodiment, for example, the inner member 416 can include one or more longitudinally spaced apart apertures or recesses 470 disposed along the length of the inner member 416. The apertures 470 can be configured to receive a locking member 472 of the outer member 418. The locking member 472 can have a fixed end portion 474 secured to the outer member 418, a tapered or reduced-diameter intermediate portion 476, and a free end portion, or latch portion, 478 configured to engage one of the recesses 470.

The locking member 472 can biased radially inwardly toward the inner member 416, such as by shape setting the locking member 472 to bend inwardly toward the inner member. In certain embodiments, for example, the locking member 472 (and, optionally, the entire outer member 422) can be formed from a shape-memory alloy, such as a nickel titanium alloy ("NiTi"), for example Nitinol. When the release member 444 is disposed between the inner member 416 and the outer member 418 during delivery and expansion of the prosthetic valve, the locking member 472 is retained in an unlocked state with the latch portion 478 spaced radially outward of the recesses 470 in the inner member 416 (as best shown in FIG. 16B). When the release member 444 is moved proximally beyond the locking member 472, the locking member 472 can assume its pre-bent shape, indicated by position 480, and the latch portion 478 can extend into a selected recess 470 (as best shown in FIG. 16D). Once the latch portion 478 has entered a recess 470, the inner member 416 and outer member 418 can be secured against relative axial movement thereby resisting radial contraction of the frame from its expanded state.

A rigid sleeve 490 can be mounted over the outer member 418 adjacent the locking member 472 to resist buckling of the locking unit 410 in the area of the locking member 472. The rigid sleeve 490 can be at least generally annular and extend around at least a portion of the outer surface of the outer member 418. In some examples, the rigid sleeve 490 can extend fully about the outer surface of the outer member 418. In other examples, the rigid sleeve 490 can extend for less than the entire outer surface of the outer member 418. In some cases, the rigid sleeve 490 can be fixedly secured to the outer member 418, such as by adhesion or welding.

In use, the prosthetic valve incorporating the frame 412 and locking units 410 can be placed in a compressed state in a sheath of a delivery apparatus, as discussed above in connection with the prosthetic valve 14. A physician can then insert the prosthetic valve into a patient. When the prosthetic valve is at the desired location within the patient, the physician can deploy the prosthetic valve from the sheath and then expand or contract the frame 412 to achieve a desired frame size (diameter) by manipulating the inner and outer actuation members 440, 442, as described above. The prosthetic valve can be deployed from the sheath by retracting the sheath and/or by advancing the inner and outer actuation members in the distal direction to advance from the prosthetic valve from the sheath.

In particular embodiments, the prosthetic valve is fully functional once deployed from the sheath and at least partially expanded. In this manner, the physician can test the operation of the prosthetic valve prior to releasing the prosthetic valve from the delivery apparatus. If needed or desired, the prosthetic valve can be at least partially radially compressed, repositioned (e.g., repositioned superiorly or inferiorly) and then re-expanded. If needed or desired, the prosthetic valve can be fully radially compressed and retrieved back into the sheath of the delivery apparatus and withdrawn from the body.

When the desired size and position of the prosthetic valve has been achieved, the physician can proximally retract the release member 444 until it is located proximal to the locking member 472. The locking member 472 can then assume its pre-curved shape and engage an aperture 470 in the inner member 416 of the locking unit, thereby resisting further relative movement between the inner member 416 and the outer member 418 and retaining the prosthetic valve in its expanded state. As noted above, the handle of the delivery apparatus can include common actuator that controls retraction of all release members 444 extending from corresponding locking units 410 on the frame in embodiments that include plural locking units.

To release the prosthetic valve from the delivery apparatus, the physician can further retract the release member 444 until it is located proximal to the notches 462, 468 and the tabs 464, 466 to de-couple the inner member 416 from the inner actuation member 440 and proximal to the notches 454, 460 and the tabs 458, 456 to de-couple the outer member 418 from the outer actuation member 442. Thereafter, the delivery apparatus can be withdrawn from the body.

It should be appreciated that the locking units 410 and delivery apparatus used therewith may be modified without departing from the scope of the present disclosure. For example, in some implementations, the outer member 418 can be axially moveable relative to a fixed inner member 416, in further implementations the inner member 416 can be axially moveable relative to a fixed outer member 416, and in yet other implementations the inner member 416 and the outer member 418 may both be axially moveable relative to one another. Although the inner member 416 is depicted and described as connected to a distal end 422 of the frame 412, in other implementations the position of the locking unit can be reversed such that the inner member 416 can be connected to the proximal end 428 of the frame 412, and the outer member 418 connected to the distal end 422 of the frame 412.

Similarly, the inner member 416 is described as having apertures 470 and the outer member as having a locking member 472. However, in other implementations, the locking member 472 can be included on the inner member 416 and the apertures 470 can be formed in the outer member 422. Although depicted and described as tubular, the inner member 416, the outer member 418, and the release member 444 can have other shapes or configurations. For example, in one particular implementation, the inner member 416, the outer member 418, and the release member 444 can be formed from flat strips of material, with one of the inner member 416 and the outer member 418 having the apertures 470 and the other having the locking member 472. The flat strips forming the inner member 416, the outer member 418, and the release member 444 can be housed in an elongated housing, such as a shaft or tubular member.

The frames and/or delivery assemblies of the present disclosure can provide a number of advantages. For example, a mechanically expandable frame as described herein can be radially compressed to a delivery configuration and loaded into a delivery apparatus without using a crimping apparatus. Because the frame can be fully expanded or expanded to a desired size less than the fully expanded state, at least in some embodiments, a prosthetic valve as described herein can be implanted in various size annuluses, and the optimal size of the prosthetic valve can be achieved during implantation. In some cases, a delivery assembly of the present disclosure can apply a sufficient expansion force to open or enlarge a calcified native valve, which can reduce or eliminate the need for pre- or post-balloon valvuloplasty.

In addition, as noted above, the prosthetic valve can be fully functional during the implantation procedure, which can reduce or prevent blood flow occlusion and avoid the use of rapid pacing during implantation. The embodiments disclosed herein also can allow for slow deployment of the prosthetic valve, which can allow for tissue stress relaxation, and can reduce the risk of aortic rupture.

Figure 17A:
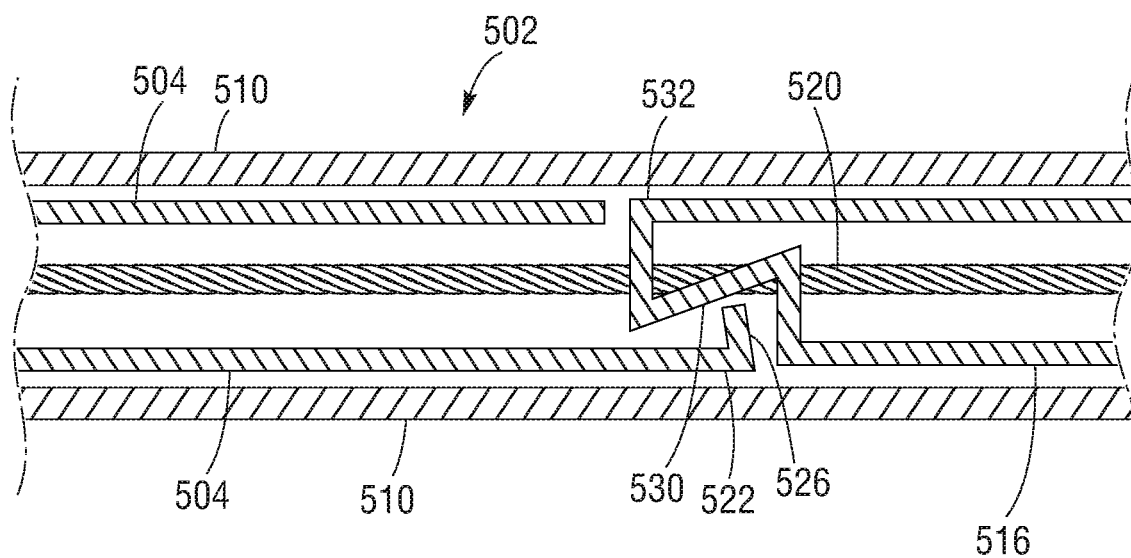
FIG. 17A is an enlarged cross-sectional view of a portion of a locking unit that can be used with the prosthetic valve delivery assembly of FIG. 1, according to one embodiment, showing the locking unit portion in a locked configuration.
Figure 17B:
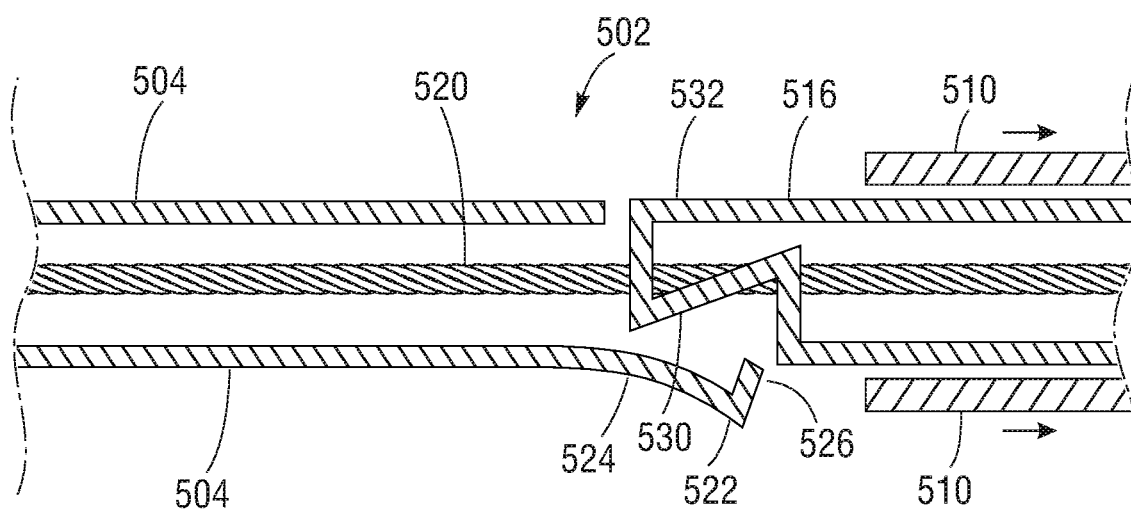
FIG. 17B is an enlarged cross-sectional view of the locking unit of FIG. 17A, showing the locking unit in a release configuration.

FIGS. 17A and 17B illustrate a proximal portion of an alternative release-and-locking unit 502 ("locking unit") that can be used in embodiments of the present disclosure, such as with the delivery apparatus 18 of FIG. 1, to release a prosthetic valve from a delivery apparatus and/or lock the prosthetic valve in its expanded state. One or more such units 502 can be mounted on the frame of a prosthetic valve at circumferentially spaced apart locations.

In some implementations, a distal portion of the locking unit 502, (not shown; the distal portion being to the left of the portion shown in FIGS. 17A and 17B), can be at least generally similar to a distal portion of the locking unit 94 of FIGS. 8, 9, 10A, 10B, and 11, and can including a locking feature, such as the clamp 98, and the aperture 132 for receiving the fastener 130 for securing the locking unit 504 to a valve frame. In further implementations, a distal portion of the locking unit 502 can be at least generally similar to a distal portion of the locking unit 410 of FIGS. 14, 15, and 16A-16D.

The locking unit 502 can have an elongate, inner body or shaft 504 (e.g., a generally cylindrical tube or shaft), which can be disposed within a lumen of a release member 510. A positioning member 516 can also be disposed within the lumen of the release member 510. The inner body 504 can be secured to the frame of the prosthetic valve. In some embodiments, the unit 502 can function solely as a release unit to release the prosthetic valve from the delivery apparatus, in which case the prosthetic valve can have another mechanism for locking the frame of the prosthetic valve in its expanded state.

The release member 510 and the positioning member 516 can be at least generally similar to, respectively, the release member 106 of FIG. 9, or the release member 444 of FIG. 16C, and the positioning member 76 of FIG. 1. In at least certain embodiments, such as when the locking unit 502 includes a distal portion similar to that of the locking unit 94, the locking unit can include an actuation member 520, which can be at least generally similar to the actuation member 86 of FIG. 8. The actuation member 520 can be disposed within a lumen of the body 504 of the locking unit 502 and a lumen of the positioning member 516. In other embodiments, such as when the locking unit 502 includes a distal portion similar to that of the locking unit 410, the actuation member 520 can be omitted.

A proximal end portion 522 of the body 504 of the locking unit 502 can comprise a radially-inwardly extending fin, or in-turned lip portion 526. The fin 526 can be negatively angled, that is, the fin 526 is angled distally toward the prosthetic valve (to the left in the drawings). The fin 526 can be configured to abut or extend into an angled notch or recessed portion 530 formed in a distal end portion 532 of the positioning member 516. The fin 526 and an extension portion 524 of the body 504 adjacent the fin can incorporate a preset bend, such that they are biased radially outwardly. For example, the locking unit 502, or at least the fin 526 and the extension portion 524, can be formed from a shape-memory alloy, such as a nickel titanium alloy ("NiTi"), for example Nitinol.

The body 504 and the fin 526 can be heat set to provide a desired degree of bending. When positioned within the release member 510, the fin 526 and the extension portion 524 are radially constrained, and the fin is held in contact with the notch 530. By virtue of the diameter or width of the notch 530 increasing in a distal direction along the length of the positioning member 516, and the fin 526 being negatively angled, the fin and notch can engage each other to prevent axial separation of the positioning member 516 from the inner body 504, thereby maintaining the connection between the prosthetic valve and the delivery apparatus. When the prosthetic valve is to be released from the delivery apparatus (e.g., the delivery apparatus 18), such as after being deployed within a patient's heart, the release member 510 can be retracted proximally, as shown in FIG. 17B. No longer being constrained by the release member 510, the fin 526 and the extension portion 524 the body 504 of the locking unit 502 can assume their preset shape, deflecting radially outwardly, thus disengaging the fin from the notch 530. With the fin 526 released from the notch 530, the locking unit 502 and the positioning member 516 can decouple, thereby releasing the prosthetic valve from the delivery apparatus and allowing the delivery apparatus to be removed from the patient.

Figure 18:
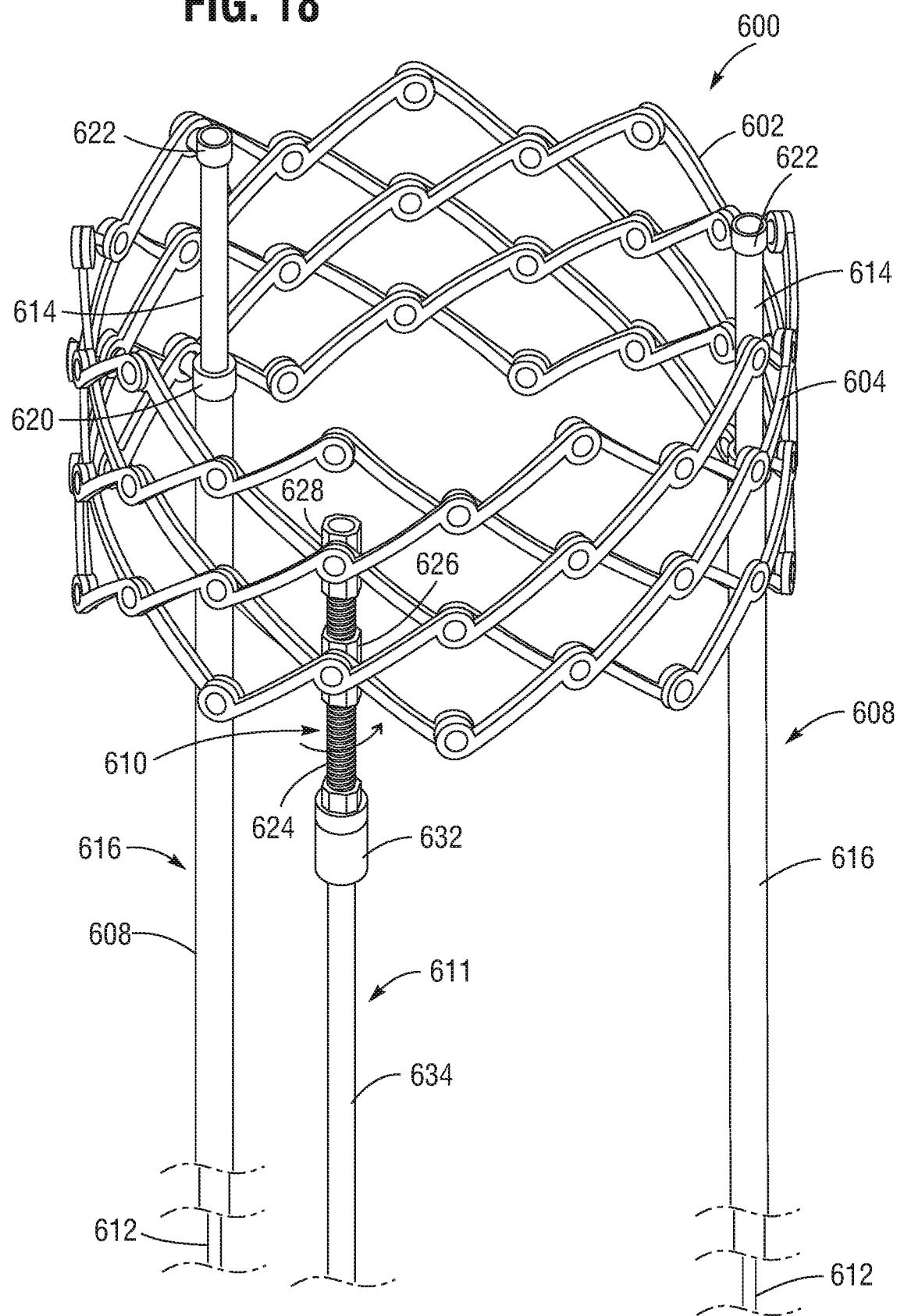
FIG. 18 shows the distal end of another exemplary prosthetic valve delivery system.

FIG. 18 shows an alternative embodiment of a prosthetic valve delivery assembly 600. The delivery assembly 600 can include a prosthetic valve 602. The prosthetic valve 602 can include a radially expandable and collapsible frame 604 and a valvular structure 606 supported inside the frame (FIGS. 19A and 19B). The frame 604 can be constructed in a manner similar to the frame 22 of FIG. 2 and can be formed from a plurality of interconnected struts similar to struts 32. The valvular structure can be constructed in a manner similar to the valvular structure 24 of FIG. 2.

The delivery assembly 600 can further include one or more linear actuator assemblies 608 and one or more locking mechanisms 610 secured to the frame 602. The one or more linear actuator assemblies 608 are configured to radially expand and compress the frame 604 and the one or more locking mechanisms 610 are configured to lock or retain the frame 604 in a particular radially expanded state as explained in more detail below. The delivery assembly 600 can further include one or more locking tools 611 configured to advance the one or more locking mechanisms 610 into a position to lock the frame 604 as explained in more detail below.

In the illustrated embodiment of FIG. 18, the delivery assembly 600 includes two linear actuator assemblies 608 and one locking mechanism 610. FIG. 19A shows an embodiment of the delivery assembly 600 having two linear actuator assemblies 608 and one locking mechanism 610. FIG. 19B shows an alternative embodiment of a prosthetic valve delivery assembly 600' that is the same as delivery assembly 600 except that delivery assembly 600' has one linear actuator assembly 608 and two locking mechanisms 610. In other embodiments, a prosthetic delivery assembly can have any number of linear actuator assemblies and/or locking mechanisms.

The delivery assembly 600 can be used to percutaneously implant the prosthetic valve 602 into a patient's vasculature to a desired implantation site, such as the native aortic valve. During implantation, the frame 604 is in a radially collapsed state, similar to the frame 200 of FIG. 2. Once the prosthetic valve prosthetic valve 602 reaches the desired implantation site, the one or more linear actuator assemblies 608 can be used to radially expand the frame 604. Once the frame 604 is expanded to a desired radially expanded size, the one or more locking tools 611 can be used to position the one or more locking mechanisms 610 to lock the frame 604 at that radially expanded size such that the frame 604 is prevented from further radial expansion and/or contraction. The one or more linear actuator assemblies 608 and the one or more locking tools 611 can then be disconnected from the prosthetic valve 602 such that the frame 604 remains locked in a radially expanded state and the disconnected portion of the delivery assembly 600 can be removed from the patient. The operation of the linear actuator assemblies 608, the locking mechanisms 610, and the locking tools 611 are described more fully below.

FIG. 23A shows a linear actuator assembly 608 in the process of being disconnected from the frame 604 after the frame has been radially expanded. Referring to FIG. 23A, the linear actuator assembly 608 can include an inner actuator member 612 (which can also be referred to as an actuation member), a cover tube 614 extending co-axially over the actuator member 612, a support tube or pusher member 616 extending co-axially over the cover tube 614, a threaded screw 618, and a stopper 620 fixedly mounted on the frame 604. FIG. 23B shows a perspective view of the linear actuator assembly 608 without the support tube 616. The actuator member 612 can be, for example, a rod, cable, or wire. The actuator member 612 can be connected at its distal end to the threaded screw 618 such that rotation of the actuator member 612 causes rotation of the threaded screw 618. The proximal end of the actuator member 612 can be connected to a handle or other control device (not shown) that a doctor or operator of the delivery assembly 600 can use to rotate the actuator member 612. Similarly, the proximal ends of each cover tube 614 and each support tube 616 can be connected to the handle.

The screw 618 has an externally threaded surface that can engage an internally threaded surface of a nut or sleeve 622, which is affixed to the frame 604, such as at the distal end of the frame. In the present disclosure, a "nut" is sometimes used generically to refer to a sleeve that does not necessarily have internal threads. Thus, reference to a nut does not necessarily require internal threads unless the context dictates otherwise. When the actuator member 612 is rotated to screw the screw 618 into the nut 622, the actuator member 612 becomes connected to the distal end of the frame 604 such that proximal or distal motion of the actuator member 612 causes proximal or distal motion, respectively, of the distal end of the frame 604.

The cover tube 614 annularly surrounds the actuator member 612. The cover tube 614 can be connected to the actuator member 612 such that the actuator member 612 and the cover tube 614 rotate together and move axially together. The actuator member 612 and the cover tube 614 extend through the stopper 620, which can be affixed to a proximal end of the frame. The support tube 616 annularly surrounds the cover tube 614. The stopper 620 has an annular inner surface with an inner diameter larger than the outer diameter of the cover tube 614 and the screw 618 such that the cover tube 614 and the screw 618 can be retracted through the stopper 620 as the frame 604 is expanded and once the actuator is disconnected from the frame, as further discussed below. The stopper 620 is sized to abut or engage the distal end of the support tube 616 such that the support tube 616 is prevented from moving distally beyond the stopper 620.

In operation, prior to implantation in a patient, the screw 618 is threaded into the actuator nut 622, thereby connecting the linear actuator assembly 608 to the frame 604. The frame 604 can then be placed in a radially collapsed state and the delivery assembly 600 can be inserted in a patient. Once the prosthetic valve 602 is at a desired implantation site, the frame 604 can be radially expanded as described herein.

To radially expand the frame 604, the support tube 616 is held firmly against the stopper 620. The actuator member 612 is then pulled in a proximal direction through the support tube 616, such as by pulling on the proximal end of the actuator member 612 or actuating a control knob on the handle that produces proximal movement of the actuator member 612. Because the support tube 616 is being held against the stopper 620, which is connected to the proximal end of the frame 604, the proximal end of the frame 604 is prevented from moving relative to the support tube 616 and the handle. As such, movement of the actuator member 612 in a proximal direction results in movement of the distal end of the frame 604 in a proximal direction causing the frame 604 to foreshorten axially and expand radially. FIG. 20A shows the frame 604 in a partially expanded state, while FIG. 20B shows the frame 604 in a further expanded state when a proximally directed force is applied to the distal end of the frame 604 while the proximal end of the frame 604 is held in place. In the illustrated embodiment, there is a one-to-one ratio between axial movement of the actuator member 612 and the increase in the diameter of the frame 604, which allows for stable and controlled expansion of the frame.

It should be understood that the frame 604 can also be radially expanded by pushing the proximal end of the frame toward the distal end of the frame by pushing the support tube 616 against the stopper 620 while keeping the actuator member 612 stationary relative to the handle, or alternatively, by simultaneously pushing the support tube 616 distally against the stopper 620 and pulling the actuator member 612 proximally.

Figure 21:
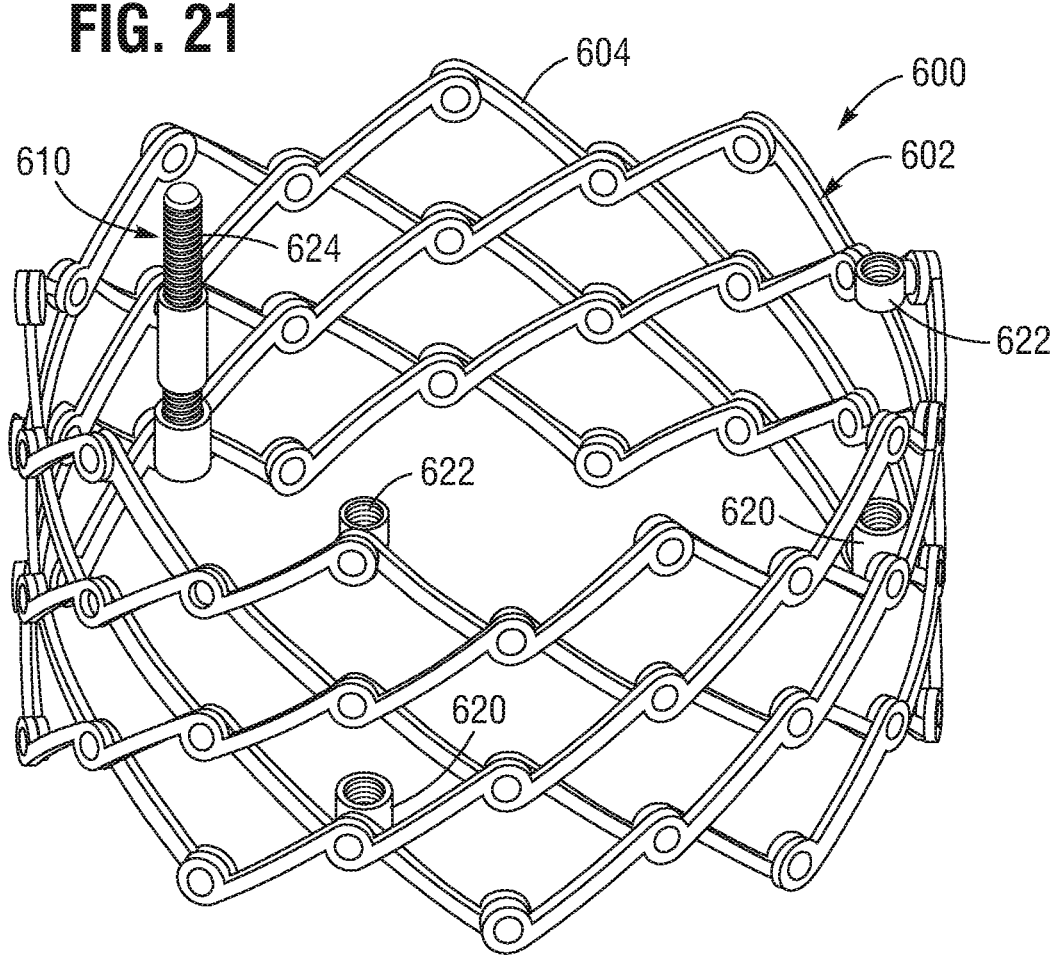
FIG. 21 shows a portion of the delivery system of FIG. 18 with expansion members removed.

After the frame 604 is expanded to a desired radially expanded size, the locking mechanism 610 can be actuated to lock the frame 604 in the desired radially expanded size, as discussed in further detail below, and the linear actuator assembly 608 can be disconnected from the frame 604 as described herein. To disconnect the linear actuator assembly 608 from the frame 604, the actuator member 612 can be rotated so as to unscrew the screw 618 from the nut 622. The actuator member 612 and the cover tube 614 can then be retracted proximally through the stopper 620 and the linear actuator assembly 608 (including the actuator member 612, the screw 618, the cover tube 614, and the support tube 616) can be withdrawn from the patient. The cover tube 614 facilitates passage of the screw 618 through the stopper 620. FIG. 21 shows the delivery assembly 600 after the linear actuator assemblies 608 have been removed. In embodiments that have more than one linear actuator assembly 608, the above procedure for expanding the frame 604 is performed for each linear actuator assembly 608.

Locking the frame 604 at a particular radially expanded state can be achieved using the locking mechanism 610 and the locking tool 611. Referring to FIG. 18 and FIGS. 24A-24D, the locking mechanism 610 can include a locking screw 624 having an externally threaded surface. The locking mechanism 610 can further include a proximal sleeve or nut 626 (also referred to as a "proximal sleeve member") and a distal sleeve or nut 628 (also referred to as a "distal sleeve member") connected to the frame 604 at axially spaced apart locations. The proximal nut 626 can be connected to a proximal end of the frame 604 and the distal nut 628 can be connected to the frame 604 at a location axially aligned and distally spaced from the proximal nut 626. The distal nut 628 can have internal threads that can engage the external threads of the locking screw 624 to connect the locking screw 624 to the frame 604 and prevent radial contraction of the frame 604, as explained below. The proximal nut 626 can be sized such that the locking screw 624 can slide freely within a lumen of the proximal nut. In alternative embodiments, the proximal nut 626 can have internal threads that can engage the external threads of the locking screw 624 to connect the locking screw 624 to the frame 604.

The locking screw 624 can have a screw head 630 at its proximal end having, for example, a square or rectangular shape. The screw head 630 can be sized such that the screw head cannot advance distally beyond the proximal nut 626. The locking tool 611 can be configured to operate the screw 624 after the prosthetic valve is expanded to a desired size via the liner actuators. The tool 611 can comprise an elongated shaft 634 and a tool head 632 connected to the distal end of the shaft 634. The proximal end of the shaft 634 (not shown) can be connected to the handle of the delivery assembly 600, which can have an actuator (e.g., a knob on the handle) configured to rotate the shaft upon actuation by a user. The shaft 634 can comprise, for example, a rod or cable that has sufficient torsional rigidity to transfer torque from the proximal end of the shaft to the tool head 632.

The tool head 632 can have a square or rectangular opening 633 corresponding to the shape of the screw head 630 such that the screw head 630 can be received within the tool head 632. When the screw head 630 is received within the tool head 632, rotation of the tool head 632 causes rotation of the screw head 630. In alternative embodiments, the screw head 630 and the opening of the tool head 632 can have various other non-circular shapes that allow the tool head 632 to rotate the screw head 630 when the tool head engages the screw head.

Referring to FIGS. 25B-25C, the shaft 634 can comprise an outer shaft and the tool 632 can further comprise an inner shaft 636 (e.g., a rod or cable) that extends coaxially through the outer shaft 634. A distal end portion of the inner shaft 636 extends into the tool head 632 and mounts an attachment member 638 configured to form a releasable connection with the screw head 630. In the illustrated embodiment, for example, the attachment member 638 comprises external threads 640 that are configured to engage internal threads 642 of an annular bore formed in the screw head 630 so as to connect the inner shaft 636 to the screw head 630. The inner shaft 636 can extend proximally to a handle or other device that a doctor or other operator of the delivery assembly 600 can use to rotate the inner shaft 636. The inner shaft 636 can be rotated independently of the outer shaft 634 and the tool head 632.

Prior to implantation, the tool 611 can be attached to the locking screw 624 by placing the tool head 632 around the screw head 630 as shown in FIG. 25C. The inner shaft 636 is then rotated in a first direction (e.g., in a clockwise direction) to screw the attachment member 638 into the screw head 630 as shown in FIG. 25B. By retaining the inner shaft 636 relative to the outer shaft 634 in the axial direction, the attachment of the attachment member 638 with the screw head 630 maintains the engagement of the tool head 632 with the screw head 630.

The locking screw 624 can be initially positioned within the proximal nut 626 but not threaded into the distal nut 628. This allows the frame to be radially expanded by the linear actuator assemblies 608. The delivery assembly 600 can then be inserted into a patient and the prosthetic valve 602 can be expanded to a desired radial size as described above. In other embodiments, the screw 624 need not be pre-inserted into the nut 626 and instead can be positioned on the frame 604 such that when the screw is rotated, the screw extends into the proximal nut 626 and the distal nut 628. In other embodiments where the proximal nut 626 has internal threads, the screw 624 can be initially threaded into the proximal nut 626 but not the distal nut 628. In other embodiments, the screw 624 need not be pre-mounted on the frame while the prosthetic valve is advanced to the implantation site. For example, the screw 624 can be separately delivered to the prosthetic valve (e.g., using the tool 611) after the prosthetic valve is expanded at the implantation site.

Once the prosthetic valve 602 is radially expanded to a desired size, the outer shaft 634 can be rotated (e.g., in a clockwise direction) to rotate the tool head 632, which in turn rotates the locking screw 624 and advances the distal end portion of the screw 624 through the distal nut 628, as shown in FIG. 24B. The locking screw 624 can be distally advanced such that the screw head 630 abuts the proximal nut 626. When so advanced, the threads of the locking screw 624 engage internal threads of the distal nut 628. With the screw 624 connected to the distal nut 628 and the screw head 630 abutted against the proximal nut 626, the screw is prevented from further distal movement with respect to the frame 604, thereby preventing contraction of the frame 604 from outside forces acting on the frame 604.

However, because the screw 624 can move freely within the proximal nut 626, the proximal end of the screw can move in a proximal direction after the screw is put in a locked position (engaging distal nut 628), thereby allowing additional expansion of the frame 604, either by using the linear actuator assembly 608 as described above or by continuing to rotate the screw 624 after the screw head 630 abuts against the proximal nut 626. This can allow a physician to further expand the frame 604 during implantation of the prosthetic valve 602 after advancing the locking screw 624 to a locked position. This can also allow a physician to expand the frame 604 days, months, or years later following the implantation procedure when implanting a new prosthetic valve within the previously implanted prosthetic valve in a valve-in-valve procedure. If needed, the previously implanted valve can be expanded using a valvuloplasty balloon prior to implanting the new prosthetic valve.

Anatomical forces only apply a compression force on the prosthetic valve 602 once implanted and as such, there is no risk of spontaneous expansion after the valve 602 is locked with the locking screw 624. After additional valve expansion is performed, the locking screw 624 can be rotated to distally advance the screw such that the screw head 630 abuts the proximal nut 626 to again put the screw into a locked position. In embodiments where the proximal nut 626 has internal threads that engage the locking screw 624, any radial contraction and expansion of the prosthetic valve 602 is prevented once the screw is inserted into nuts 626, 628, except from rotation of the screw.

Figure 22:
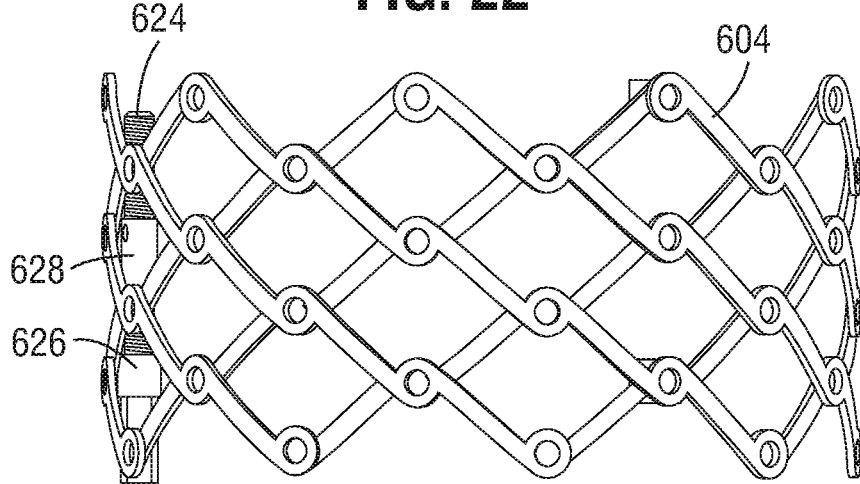
FIG. 22 shows a portion of the delivery system of FIG. 18 with locking members in place.

Once the locking screw 624 is screwed into the distal nut 628 such that the screw head 630 abuts against the proximal nut 626, the inner shaft 636 can be rotated in a second direction (e.g., a counter-clockwise direction), as shown in FIG. 24C, to disconnect the attachment member 638 from the screw head 630, as shown in FIG. 25C. The tool head 632 can then be pulled back and removed from the screw head 630 as shown in FIGS. 24D and 25D so as to disconnect the locking tool 611 from the locking screw 624 on the prosthetic valve. The disconnected locking tool 611 can then be removed from the patient (e.g., when withdrawing the linear actuator assemblies 608 if the linear actuator assemblies and the locking tool are connected to a common handle), leaving the locking screw 624 connected to the frame 604 with the frame 604 locked in a particular radially expanded state as shown in FIG. 22.

Figure 26A:
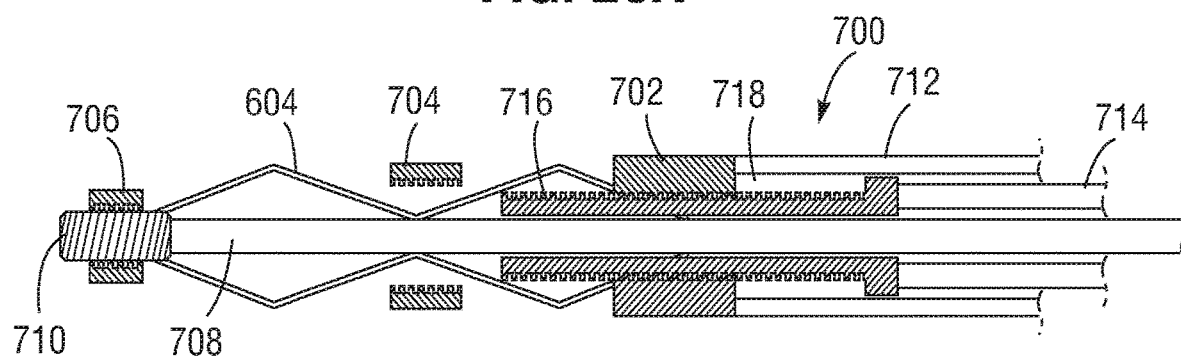
FIG. 26A-26B show various views of another exemplary expansion and locking mechanism.
Figure 26B:
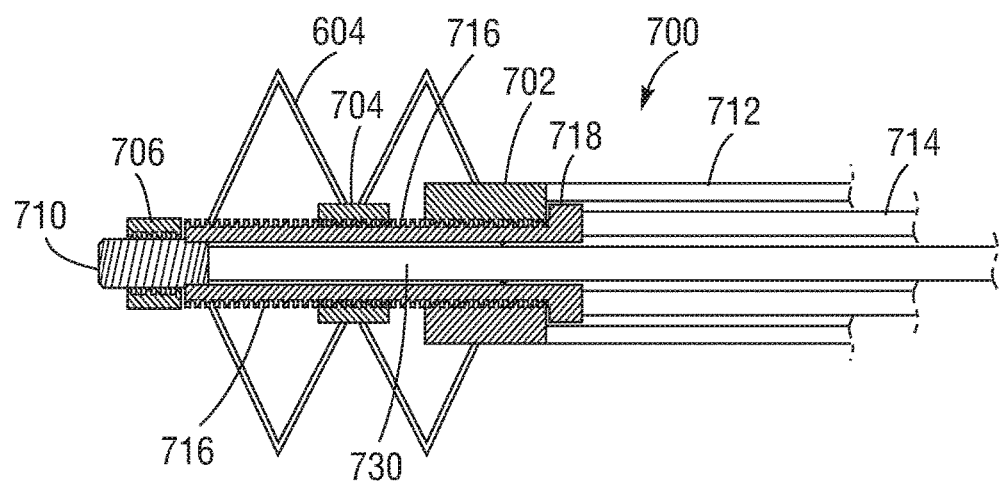

FIGS. 26A and 26B show cross-sectional views of expansion and locking mechanism 700, according to another embodiment. The expansion and locking mechanism 700 can be used to both radially expand and lock a prosthetic valve in a radially expanded state, such as prosthetic valve 602. Therefore, an alternative embodiment of a prosthetic valve delivery assembly can be the same as delivery assembly 600 with one or more of the linear actuator assemblies 608 and one or more of the locking mechanisms 610 replaced with one or more expansion and locking mechanisms 700. For example, instead of delivery assembly 600 of FIG. 19A with two linear actuator assemblies 608 and one locking mechanism 610 or delivery assembly 600' of FIG. 19B with one linear actuator assembly 608 and two locking mechanisms 610, a delivery assembly can have three expansion and locking mechanisms 700. In other embodiments, the delivery assembly 600 or the delivery assembly 600' can have any number of linear actuator assemblies 608 and/or locking mechanisms 610 replaced by expansion and locking mechanisms 700. Example delivery assemblies can have any number of expansion and locking mechanisms 700.

FIG. 26A shows the expansion and locking mechanism 700 and the frame 604 when the frame is in a radially collapsed or crimped configuration and FIG. 26B shows the expansion and locking mechanism 700 and the frame 604 when the frame is in a radially expanded configuration. As explained above, a delivery assembly may have multiple expansion and locking mechanisms but only one is shown in FIGS. 26A-26B for purposes of illustration.

The expansion and locking mechanism 700 can include a proximal nut or sleeve 702, a distal nut or sleeve 704, and an actuator nut 706 affixed to the frame 604. The nuts 702, 704, 706 can be axially spaced apart from each other along the length of the frame 604. The distal nut 704 and the actuator nut 706 can have internal threaded surfaces. In alternative embodiments, the proximal nut 702 can also have an internal threaded surface. The proximal nut 702 can be affixed to a relatively proximal portion of the frame 604, the actuator nut 706 can be affixed to a relatively distal end of the frame, and the distal nut 704 can be affixed to the frame 604 at a location axially between the proximal nut 702 and the actuator nut 706.

The expansion and locking mechanism 700 can further include an actuator member 708 (which functions as a linear actuator or a push-pull member in the illustrated embodiment), an actuator screw 710, a support tube 712, a locking tool 714, and a locking screw 716. The actuator member 708 can be, for example, a rod, a cable, or wire. The actuator member 708 can be connected at its distal end to the actuator screw 710 such that rotation of the actuator member causes rotation of the actuator screw 710. The proximal end of the actuator member 708 can be connected to a handle or other control device (not shown) that a doctor or operator of the delivery assembly utilizing the expansion and locking mechanism 700 can use to rotate the actuator member 708. Similarly the proximal ends of the support tube 712 and the locking tool 714 can be connected to the handle.

The actuator screw 710 has an externally threaded surface that can engage with the internally threaded surface of the actuator nut 706. When the actuator member 708 is rotated to screw the screw 710 into the actuator nut 706, the actuator member 708 becomes connected to the distal end of the frame 604 such that proximal or distal motion of the actuator member causes proximal or distal motion, respectively, of the distal end of the frame.

The locking screw 716 annularly surrounds the actuator member 708 such that the actuator member extends through a lumen of the screw. The locking screw 716 has an externally threaded surface that can engage the internally threaded surface of the distal nut 704. The locking screw 716 can move in an axial direction within a lumen of the proximal nut 702 and the actuator member 708 can move freely in an axial direction with respect to the locking screw 716. The locking screw 716 has a screw head 718 at its proximal end and the screw can lock the frame 604 in a particularly radially expanded state as explained in further detail below.

In the illustrated embodiment, the threads of the locking screw 716 can be sized to engage the internal threads of the proximal nut 702 such that the locking screw 716 can move distally and proximally relative to the proximal nut 702 upon rotation of the locking screw 716. In other embodiments, the threads of the locking screw 716 can be spaced inwardly of the threads of the proximal nut 702 such the threads of the screw do not engage the threads of the nut, in which case the locking screw 716 can be slid proximally and distally relative to the proximal nut, at least until the locking screw 716 engages the distal nut 704.

The support tube 712 annularly surrounds a proximal portion of the locking screw 716. The support tube 712 and the proximal nut 702 are sized such that the distal end of the support tube abuts or engages the proximal end of the proximal nut 702 such that the support tube 712 is prevented from moving distally beyond the proximal nut.

The locking tool 714 can be configured to be releasably coupled to the screw head 718 of the locking screw 716 and to operate the locking screw 716 after the prosthetic valve is expanded to a desired size via the actuator member 708 as explained below. The distal end of the locking tool 714 can be coupled to the screw head 718 such that rotation of the locking tool advances the locking screw 716 through the proximal nut 702 and screws the locking screw 716 into the distal nut 704. The distal end of the locking tool 714 and the screw head 718 can have various shapes that allow the locking tool to rotate the locking screw 716 when the locking tool engages the screw. The locking tool 714 can be decoupled from the locking screw 716 after the screw has been screwed into the distal nut 704.

In operation, prior to implantation, the actuator member 708 is threaded into the actuator nut 706 and the locking screw 716 is positioned within the proximal nut 702 but is not threaded into the distal nut 704. The frame 604 can then be placed in a radially collapsed state and the delivery assembly 600 can be inserted in a patient. Once the prosthetic valve 602 is at a desired implantation site, the frame 604 can be radially expanded as described herein.

To radially expand the frame 604, the support tube 712 is held firmly against the proximal nut 702. The actuator member 708 is then pulled in a proximal direction through the locking screw 716, such as by pulling on the proximal end of the actuator member 708 or actuating a control knob on the handle that produces proximal movement of the actuator member 708. Because the support tube 712 is being held against the proximal nut 702, which is connected to a proximal end of the frame 604, the proximal end of the frame 604 is prevented from moving relative to the support tube 712 and the handle. As such, movement of the actuator member 708 in a proximal direction results in movement of the distal end of the frame 604 in a proximal direction causing the frame 604 to foreshorten axially and expand radially. FIG. 26A shows the frame 604 in a radially collapsed state, while FIG. 26B shows the frame in a radially expanded state.

It should be understood that the frame 604 can also be radially expanded by pushing the proximal end of the frame toward the distal end of the frame by pushing the support tube 712 against the proximal nut 702 while keeping the actuator member 708 stationary relative to the handle, or alternatively, by simultaneously pushing the support tube 712 distally against the proximal nut 702 and pulling the actuator member 708 proximally.

After the frame 604 is expanded to a desired radially expanded size, the locking screw 716 can be actuated to lock the frame 604 in the desired radially expanded size. Locking the frame 604 at a particular radially expanded state can be achieved by using the locking tool 714 to advance the locking screw 716 distally and screw the locking screw 716 into the distal nut 704 until the screw head 718 abuts against the proximal nut 702. This will cause the threads of the locking screw 716 to engage the internal threads of the distal nut 704. When the screw head 718 also abuts against the proximal nut 702, the screw 716 cannot be advanced any further in a distal direction, thereby preventing radially compression of the frame 604. However, because the screw 716 can be moved relative to the proximal nut 702 in a proximal direction after the frame 604 is locked, further expansion of the frame 604 is possible, either during initial implantation procedure or later during a valve-in-valve procedure.

Further expansion of the frame can be achieved by pulling the locking screw 716 proximally to move the distal nut 704 toward the proximal nut 702 (if the locking screw 716 is sized to slide freely within the proximal nut 702). Alternatively, if the locking screw 716 is sized to engage the threads of the proximal nut 702, the locking screw 716 can be unscrewed from the distal nut 704, which then allows further expansion of the frame by retracting the actuator member 708.

Once the frame 604 is locked in a radially expanded state, the locking tool 714 can be decoupled from the locking screw 716 and the actuator member 708 can be rotated so as to unscrew the screw 710 from the actuator nut 706. The actuator member 708, the support tube 712, and the locking tool 714 can then be removed from the patient, leaving the locking screw 716 connected to the frame 604 with the frame 604 locked in a particular radially expanded state.

FIGS. 27-28 show another embodiment of a prosthetic valve comprising the frame 604 and expansion and locking mechanisms 800 (with the leaflets and other soft components removed for purposes of illustration). As with expansion and locking mechanism 700, expansion and locking mechanism 800 can be used to both radially expand and lock the prosthetic valve in a radially expanded state. As such, an alternative embodiment of a prosthetic valve delivery system can be the same as delivery assembly 600 with one or more of the linear actuator assemblies 608 and one or more of the locking mechanisms 610 replaced with one or more expansion and locking mechanisms 800. In the example of FIGS. 27 and 28, three expansion and locking mechanisms 800 are attached to the frame 604 but in other example delivery assemblies, any number of expansion and locking mechanisms 800 can be used. FIG. 27 shows the expansion and locking mechanisms 800 attached to the frame 604 when the frame is in a radially collapsed configuration and FIG. 28 shows expansion and locking mechanisms attached to the frame when the frame is in a radially expanded configuration. FIGS. 53A-53D are various views of the bare frame 604 with other components of the prosthetic valve removed for purposes of illustration. FIGS. 52A-52F are various views of one of the struts of the frame.

Referring to FIGS. 29A-29C, the expansion and locking mechanism 800 in the illustrated embodiment can include an actuator screw 802 (which functions as a linear actuator or a push-pull member in the illustrated embodiment) comprising a relatively long upper, or distal, portion 804 and a relatively shorter lower, or proximal, portion 806 at the proximal end of the screw 800, wherein the lower portion has a smaller diameter than the upper portion. Both the upper and lower portions 804, 806 of the screw 802 can have externally threaded surfaces.

The actuator screw 800 can have a distal attachment piece 808 attached to its distal end having a radially extending distal valve connector 810. The distal attachment piece 808 can be fixed to the screw 802 (e.g., welded together or manufactured as one piece). The distal valve connector 810 can extend through an opening at or near the distal end of the frame 604 formed at a location on the frame where two or more struts intersect as shown in FIG. 29C. The distal valve connector 810 can be fixed to the frame 604 (e.g., welded). Due to the shape of the struts, the distal end of the frame 604 comprises an alternating series of distal junctions 650 and distal apices 652. In the illustrated example, the distal valve connectors 810 of the three expansion and locking mechanisms 800 are connected to the frame 604 through distal junctions 650. In other examples, one or more distal valve connectors 810 can be connected to the frame 604 through distal apices 652. In other embodiments, the distal valve connectors 810 can be connected to junctions closer to the proximal end of the frame 604.

The expansion and locking mechanism 800 can further include a sleeve 812. The sleeve 812 can be positioned annularly around the upper portion 806 of the screw 802 and can contain axial openings at its proximal and distal ends through which the screw 802 can extend. The axial openings and the lumen in the sleeve 812 can have a diameter larger than the diameter of the upper portion 806 of the screw 802 such that the screw can move freely within the sleeve (the screw 802 can be moved proximally and distally relative to the sleeve 812). Because the actuator screw 802 can move freely within the sleeve, it can be used to radially expand and/or contract the frame 604 as disclosed in further detail below.

The sleeve 812 can have a proximal valve connector 814 extending radially from its outer surface. The proximal valve connector 814 can be fixed to the sleeve 812 (e.g., welded). The proximal valve connector 814 can be axially spaced from the distal valve connector 810 such that the proximal valve connector can extend through an opening at or near the proximal end of the frame 604. The proximal end of the frame 604 comprises an alternating series of proximal junctions 660 and proximal apices 662. In the illustrated example, the proximal valve connectors 814 of the three expansion and locking mechanisms 800 are connected to the frame 604 through proximal junctions 660. In other examples, one or more proximal valve connectors 814 can be connected to the frame 604 through proximal apices 662. In other embodiments, the proximal valve connectors 814 can be connected to junctions closer to the distal end of the frame 604.

It should be understood that the distal and proximal connectors 810, 814 need not be connected to opposite ends of the frame. The actuator 800 can be used to expand and compress the frame as long as the distal and proximal connectors are connected to respective junctions on the frame that are axially spaced from each other.

A locking nut 816 can be positioned inside of the sleeve 812 and can have an internally threaded surface that can engage the externally threaded surface of the actuator screw 802. The locking nut 816 can have a notched portion 818 at its proximal end, the purpose of which is described below. The locking nut can be used to lock the frame 604 into a particularly radially expanded state, as discussed below.

Figure 30:
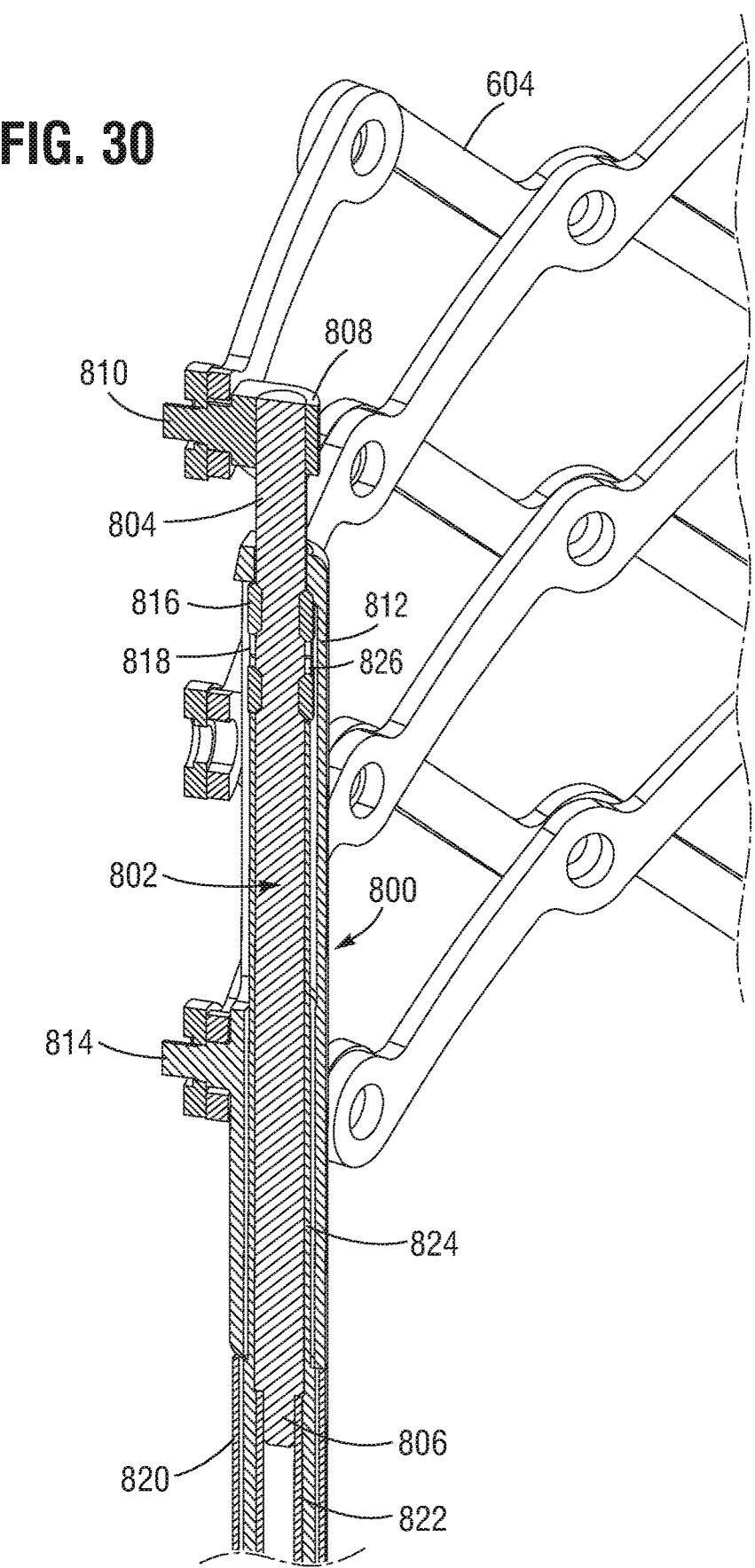
FIG. 30 shows a cross sectional view of one of the expansion and locking mechanisms of FIG. 27 along with a portion of the frame.

FIG. 30 shows a cross sectional view of the expansion and locking mechanism 800 including delivery components not shown in FIGS. 29A-29C. Referring to FIG. 30, the expansion and locking mechanism 800 can further include a support tube 820, an actuator member 822, and a locking tool 824. The proximal end of the support tube 820 can be connected to a handle or other control device (not shown) that a doctor or operator of the delivery assembly utilizing to operate the expansion and locking mechanism 800 as described herein. Similarly, the proximal ends of the actuator member 822 and the locking tool 824 can be connected to the handle.

The support tube 820 annularly surrounds a proximal portion of the locking tool 824 such that the locking tool extends through a lumen of the support tube. The support tube 820 and the sleeve are sized such that the distal end of the support tube abuts or engages the proximal end of the sleeve 812 such that the support tube is prevented from moving distally beyond the sleeve.

The actuator member 822 extends through a lumen of the locking tool 824. The actuator member 822 can be, for example, a shaft, a rod, a cable, or wire. The distal end portion of the actuator member 822 can be releasably connected to the lower portion 806 of the actuator screw 802. For example, the distal end portion of the actuator screw 802 can have an internally threaded surface that can engage the external threads of the lower portion 806 of the actuator screw 802. Alternatively, the actuator member can have external threads that engage an internally threaded portion of the screw. When the actuator member 822 is threaded onto the actuator screw 802, axial movement of the actuator member causes axial movement of the screw.

The distal portion of the locking tool 824 annularly surrounds the actuator screw 802 and extends through a lumen of the sleeve 812 and the proximal portion of the locking tool annularly surrounds the actuator member 822 and extends through a lumen of the support tube 820 to the handle of the delivery device. The locking tool 824 can have an internally threaded surface that can engage the externally threaded surface of the locking screw 802 such that clockwise or counter-clockwise rotation of the locking tool 824 causes the locking tool to advance distally or proximally along the screw, respectively.

Figure 31:
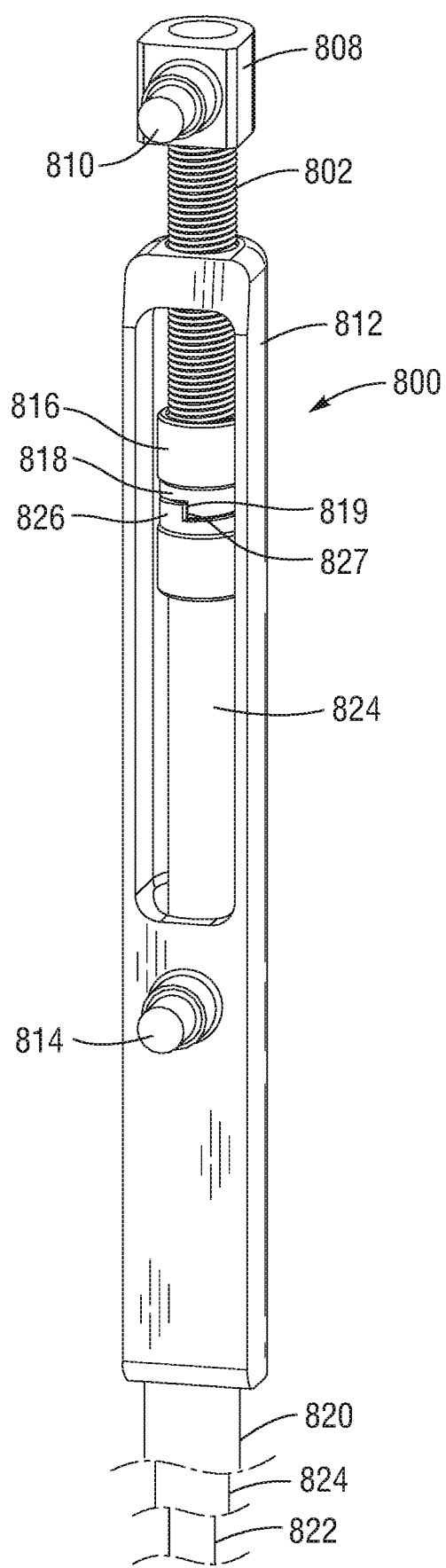
FIG. 31 is another perspective view of one of the expansion and locking mechanisms of FIG. 27.

The distal end of the locking tool 824 can comprise a notched portion 826, as can best be seen in FIG. 31. The notched portion 826 of the locking tool 824 can have an engagement surface 827 that is configured to engage a correspondingly shaped engagement surface 819 of the notched portion 818 of the locking nut 816 such that rotation of the locking tool (e.g., clockwise rotation) causes the nut 816 to rotate in the same direction (e.g., clockwise) and advance distally along the locking screw 802. The notched portions 818, 826 in the illustrated embodiment are configured such that rotation of the locking tool 824 in the opposite direction (e.g., counter-clockwise) allows the notched portion 826 of the tool 824 to disengage the notched portion 818 of the locking nut 816; that is, rotation of the locking tool in a direction that causes the locking tool to move proximally does not cause corresponding rotation of the nut.

In alternative embodiments, the distal end portion of the locking tool 824 can have various other configurations adapted to engage the nut 816 and produce rotation of the nut upon rotation of the locking tool for moving the nut distally, such as any of the tool configurations described herein. In some embodiments, the distal end portion of the locking tool 824 can be adapted to produce rotation of the nut 816 in both directions so as move the nut distally and proximally along the locking screw 802. For example, the distal end portion of the locking tool 824 can have the configuration of tool 634 shown in FIGS. 25A-25D.

In operation, prior to implantation, the actuator member 822 is screwed onto the lower portion 806 of the actuator screw 802 and the locking nut 816 is rotated such that it is positioned at the proximal end of the screw. The frame 604 can then be placed in a radially collapsed state and the delivery assembly 600 can be inserted into a patient. Once the prosthetic valve is at a desired implantation site, the frame 604 can be radially expanded as described herein.

To radially expand the frame 604, the support tube 820 is held firmly against the sleeve 812. The actuator member 822 is then pulled in a proximal direction through the support tube, such as by pulling on the proximal end of the actuator member or actuating a control knob on the handle that produces proximal movement of the actuator member. Because the support tube 820 is being held against the sleeve 812, which is connected to a proximal end of the frame 604 by the proximal valve connector 814, the proximal end of the frame is prevented from moving relative to the support tube. As such, movement of the actuator member 822 in a proximal direction causes movement of the actuator screw 802 in a proximal direction (because the actuator member is threaded onto the screw), thereby causing the frame 604 to foreshorten axially and expand radially. Alternatively, the frame 604 can be expanded by moving the support tube 820 distally while holding the actuator member 822 stationary, or moving the support tube distally while moving the actuator member 822 proximally.

After the frame 604 is expanded to a desired radially expanded size, the frame can be locked at this radially expanded size as described herein. Locking the frame can be achieved by rotating the locking tool 824 in a clockwise direction causing the notched portion 826 of the locking tool to engage the notched portion 818 of the locking nut 816, thereby advancing the locking nut distally along the actuator screw 802. The locking tool 824 can be so rotated until the locking nut 816 abuts an internal shoulder at the distal end of the sleeve 812 and the locking nut 816 cannot advance distally any further (see FIG. 31). This will prevent the screw 802 from advancing distally relative to the sleeve 812 and radially compressing the frame 604. However, in the illustrated embodiment, the nut 816 and the screw 802 can still move proximally through the sleeve 812, thereby allowing additional expansion of the frame 604 either during implantation or later during a valve-in-valve procedure.

Once the frame 604 is locked in radially expanded state, the locking tool 824 can be rotated in a direction to move the locking tool proximally (e.g., in a counter-clockwise direction) to decouple the notched portion 826 from the notched portion 818 of the locking nut 816 and to unscrew the locking tool from the actuator screw 804. Additionally, the actuator member 822 can be rotated in a direction to unscrew the actuator member from the lower portion 806 of the actuator screw 802 (e.g., the actuator member 822 can be configured to disengage from the actuator screw when rotated counter-clockwise). Once the locking tool 824 and the actuator member 822 are unscrewed from the actuator screw 804, they can be removed from the patient along with the support tube 820, leaving the actuator screw and the sleeve 812 connected to the frame 604, as shown in FIG. 29C, with the frame 604 locked in a particular radially expanded state.

In an alternative embodiment, the locking tool 824 can be formed without internal threads that engage the external threads of the actuator screw 802, which can allow the locking tool 824 to be slid distally and proximally through the sleeve 812 and along the actuator screw 802 to engage and disengage the nut 816.

Any of the delivery assemblies disclosed herein can have various handle configurations with one or more actuators or controls configured to produce movement of components of the assembly that expand and compress a prosthetic valve (or another type of implant). In some embodiments, such as shown in FIGS. 1 and 13), the handle can have actuators that are manually operated by a user by manually rotating and/or manually pushing/pulling actuators on the handle. In other embodiments, the actuators on the handle and/or other components of the assembly can be electrically, pneumatically and/or hydraulically controlled.

For example, in some embodiments, the handle can house one or more electric motors that are actuated by a user to produce movement of components of the delivery assembly, such as one or more motors operable to produce linear movement of the actuator screws 802, and one or more motors operable to produce rotational movement of the locking tools 824 (for rotating locking nuts 816). In one specific implementation, one electric motor is used to produce linear movement of all of the actuators screws 802 mounted on the prosthetic valve and one electric motor is used to produce rotational movement of all of the locking tools 824 included in the assembly. In another implementation, one electric motor can be provided for each actuator screw and for each locking tool 824. Further details regarding handle configurations that include electric motors for controlling delivery assembly components are disclosed in U.S. Publication No. 2014/0296962, which is incorporated herein by reference.

Additionally, any of the delivery assemblies disclosed herein can include software and/or hardware operable to control expansion of a prosthetic valve, as further disclosed in U.S. Publication No. 2014/0296962. In particular embodiments, a delivery assembly can include a programmable controller (such as housed in the handle) that is operable to radially expand a prosthetic valve according to a specific algorithm. For example, a delivery assembly can include one or more motors (e.g., electric motors) that are controlled by an electronic controller to radially expand a prosthetic valve according to a specific algorithm. In certain implementations, for example, the controller can be programed to produce pulsatile radial expansion of a prosthetic valve, as further disclosed in U.S. Publication No. 2014/0296962.

Figure 32:
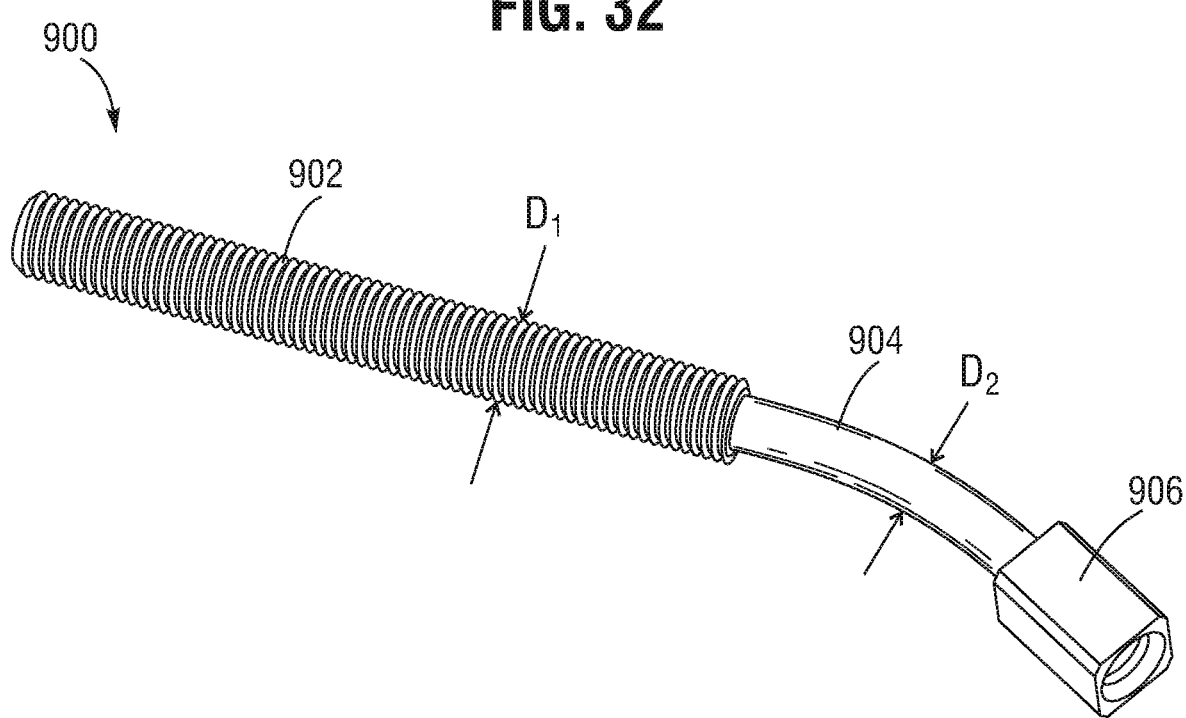
FIG. 32 shows an exemplary flexible screw that can be implemented in a prosthetic heart valve.

FIG. 32 shows an exemplary flexible screw 900 that can be used to replace any of the screws described herein such as, for example, locking screw 624. As described above with respect to valve assembly 600, prior to implantation in a patient the prosthetic valve is crimped to a radially collapsed state. However, the presence of locking mechanism 610 and locking screw 624 in the illustrated example of FIG. 18, for example, can limit the degree to which the prosthetic valve can be radially collapsed. Specifically, the width of locking screw 624 extends into the frame profile, which can limit the degree to which the frame 604 can be crimped. Since a smaller crimped diameter is preferable for implantation into a patient, reducing the diameter of the locking screw 624 is desirable.

However, the tension force on the screw during valve expansion, the torque required to rotate the screw, the fatigue tension of the screw during the lifecycle of the valve, and bending moments due to side forces on the screw all limit the amount to which the diameter of the locking screw 624 can be reduced. For example, deformation of the frame during crimping can exert bending forces on the screw, which can cause plastic deformation of the screw. Thus, incorporating a screw adapted to flex or bend along at least a portion of the screw without permanent deformation can allow a reduction of the screw diameter along all or a portion of the length of the screw.

The flexible screw 900 in the illustrated embodiment can comprise a relatively rigid threaded portion 902, a relatively flexible portion 904, and a screw head 906 connected to the end of the flexible portion, with the flexible portion 904 positioned between the threaded portion 902 and the screw head 906. The threaded portion 902 can have an externally threaded surface. The flexible portion 904 is relatively more flexible than the rigid threaded portion 902 and therefore can flex or bend relative to the threaded portion. The flexible portion 904 can comprise, for example, a braided cable, a wire, a laser cut tube, or a hypotube. The threaded portion 902, the flexible portion 904, and the screw head 906 can be connected together via, for example, laser welding, a pressed connection, or by integrating and machining them all as one piece. The threaded portion 902, the flexible portion 904, and the screw head 906 can be made of, for example, titanium (e.g., Ti-6Al-4V ELI), cobalt-chrome, stainless steel (e.g., 316, 304), PEEK, or other materials.

Figure 33:
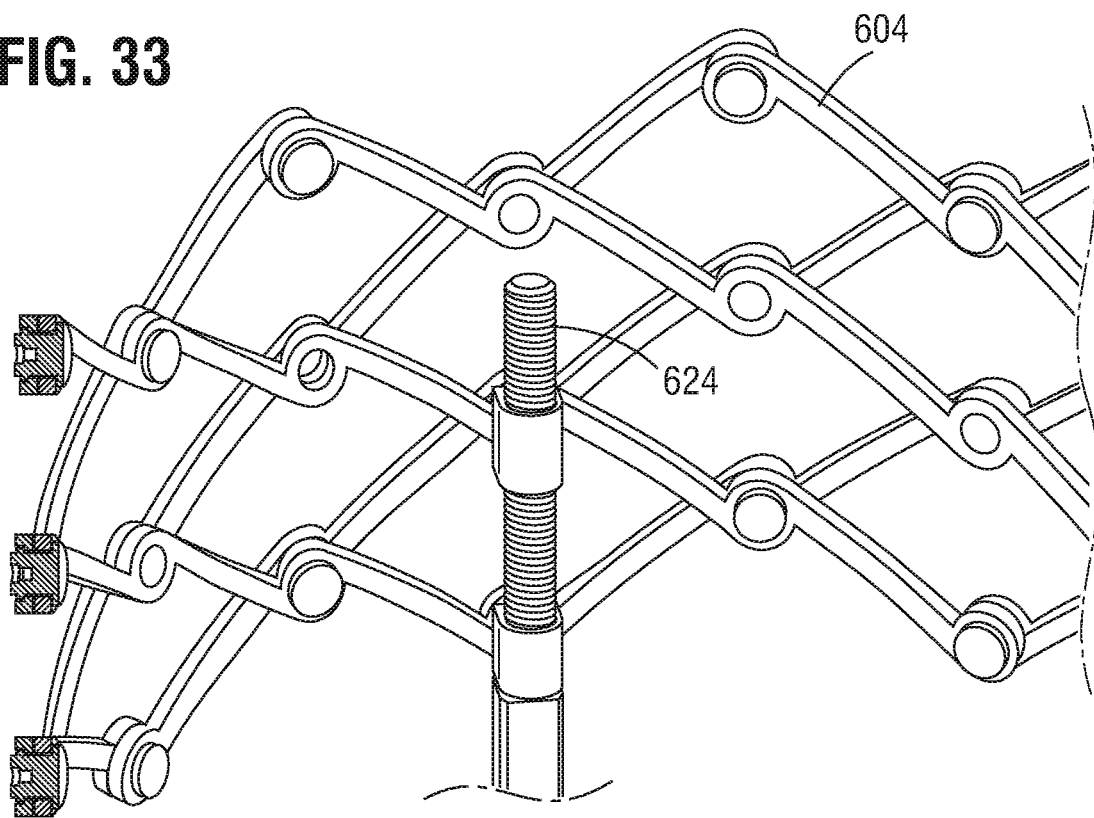
FIG. 33 shows a portion of the frame of a prosthetic valve locked in place with a rigid screw.
Figure 34:
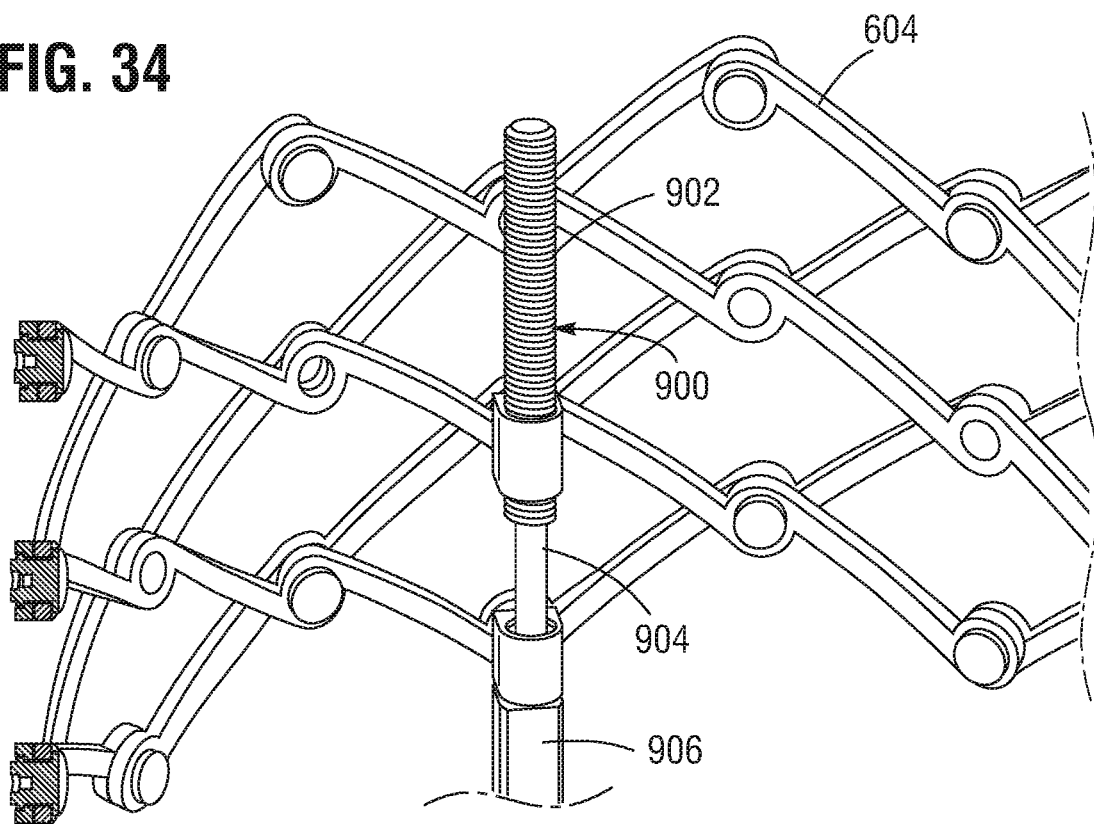
FIG. 34 shows a portion of the frame of a prosthetic valve locked in place with the flexible screw of FIG. 32.

FIG. 33 shows a portion of an exemplary valve assembly where a locking screw 624 is used to lock the frame 604 in a particular expanded state. FIG. 34 shows a portion of an exemplary valve assembly where a flexible screw 900 replaces the rigid screw 624. The flexible portion 904 of screw 900 can bend and absorb bending forces upon radial expansion and compression of the frame without permanent or plastic deformation of the screw. As such, the flexible screw 900 can have a smaller diameter than is possible with the screw 624. Specifically, the diameter of the threaded portion 902 of flexible screw 900 can be smaller than the diameter of rigid screw 624. Referring to FIG. 32, in some embodiments, the diameter D1 of the threaded portion 902 can be between 0.3 mm and 1 mm, and more desirably, between 0.4 mm and 0.6 mm, with 0.5 mm being a specific example. In some embodiments, the diameter D2 of the flexible portion 904 can be between 0.1 mm and 0.6 mm, and more desirably between 0.2 mm and 0.4 mm, with 0.3 mm being a specific example. The flexible screw 900 otherwise operates in the same manner as the locking screw 624.

FIG. 35 shows an exemplary flexible screw 1000, according to another embodiment. The screw 1000 comprises a relatively rigid threaded portion 1002, a relatively flexible portion 1004 that is more flexible than the threaded portion, a screw head 1006 connected to the end of the threaded portion, and a stopper 1008. The flexible screw 1000 is similar to the flexible screw 900 except that the threaded portion 1002 is positioned between the flexible portion 1004 and the screw head 1006 and the addition of the stopper 1008 connected to the distal end of the flexible portion 1004. An advantage of the flexible screw 1000 is that there is no need to transfer torque through the flexible portion 1004 of the screw 1000 when screwing the screw onto the frame.

Figure 36A:
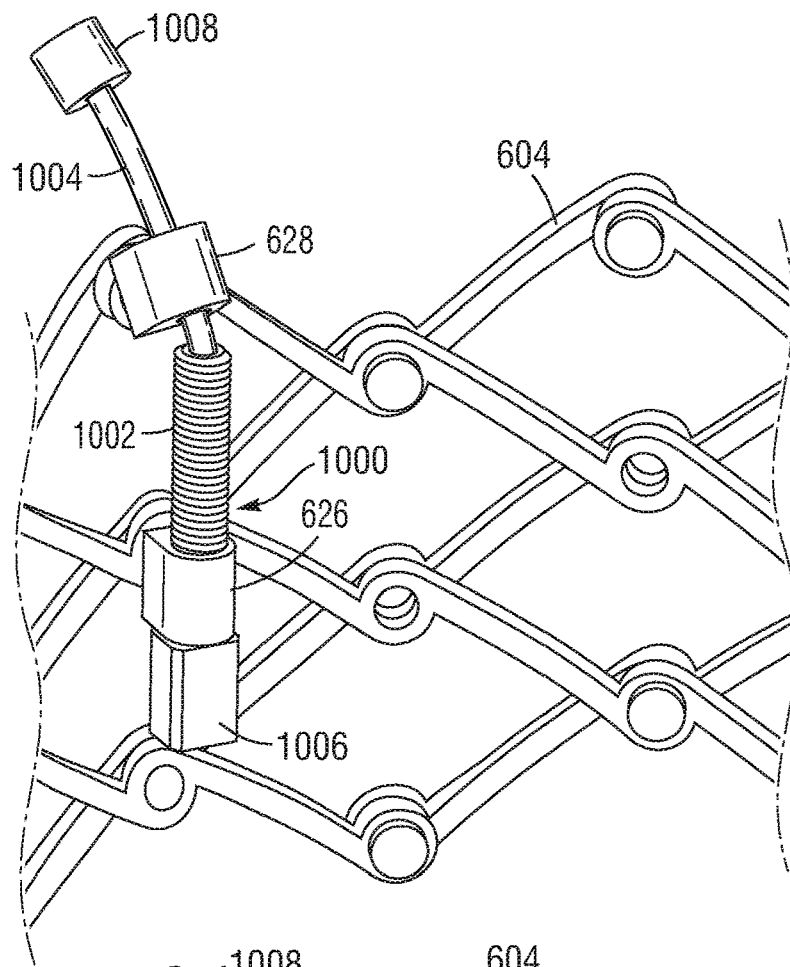
FIG. 36A shows a portion of the frame of a prosthetic valve and the flexible screw of FIG. 35 prior to locking the valve in place.
Figure 36B:
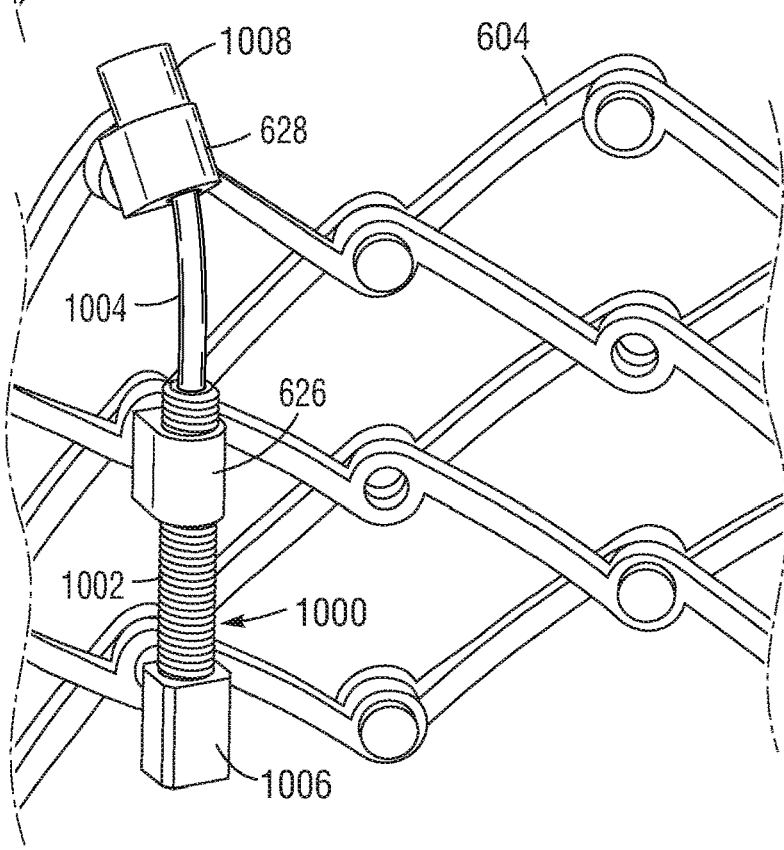
FIG. 36B shows a portion of the frame of a prosthetic valve locked in place with the flexible screw of FIG. 35.

FIGS. 36A-36B show a portion of an exemplary valve assembly where the flexible screw 1000 can be used to lock the frame 604 in a particular radially expanded state. In the illustrated example of FIG. 36A, the valve is shown in an expanded configuration prior to locking the valve. In the illustrated example of FIG. 36B, the valve is shown after it is locked in place using the screw 1000. The example valve assembly of FIGS. 36A-36B can be manufactured by connecting the stopper 1008 to the screw 1000 after positioning the screw within the proximal and distal nuts 626, 628. For example, the threaded portion 1002 of the screw 1000 could first be screwed into the proximal nut 626, followed by inserting the flexible portion 1004 of the screw through the distal nut 628. The stopper 1008 could then be welded or otherwise affixed to the distal end of the flexible portion 1008 to trap the proximal and distal nuts 626, 628 between the screw head 1006 and the stopper. Other methods of manufacture can also be used to ensure that the nuts 626, 628 are positioned between the screw head 1006 and the stopper 1008. When the frame 604 is compressed into a crimped configuration prior to implantation in a patient (e.g., from the configuration shown in FIG. 36A), the distal nut 628 is positioned closer to the stopper 1008. As such, the flexible portion 1004 must be long enough so that the frame 604 can be crimped the desired amount without the distal nut abutting against the stopper.

In the example of FIGS. 36A-36B, the threaded portion 1002 of the flexible screw 1000 can engage internal threads of the proximal nut 626 and the flexible portion 1004 can move freely within the distal nut 628 in an axial direction. After the frame is expanded (e.g., with one or more linear actuator assemblies 608 of FIG. 18) to a desired radial expansion size, as shown in FIG. 36A, the screw 1000 can be used to lock the frame as described herein. Locking the frame can be accomplished by rotating the screw to move it in a proximal direction with respect to the nuts 626, 628 (e.g., by rotating the screw in a counter-clockwise direction). The screw 1000 can be so rotated until the stopper 1008 abuts the distal nut 628, as shown in FIG. 36B. From this configuration, further radial expansion of the frame is possible by additionally foreshortening the frame and reducing the axial distance between the proximal nut 626 and the distal nut 628. However, radial compression of the frame is prohibited in the locked configuration of FIG. 36B because the threaded portion 1002 being threaded to the proximal nut 626 and the stopper 1008 abutting the distal nut 628 prevent the axial distance between the proximal and distal nuts from increasing.

Figure 37A:
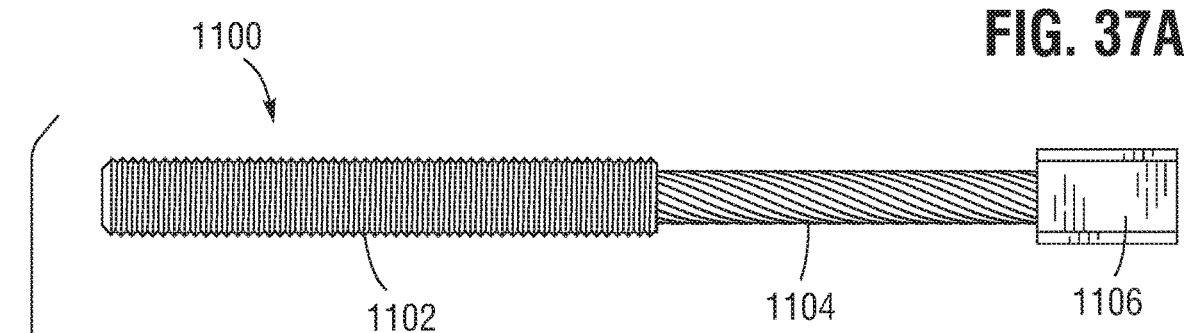
FIGS. 37A-37C show alternative embodiments of a flexible screw that can be implemented in a prosthetic heart valve.
Figure 37B:
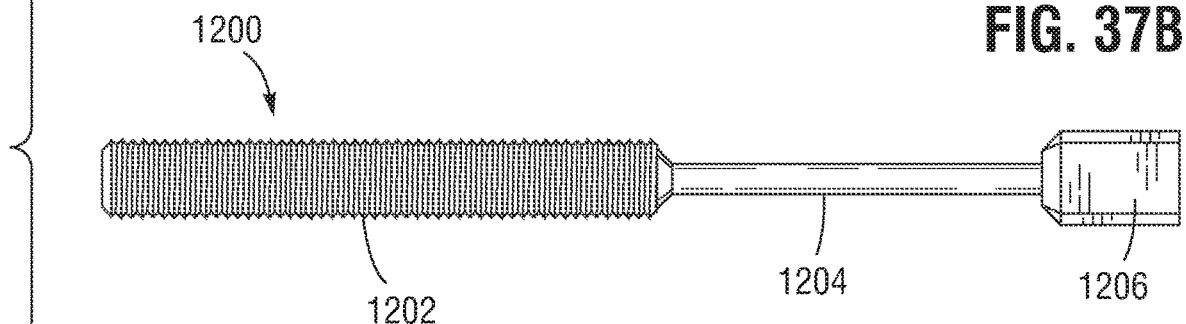
Figure 37C:
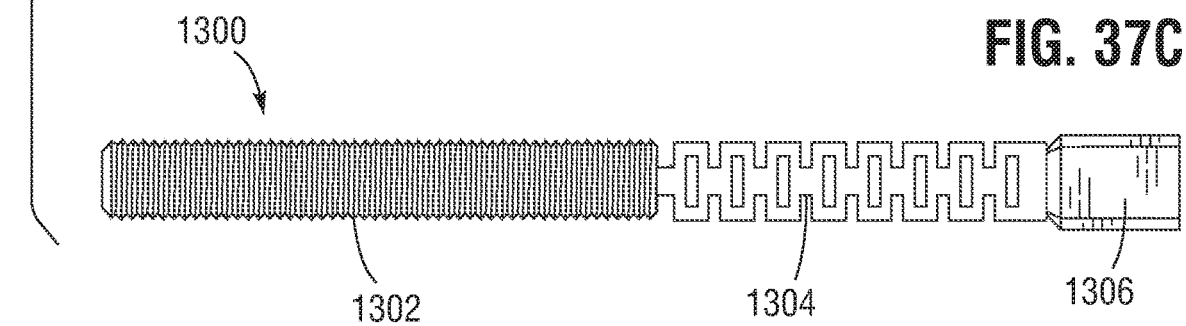

FIGS. 37A-37C show alternative flexible screws 1100, 1200, and 1300. Each of the flexible screws 1100, 1200, 1300 have a relatively rigid threaded portion 1102, 1202, 1302 respectively, similar to threaded portion 902 of screw 900 and a screw head 1106, 1206, 1306 respectively, similar to screw head 906 of screw 900, connected to the end of the flexible portion opposite the threaded portion. In the example of FIG. 37A, the screw 1100 has a flexible portion 1104 comprising a cable (e.g., a welded or pressed braided cable). In the example of FIG. 37B, the screw 1200 has a flexible portion 1204 comprising a solid or tubular shaft having a smaller diameter than that of the threaded portion 1202. The screw 1200 can be manufactured by one part machining (e.g., machining a solid shaft or hollow tube, such as by laser cutting). In the example of FIG. 37C, the screw 1300 has a flexible portion 1304 comprising metal hypotube that can be formed, for example, by laser cutting a metal tube.

The flexible screws 900, 1000, 1100, 1200, 1300 can also be used with prosthetic valves that have a rotatable or screw type mechanical expansion mechanism, such as prosthetic valve 1800 of FIG. 51, described in further detail below. In the illustrated example of FIG. 51, screws 900 are shown but could be replaced with any of screws 1000, 1100, 1200, or 1300.

Figure 51:
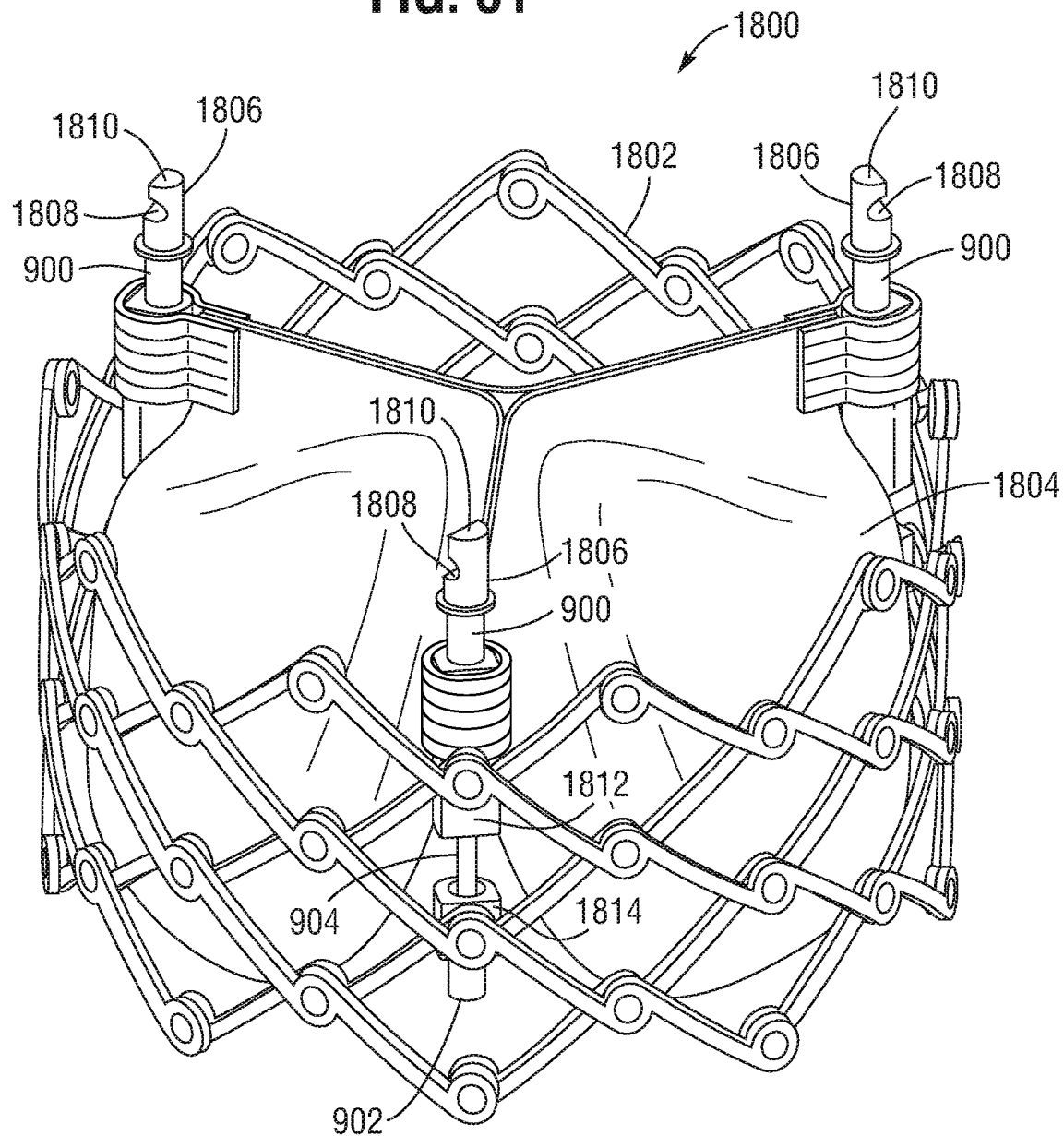
FIG. 51 is a perspective view of a prosthetic valve, according to another embodiment.
Figure 52A:
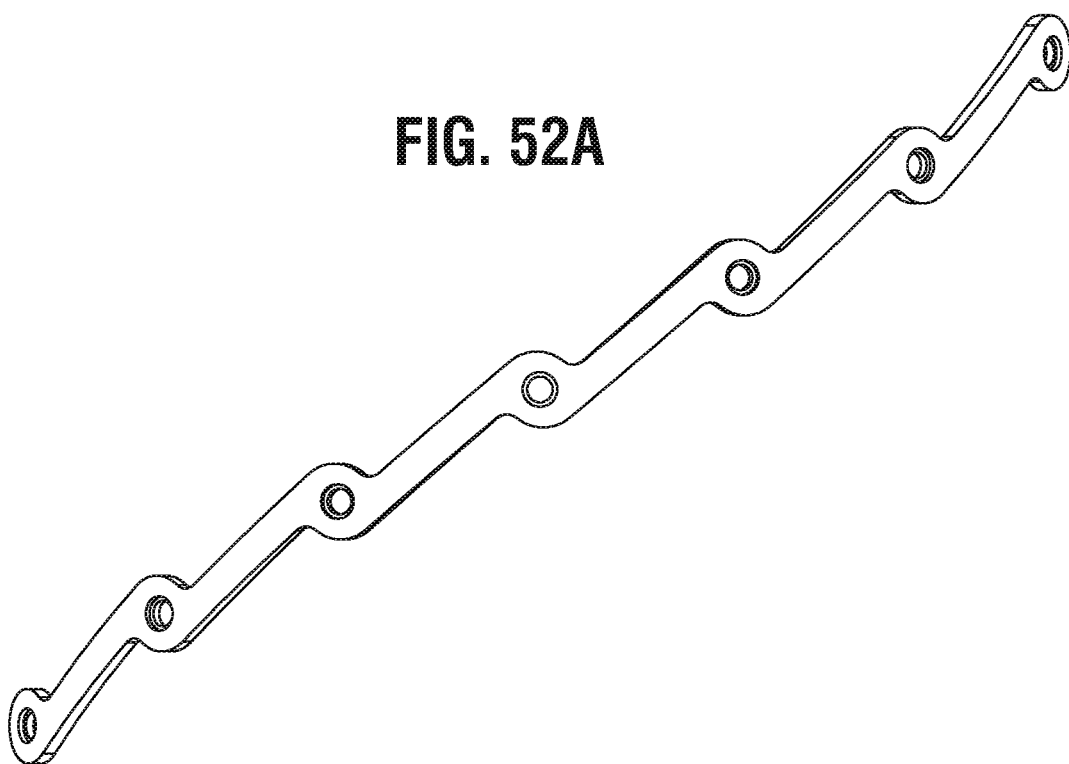
Figure 52B:
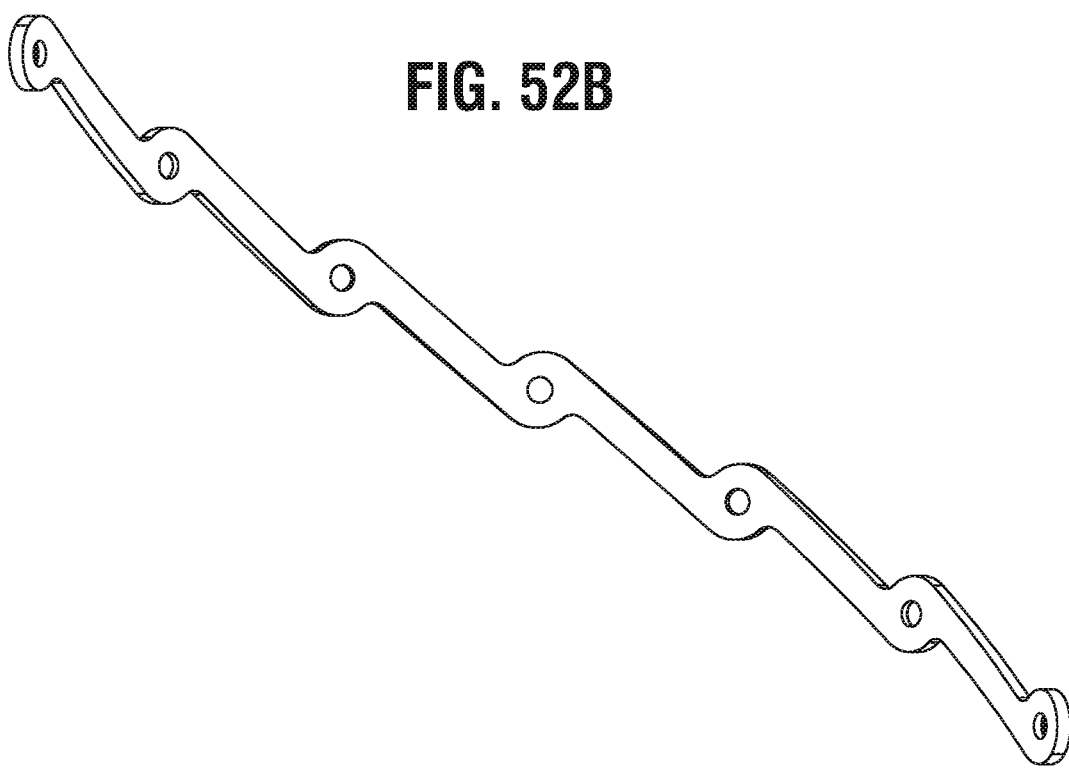
Figure 53A:
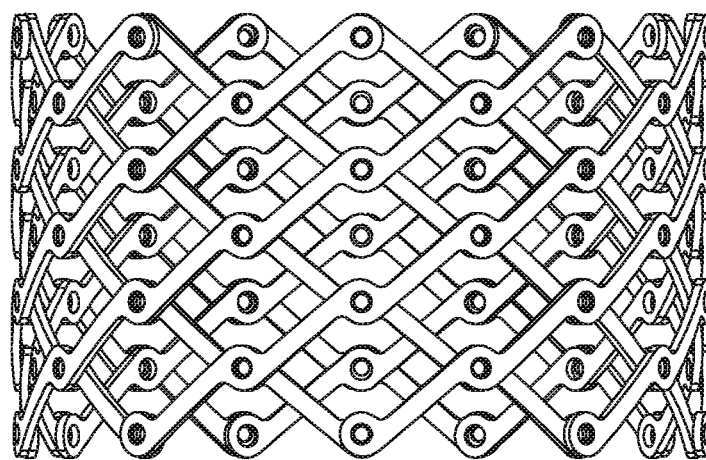
FIGS. 53A-53D show various views of a frame of a prosthetic valve formed from multiple struts of the type shown in FIGS. 52A-52F.
Figure 53B:
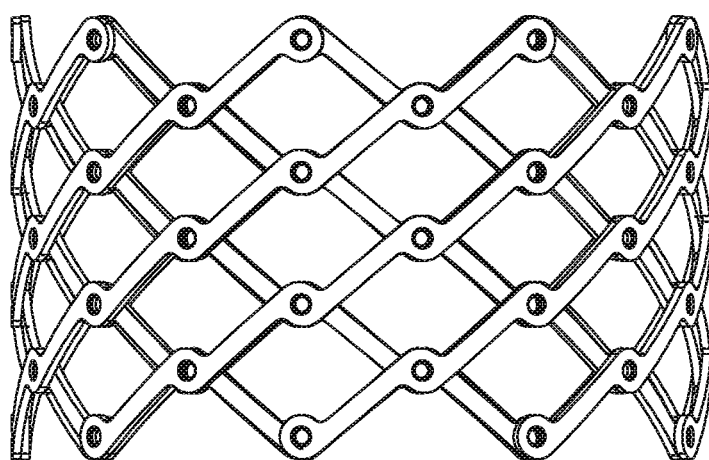
Figure 53C:
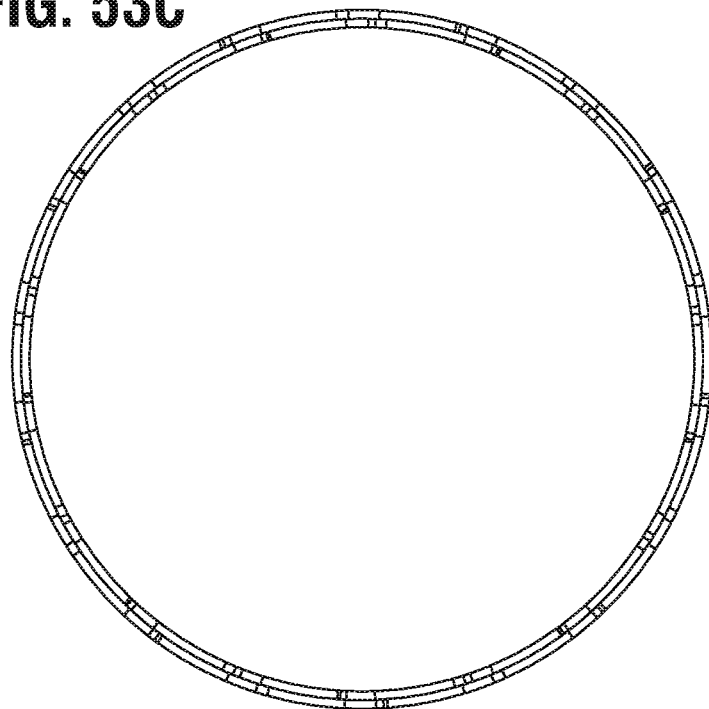
Figure 53D:
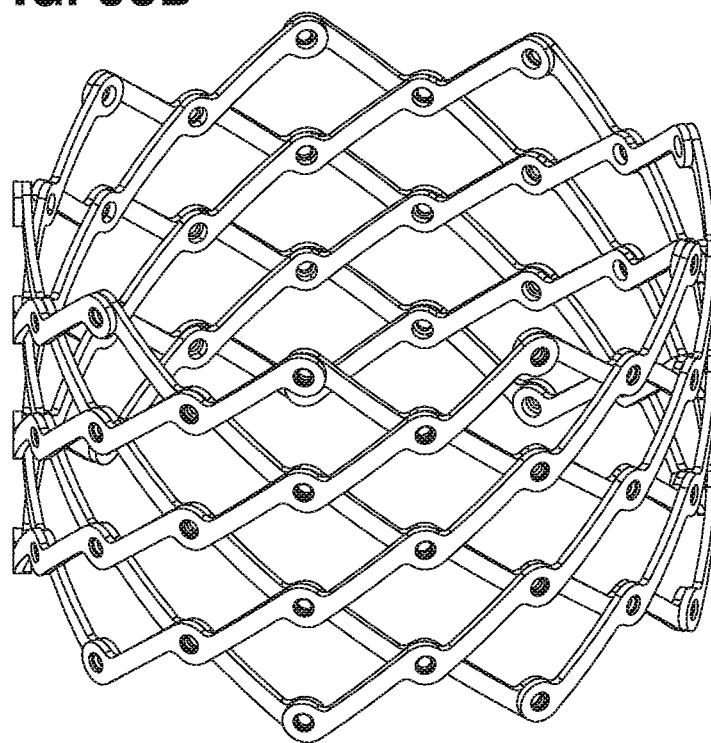

Referring to FIG. 51, the prosthetic valve 1800 comprises a frame 1802, which can have the same construction as the frame 602 of FIG. 18, and a valvular structure 1804. In this embodiment, a proximal end portion of each screw 900 can be modified to include an attachment member 1806 that can include a notch 1808 and a projection 1810 that can releasably couple to a corresponding projection of a drive shaft of a delivery apparatus (not shown). The drive shaft can be attached to a motor or other device that can cause it to rotate. When the drive shaft is so rotated while coupled to the attachment member 1806 of a screw 900, the torque can be transferred to the screw, causing the screw to rotate.

A sleeve 1812 and a nut 1814 can be attached to the frame 1802 at axially spaced locations. The screw 900 can be fixed axially relative to the sleeve 1812 while the threaded portion 902 of the screw can engage internal threads of the nut 1814 such that rotation of the screw 900 causes the distance between the attachment locations of the sleeve 1812 and the nut 1814 to vary such that the frame 1802 expands or contracts radially, based on the direction of the rotation. The flexible portion 904 can extend along the screw at least partially between the sleeve 1812 and the nut 1814.

In other examples, the prosthetic valve 1800 can incorporate screws 1000, in which case each screw 1000 can be axially fixed to a sleeve 1814 (similar to nut 1814 but without internal threads) and the threaded portion 1002 of the screw can engage internal threads of a nut 1812 (similar to sleeve 1812 but with internal threads), which also results in rotation of the screw causing expansion or contraction of the frame 1802. Further details regarding the prosthetic valve 1800 and delivery devices that can be used to implant the prosthetic valve are disclosed in U.S. Provisional Appl. No. 62/548,855, which is incorporated herein by reference.

Figure 38:
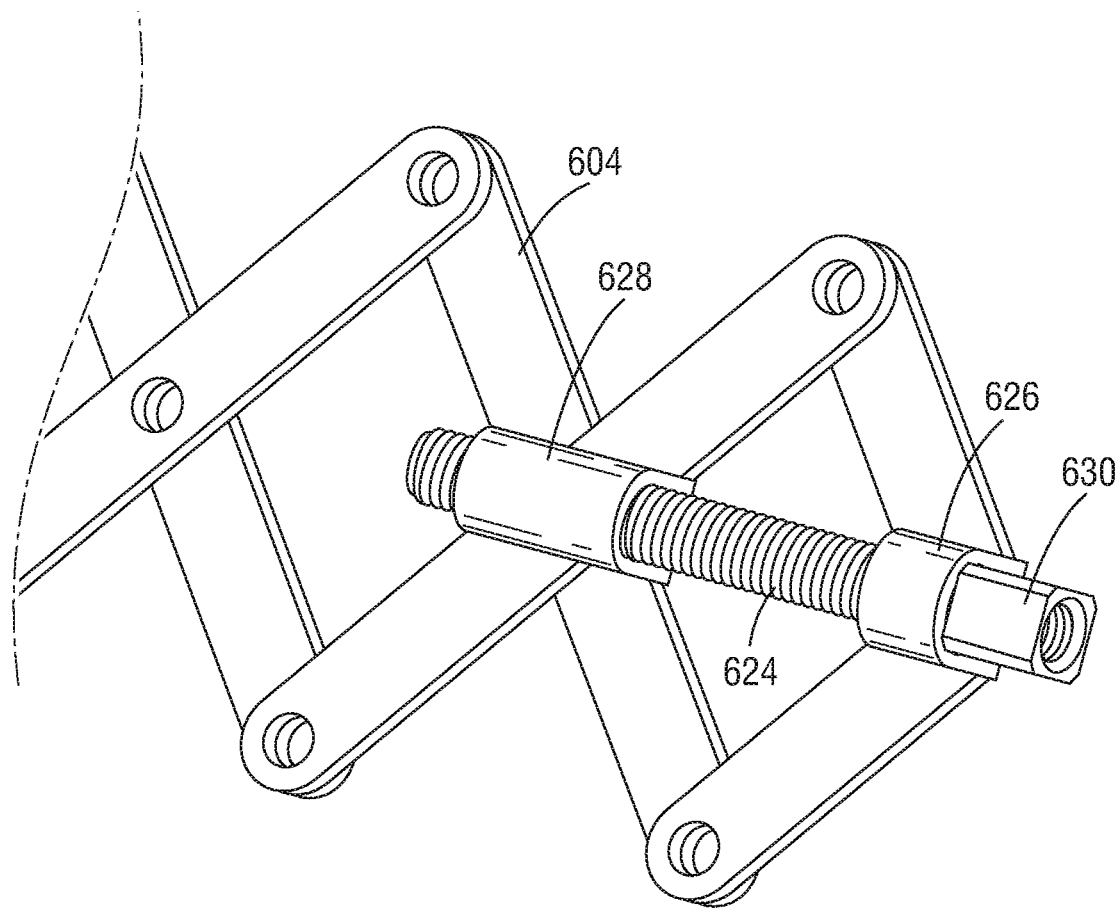
FIG. 38 shows a portion of the frame of a prosthetic valve locked in place with a screw.

FIG. 38 shows a portion of frame 604 and a locking screw 624 when the screw is screwed into proximal nut 626 and distal nut 628 to lock the frame in a particular radially expanded state as discussed above in connection with FIGS. 24A-24D. Utilizing a screw such as the locking screw 624 to lock the frame is a robust and simple design due to the high tension strength of screws and the low torque required for locking. FIGS. 39-49 show various ways of further locking the position of a screw, such as the screw 624, under dynamic vibration loads.

Figure 39:
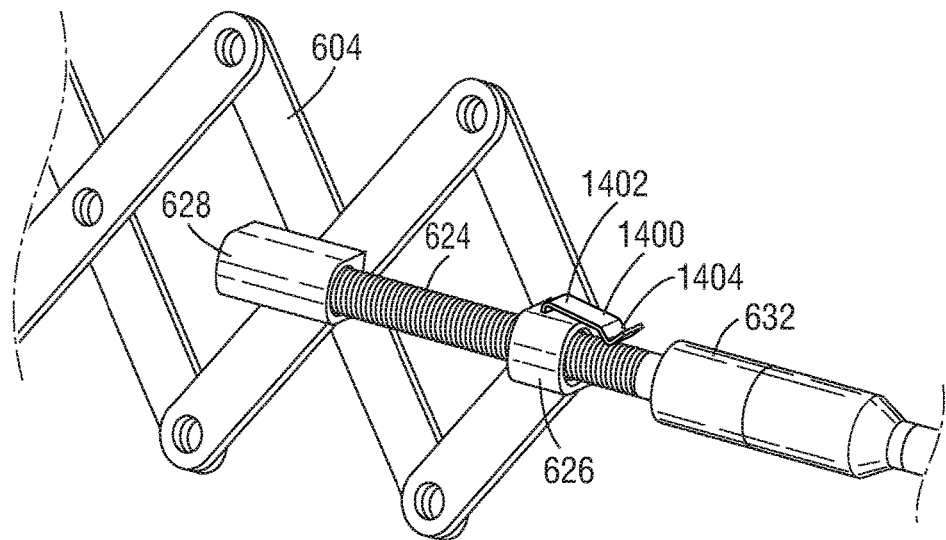
FIGS. 39-41 show the frame and the screw of FIG. 38 with an exemplary spring lock to prevent inadvertent rotation of the screw after the frame is locked.
Figure 40:
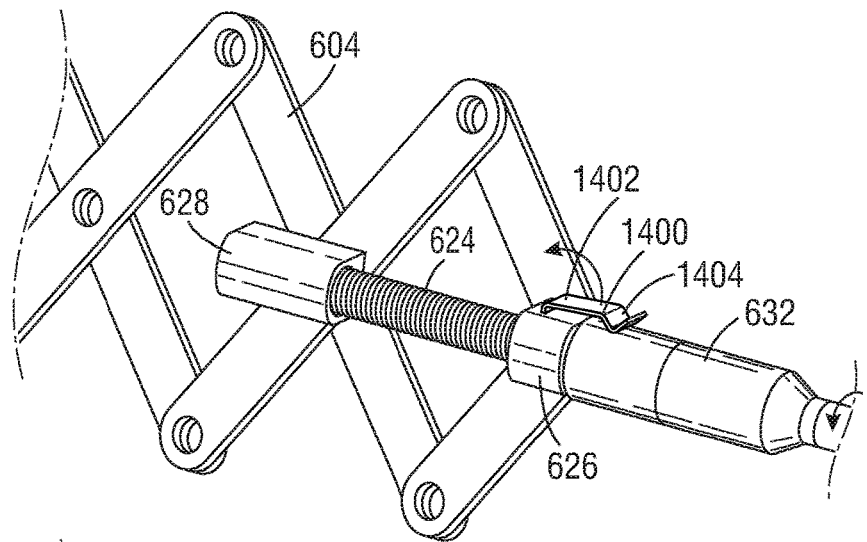
Figure 41:
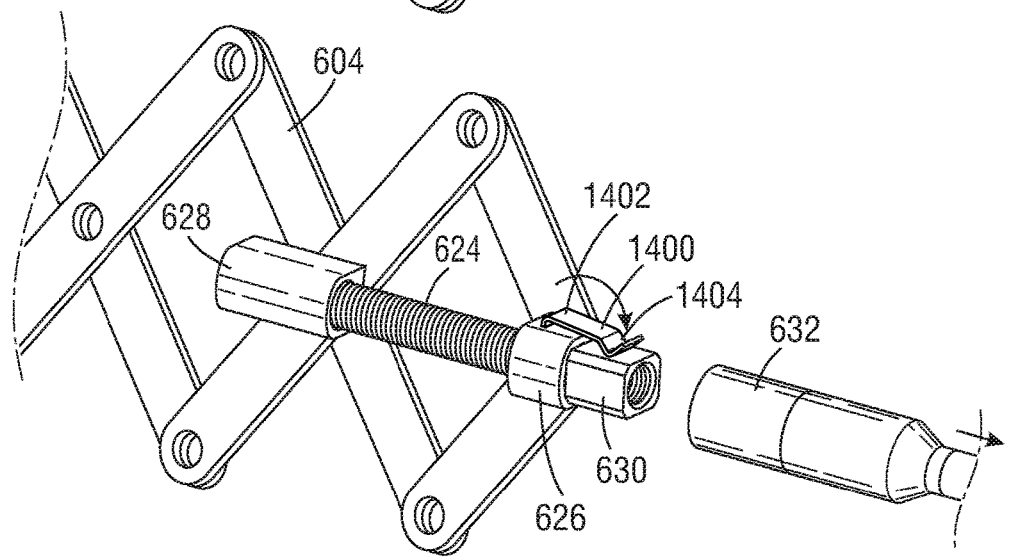

FIGS. 39-41 show an example of a locking member comprising a biased spring lock 1400 that can be affixed to a proximal nut 626 to resist rotation of the locking screw 624 after the locking screw is moved into a position for retaining the frame 604 in the expanded state. FIG. 39 shows the frame 604, the locking screw 624, and the tool head 632 before the frame is placed in the locked position. In FIG. 39, the tool head 632 is positioned around the screw head 630 (not shown in FIG. 39) such that the tool head can be rotated to advance the locking screw 624 to a locked position where the screw head 630 abuts against the proximal nut 626.

The spring lock 1400 can be in the form of a leaf spring as shown and can have a fixed end portion 1402 secured to the nut 626 and a free end portion 1404 that is biased inwardly toward the screw 624 such that it exerts a radially inward directed force towards the locking screw 624. As the tool head 632 is rotated and advanced distally, the shape of the spring lock 1400 is such that the tool head can slide under the free end portion 1404, pushing the spring lock away from the locking screw 624, as shown in FIG. 40. While the tool head 632 is positioned between the screw 624 and the spring lock 1400, the circular shape of the tool head allows it to be easily rotated despite the presence of the spring lock since very little surface area of the tool head is in contact with the spring lock.

When the tool head 632 has fully advanced the screw head 630 against the proximal nut 630, tool head 632 can be removed from the screw head as shown in FIG. 41. This causes the free end portion 1404 of the spring lock 1400 to press against the screw head 630. Due to the flat surface of the screw head 630 and the pressure exerted against the screw head by the spring lock 1400, the torque required to further rotate the screw 624 is increased. The pressure exerted by the spring against the screw head further resists rotation of the screw (and loosening of the screw) against dynamic vibrational loads on the screw. The spring can be selected to have a stiffness sufficient to resist further rotation of the screw under the load applied by the user to rotate the screw into the locked position.

In another example, the spring can be selected to have a stiffness that would still allow an operator to rotate the locking screw 624 from its locked position with a predefined torque while still resisting rotation of the screw caused by vibrational loads. In alternative embodiments, a spring lock can be affixed to a location on the frame other than the nut 626. For example, a spring lock can be affixed to a strut of the frame at a location where the spring lock can engage the screw head 630.

Figure 42:
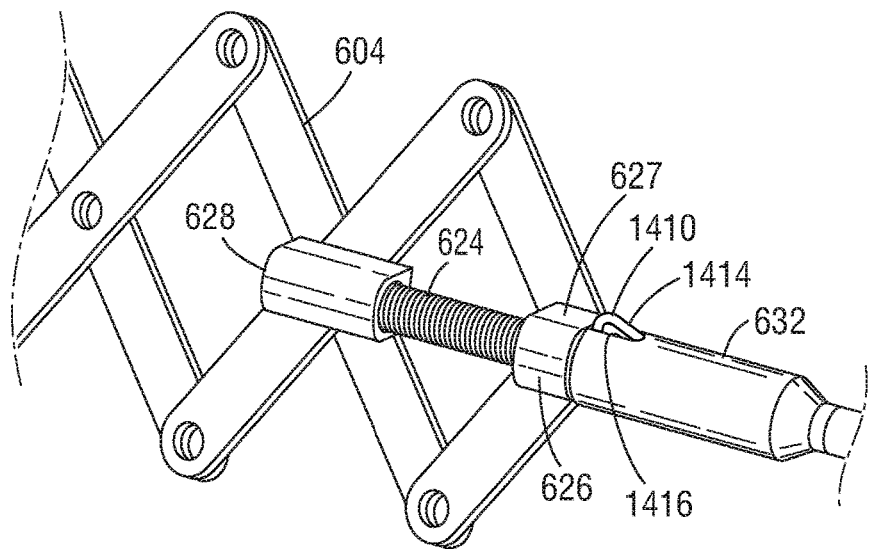
FIGS. 42-43 show the frame and the screw of FIG. 38 with another exemplary spring lock.
Figure 43:
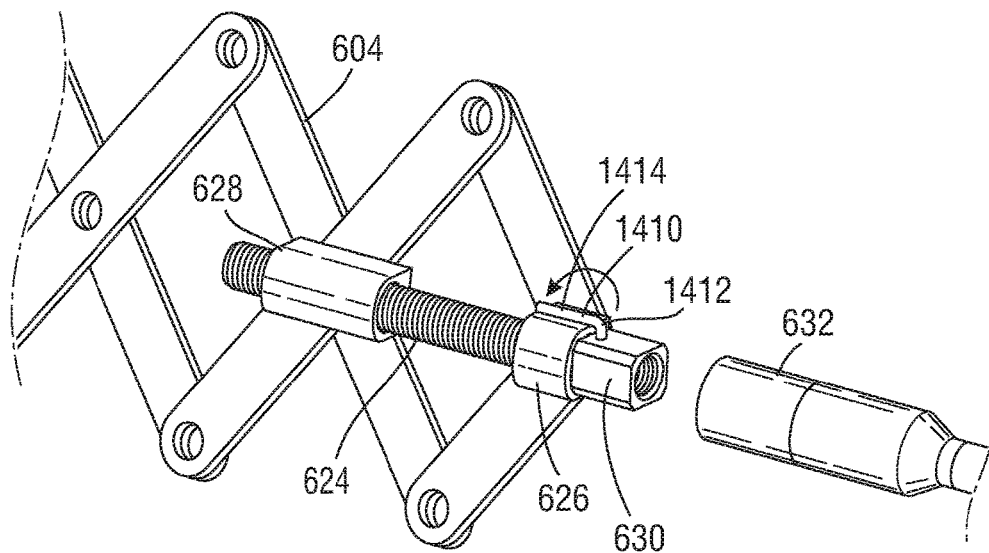

FIGS. 42-43 show an alternative example of a biased spring lock 1410 that can be used to resist rotation of the locking screw 624 after the prosthetic valve is expanded and the locking screw is moved to the locked position. In the example of FIGS. 42-43, the spring lock 1410 has a fixed end portion 1412 that is affixed to the screw head 630 rather than the proximal nut 626 as in the example of FIGS. 39-41, and a free end portion 1414. The spring lock 1410 is biased against the nut 626. The spring lock 1410 is configured to be held by the tool head 632 in a first, non-engaged position away from the nut 626 against the force of the spring lock 1410 and when released from the tool head 632, the spring lock can revert to a second, engaged position with the free end portion 1414 bearing against the nut 626.

FIG. 42 shows the frame 604 and the locking screw 624 as the tool head 632 is in position to rotate the locking screw into a locked position abutting against the proximal nut 626. As shown, the tool head 632 can include a slot or opening 1416 sized to receive the free end portion of the spring lock and hold it in the non-engaged position. After the screw head 630 is moved into a locked position abutting against the proximal nut 626, the tool head 632 can be removed from the screw head as shown in FIG. 43 (and as previously described). This causes the spring lock 1410 to be released from the tool head 632 and causes the spring lock to spring back and press against the proximal nut 626. The spring lock exerts sufficient pressure against the nut 626 to resist rotation of the screw 624 caused by vibrational loads. The nut 626 can be formed with a flattened surface 627 that is contacted by the spring lock to enhance resistance against rotation of the screw.

Figure 44:
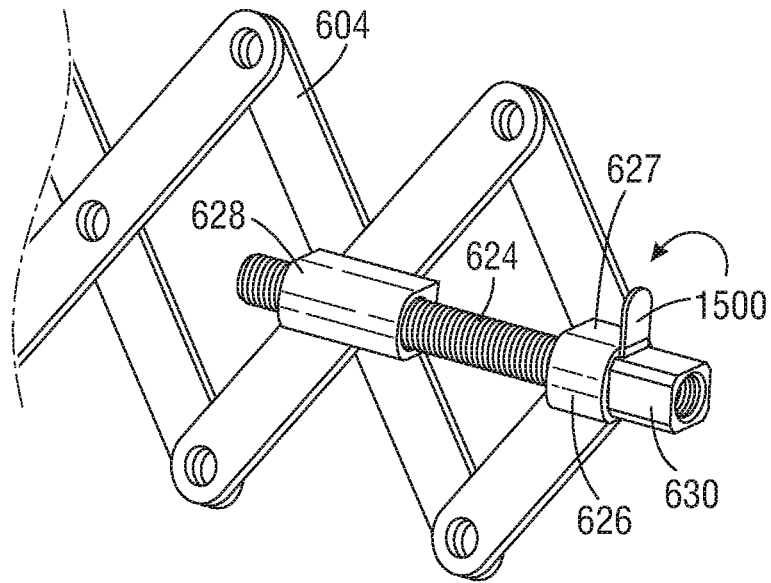
FIGS. 44-45 show the frame and the screw of FIG. 38 with an exemplary permanent bend lock.
Figure 45:
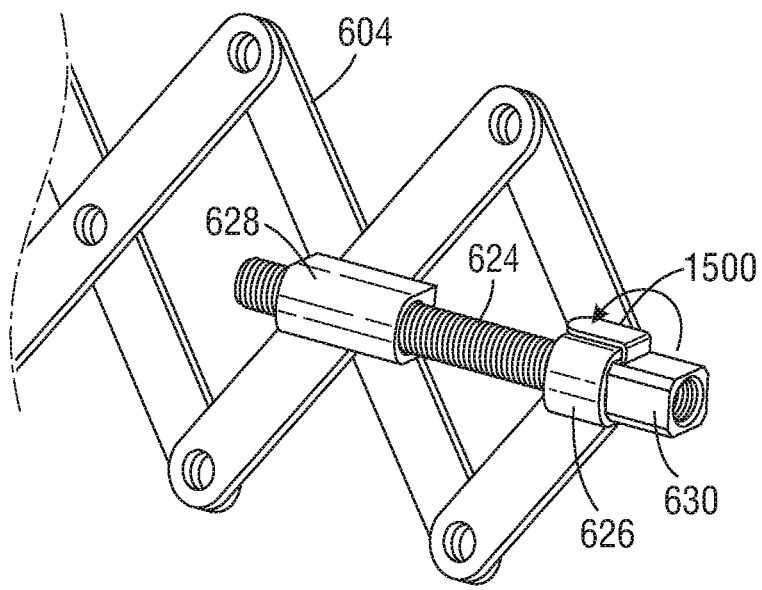

FIGS. 44-45 show an example of a plastically deformable locking member 1500 that can be used to resist rotation of the locking screw 624. The locking member 1500 in the illustrated configuration comprises a bendable flange that is fixed at one end to the screw head 630. FIG. 44 shows the screw 624 in a locked position with the screw head 630 abutting against the proximal nut 626. Once the screw head 630 is in place, the locking member 1500 can be bent against the proximal nut 626 by an external force as shown in FIG. 45. The locking member 1500 is plastically deformed when bent and therefore retains its shape against or adjacent the nut 626. Once the locking member 1500 is bent into the position as shown in FIG. 45, the locking member 1500 resists rotation of the locking screw 624 caused by random vibrational forces.

The locking member 1500 can have a flat profile that corresponds to the flat surface 627 of the nut 626. However, the locking member and/or the nut can have other shapes in alternative embodiments. For example, the locking member 1500 can be sized and shaped to be received in a correspondingly shaped recess or opening in the nut.

The locking member 1500 can be bent by the locking tool 632 (not shown in FIGS. 44-45) by, for example, pushing the locking tool or a separate pushing member against the flange while the screw head is abutted against the proximal nut 626. In other examples, other methods of bending the flange 1500 can be used. The locking member can comprise a plastically deformable material, such as stainless steel, and can be formed as part of the screw head 630 or separately formed and attached (e.g., by welding) to the screw head. In alternative embodiments, the locking member can be affixed to the nut 626 or at another convenient location of the frame and is then bent against the screw head 630 to resist rotation of the screw.

Figure 46:
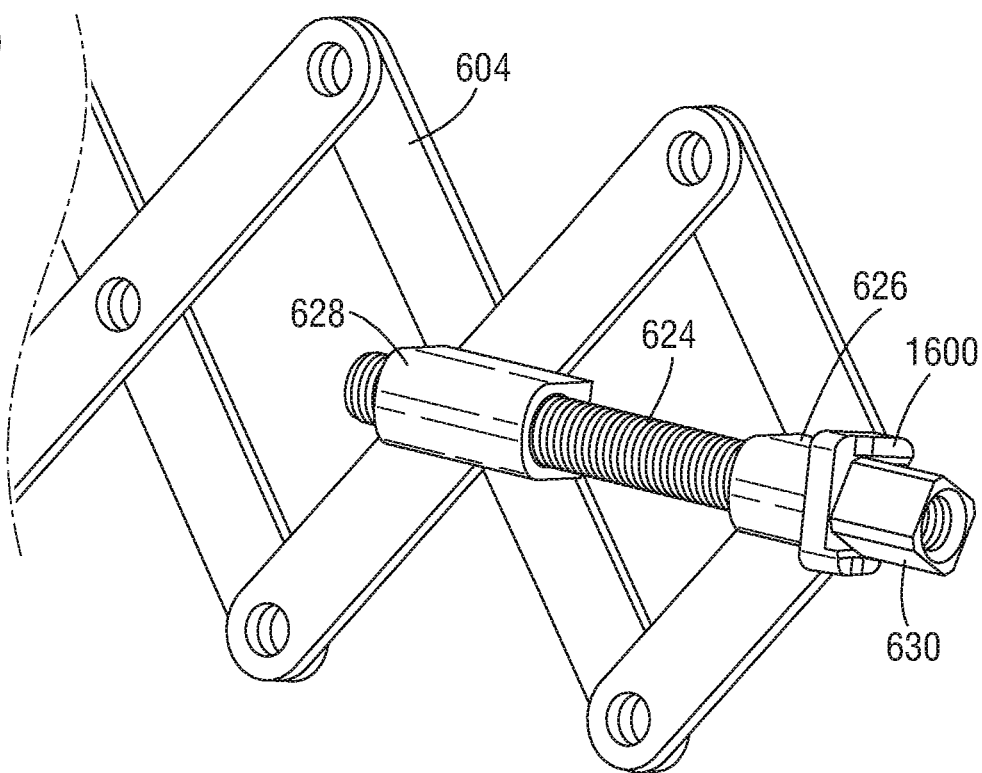
FIG. 46 shows the frame and the screw of FIG. 38 with an exemplary ratchet lock.

In particular embodiments, a valve assembly can incorporate a ratchet lock system configured to permit rotation of a locking screw in one direction to place the screw in a locked position and resist rotation of the screw in the opposite direction. FIG. 46 shows an example of a ratchet lock 1600 configured to resist rotation of the screw 624 after the screw is placed in a locked position after valve expansion. The ratchet lock 1600 in the illustrated embodiment is attached to the proximal end of a proximal nut 626 and positioned to engage the screw head 630. In some implementations, the proximal nut 626 and the ratchet lock 1600 can be manufactured as a single piece. In other implementations, the ratchet lock 1600 can be separately formed and then attached to the nut 626 (e.g., by welding). In still other implementations, the ratchet lock 1600 can be mounted to the frame 604 apart from the nut 626; that is, the ratchet lock 1600 need not be mounted directly on the nut as long as it is positioned to engage the screw head 630. The ratchet lock 1600 is formed with one or more ratcheting features that are configured to engage the screw head 630 and allow rotation of the locking screw 624 in one direction to allow a user to move the locking screw to its locked position but resist rotation of the locking screw in the opposition direction.

Figure 47A:
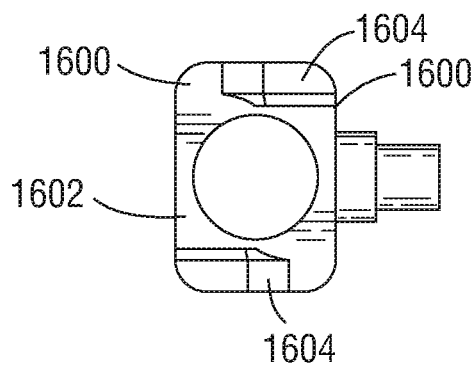
FIGS. 47A-47D show various views of the ratchet lock of FIG. 46.
Figure 47B:
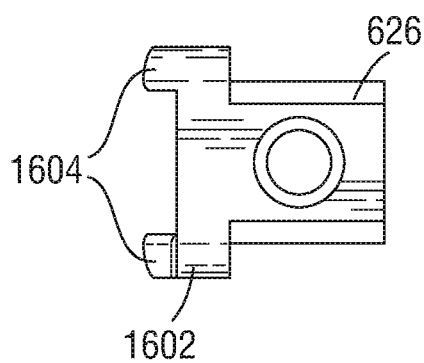
Figure 47C:
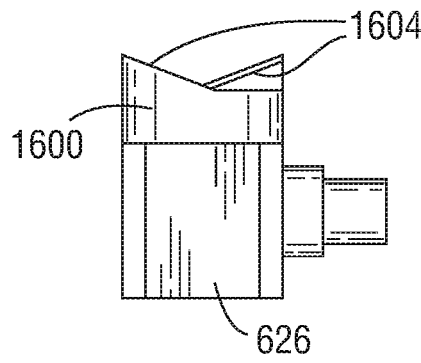
Figure 47D:
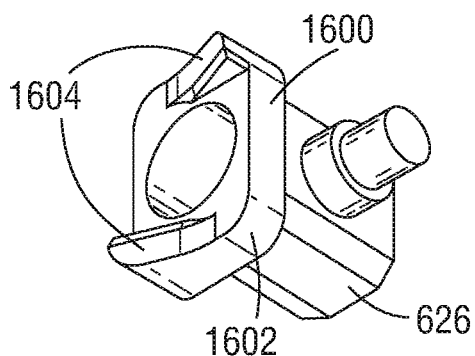

FIGS. 47A-47D show various views of the proximal nut 626 and the attached ratchet lock 1600. The ratchet lock 1600 in the illustrated configuration can have a base member 1602 and one or more ratcheting features in the form of one or more ratchet teeth 1604 extending from the base member 1602. As best shown in FIG. 47D, the ratchet teeth 1604 can be positioned on opposite corners of the base member 1602 and project outwardly from the base member and have angled surfaces that engage the screw head 630.

The spacing between the teeth 1604 can be slightly greater than the width of the screw head 630. In use, as the locking screw 624 is rotated toward its locked position (e.g., in a clockwise direction), the screw head 630 will come in contact with the teeth 1604. Due to the angled surfaces of the teeth 1604, the screw head can be further rotated in the same direction toward the locked position until the screw head is positioned between the teeth 1604, as depicted in FIG. 46. The teeth 1604 can be sized and shaped such that a predetermined torque applied to the screw by the user allows the screw to be placed in its locked position. Once the screw head 630 is between the teeth, rotation of the screw head (and therefore the locking screw) in the opposite direction (e.g., counterclockwise) is resisted by the contact between teeth and the screw head. In this manner, the ratchet lock 1600 resists rotational movement of the locking screw 624 that can be caused by vibrational forces.

Although two ratchet teeth are shown in the illustrated embodiment, a fewer or greater number of teeth can be used. Also, in alternative embodiments, the screw head 630 can be formed with one or more ratcheting features (e.g., teeth 1604) that engage an adjacent surface of the nut 626 or another component of the frame (without using the ratchet lock 1600). In some embodiments, one or more ratcheting features on the screw head can be adapted to engage one or more ratcheting features on a ratchet lock 1600 or on another component of the frame.

Figure 48:
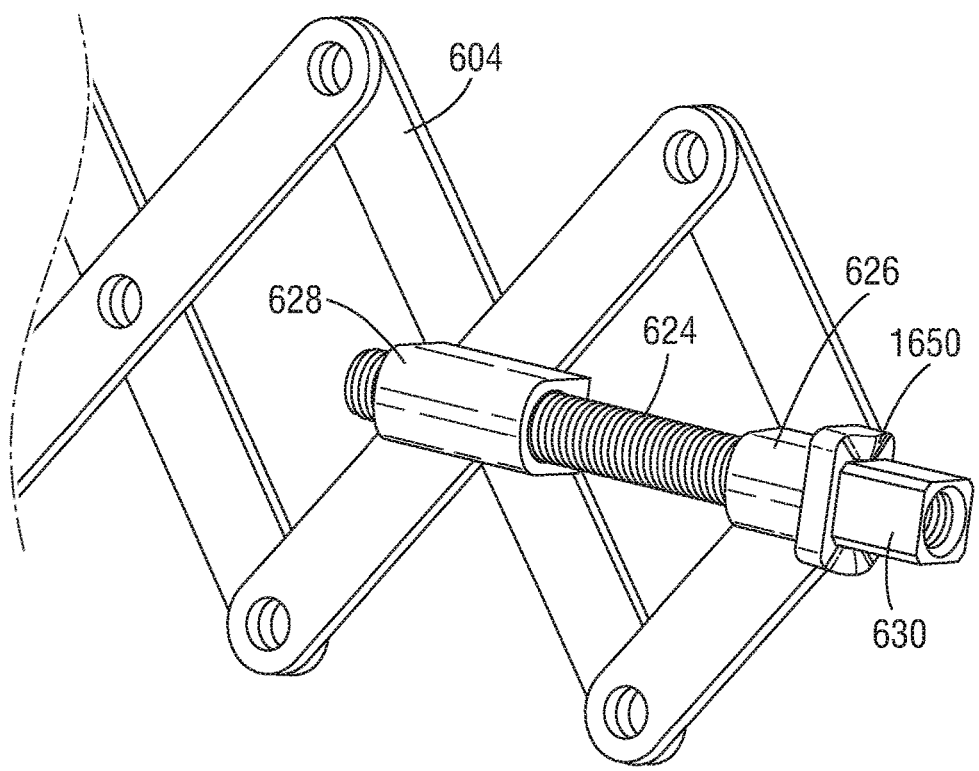
FIG. 48 shows the frame and the screw of FIG. 38 with a click lock.

FIG. 48 shows an example of a "click lock" system that can be used to resist rotation of the locking screw 24 after it is placed in a locked position. The exemplary click lock system of FIG. 48 is the same as the exemplary ratchet lock system of FIG. 46 except that the ratchet lock 1600 is replaced with click lock 1650, which in the illustrated configuration comprises a base member 1652 and one or more teeth or projections 1654, 1656. As described above with respect to the ratchet lock 1600, the click lock 1650 can be integrally formed as part of the nut 626, or it can be a separate component mounted on the nut or on another location on the frame 604.

Figure 49A:
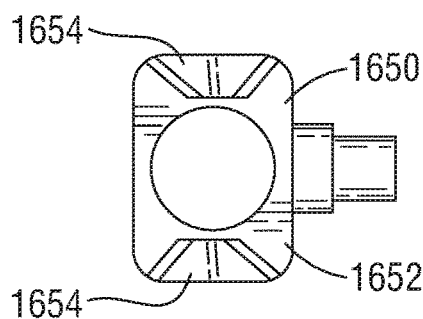
FIGS. 49A-49D show various views of the click lock of FIG. 48.
Figure 49B:
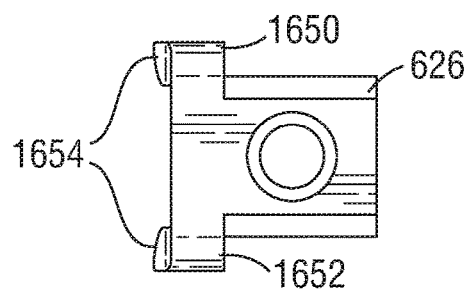
Figure 49C:
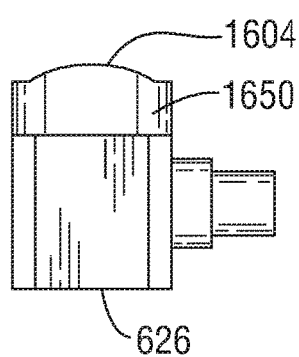
Figure 49D:
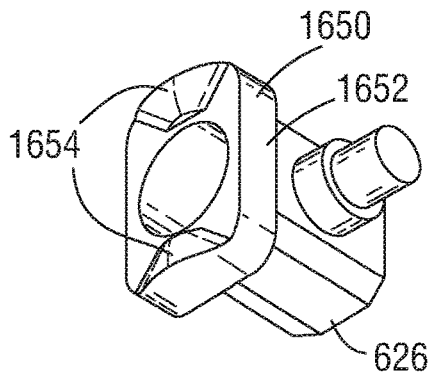

FIGS. 49A-49D show various views of a proximal nut 626 and the attached click lock 1650. As best shown in FIG. 49D, each of the teeth has a convex surface projecting outwardly from the base member 1652. The teeth 1654 are sized and shaped to permit rotation of the screw head in both directions when a predetermined torque is applied to the screw by the user. In the illustrated example, upon application of a predetermined torque to the screw, the screw head 630 can rotate over the surfaces of the teeth 1654 in both directions causing a "click" with every 90 degrees of rotation. However, the engagement of the teeth with the screw head will resist rotation of the screw if the predetermined torque is not exceeded. In this manner, rotational movement of the screw caused by vibrational loads can be resisted.

It should be understood that the click lock need not make an audible clicking noise when rotated. In the context of the present disclosure, a click lock provides resistance against rotation at one or more rotational orientations of the click lock relative to the component engaging the click lock (e.g., the screw head), or vice versa. When the rotated component overcomes the resistance, the torque required to rotate that component decreases. The increasing and decreasing resistance against torqueing of the screw can provide tactile feedback to the user as to the rotational orientation of the screw, which can feel like the screw is "clicking" as it is rotated.

Any of the locking mechanisms discussed above in connection with FIGS. 39-49 can be used to apply resistance against rotation of a screw that is used to produce radial expansion and compression of the frame of a prosthetic valve. For example, any of these locking mechanisms can be used in connection with the screws 900 in the prosthetic valve 1800 of FIG. 51.

Figure 50:
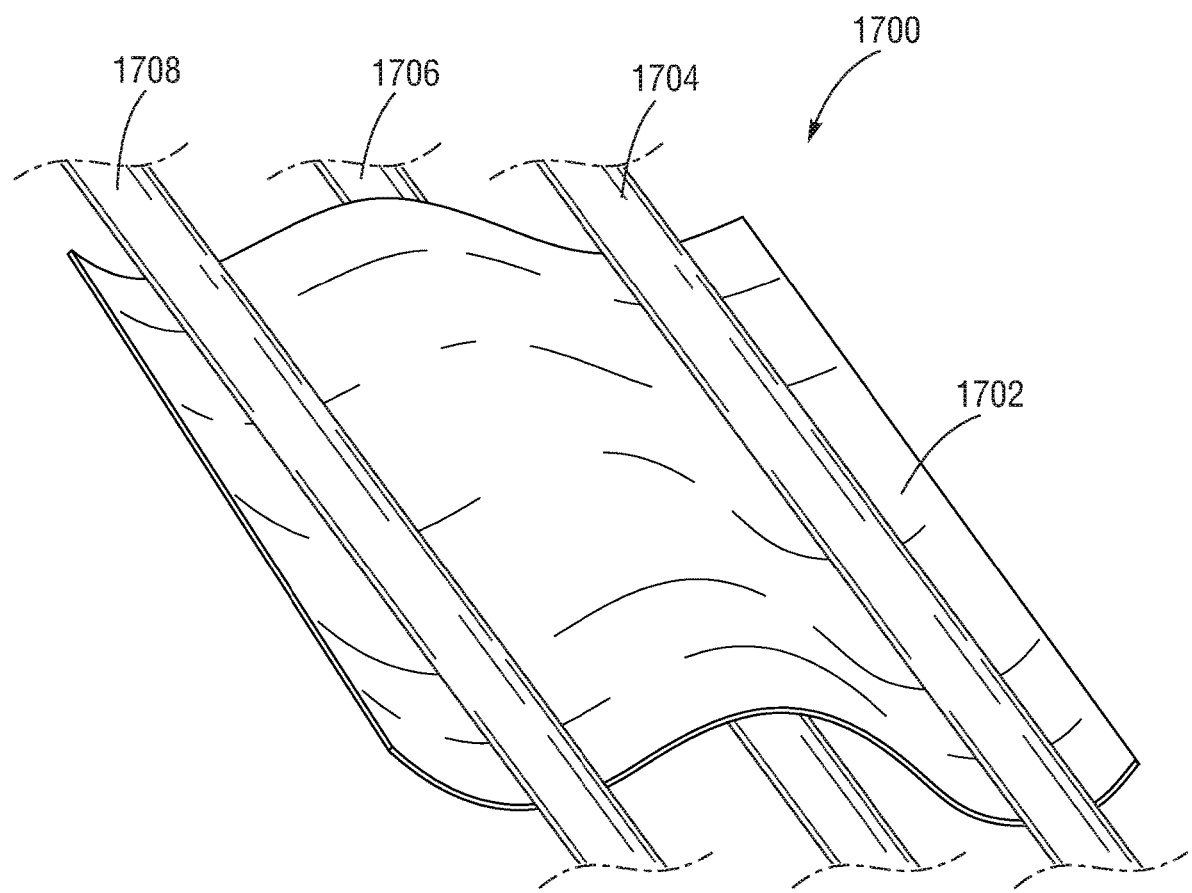
FIG. 50 shows an alternative exemplary frame of a prosthetic heart valve and a skirt.

FIG. 50 shows alternative embodiment of a frame 1700 and a skirt 1702 of a prosthetic heart valve. The skirt 1702 can be constructed from any of the materials described above in connection with skirt 50 of FIG. 2. The skirt 1702 can function as a sealing member to help establish a seal with surrounding tissue, similar to the skirt 50. The skirt 1702 can also help secure a leaflet assembly (e.g., leaflet assembly 48) inside the frame, such as by suturing the inflow edges of the leaflets to the skirt 802.

The frame 1700 can be constructed similarly to frame 22 of FIG. 2. The frame 1700 can have a plurality of diagonally extending, parallel struts 1704, 1706, and 1708 that are pivotably connected to struts that extend perpendicularly to the struts 1704, 1706, 1708, similar to frame 22 of FIG. 2 and frame 200 of FIG. 4. For purposes of illustration, only three struts 1704, 1706, 1708 of the frame are shown.

The skirt 1702 can be supported on the frame 1700 by weaving the skirt through the struts 1704, 1706, 1708 of the frame such that portions of the skirt are positioned on the inner surfaces of struts and portions of the skirt are positioned on the outer surfaces of the struts. For example, in the illustrated embodiment, the skirt 1702 is positioned on the inner surfaces of struts 1704, 1708 and on the outer surface of struts 1706. Alternatively, the skirt 1702 can be positioned on the outer surface of struts 1704, 1708 and on the inner surface of struts 1706.

The struts of the frame 1700 can be connected together using fasteners, such as fasteners 40 of FIG. 2. The skirt 1702 can be placed between the struts during the process of assembling the struts to form the frame. In the illustrated embodiment of FIG. 27, the fasteners used to connect the struts of frame 1700 together can extend through the skirt 1702 to hold the skirt in place on the struts without the use of sutures. For example, the skirt 1702 can be formed with pre-formed holes sized to receive the fasteners 40, or alternatively, the fasteners can be pressed through and puncture the skirt material during the assembly process. In lieu of or in addition to the use of the fasteners, sutures can be used to secure the skirt 1702 to the frame 1700.

Further examples:

1. A prosthetic valve delivery assembly, comprising:

a prosthetic valve comprising a radially expandable and compressible expandable frame and a plurality of locking units coupled to the frame at circumferentially spaced locations, each locking unit comprising a respective first coupling member and a locking member; and a delivery apparatus comprising:

a plurality of elongate positioning members, each of the positioning members comprising a respective second coupling member at a distal end thereof, each second coupling member being releasably coupled to a respective first coupling member;

a plurality of elongate actuation members, each of the actuation members having a distal end portion coupled to the frame; and a plurality of release members, each of the plurality of release members coaxially disposed with respect to, and engaged with, one of the locking units;

wherein moving the positioning members or the actuation members axially relative to one another causes the frame to expand or contract, and retracting the release members proximal to the locking members of the locking units causes the locking members to move to a locked position to resist contraction of the frame and retracting the release members proximal to the first coupling members of the locking units causes the first coupling members to decouple from the second coupling members, thereby permitting the positioning members to decouple from the locking units.

2. The delivery assembly of example 1, further comprising a handle coupled to proximal end portions of the first and second actuation members, the handle comprising a first actuator configured to produce axial movement of the positioning members.

3. The delivery assembly of example 2, wherein the handle comprises a second actuator configured to produce axial movement of the release members relative to the positioning members and the actuation members.

4. The delivery assembly of any preceding example, wherein each of the locking members comprises a pair of deflectable locking jaws disposed about one of the actuation members.

5. The delivery assembly of any preceding example, wherein each of the first coupling members comprises a tab and a notch and each of the second coupling member comprises a tab and a notch, the tab of the first coupling member received in the notch of the second coupling member and the tab of the second coupling member received in the notch of the first coupling member.

6. The delivery assembly of example 5, wherein the tab of the second coupling member comprises an axially extending slot.

7. The delivery assembly of example 1, wherein the actuation members comprise a plurality of tethers.

8. The delivery assembly of any preceding example, further comprising a plurality of cutting members configured to sever the actuation members at locations proximal to the locking units.

9. The delivery apparatus of any one of examples 1-8, wherein each of the actuation members comprises a plurality of longitudinally spaced apart protrusions configured to engage one of the locking members of one of the locking units.

10. The delivery assembly of any preceding example, wherein each of the locking units comprises an elongate first member coupled to a proximal end of the frame and an elongate second member coupled to a distal end of the frame, the first and second members being axially moveable relative to each other.

11. The delivery assembly of example 10, wherein each of the first members of the locking units is releasably coupled to one of the positioning members and each of the second members is releasably coupled to one of the actuation members.

12. The delivery assembly of example 11, wherein retracting the release members proximal to the locking units is effective to decouple the second members of the locking units from the actuation members.

13. The delivery assembly of any of examples 10-12, wherein each of the first members of the locking units comprises a first locking feature and each of the second members of the locking units comprises a second locking feature, and retracting the release members proximal to the locking units causes the first locking feature to engage the second locking feature to resist relative axial movement between the first and second members and contraction of the frame.

14. The delivery assembly of example 13, wherein each of the first locking features comprises a deflectable locking bar and each of the second locking features comprises at least one aperture sized to receive a locking bar.

15. The delivery assembly of any of examples 10-14, wherein the first member of each locking unit is pivotably connected to an apex at the proximal end of the frame and the second member of each locking unit is pivotably connected to an apex at the distal end of the frame.

16. The delivery assembly of any preceding example, wherein the frame comprises a plurality of interconnected struts having a plurality of linear segments that are laterally offset from each other in a direction perpendicular to the lengths of the struts.

17. The delivery assembly of example 16, wherein the struts are connected to each other at locations between the linear segments.

18. The delivery assembly of example 17, wherein the struts are hingeably coupled to each other by pins extending through the struts at the locations between the linear segments.

19. The delivery assembly of any one of examples 1-9 and 16-18, wherein each of the actuation members extends coaxially through one of the positioning members.

20 The delivery assembly of any one of examples 1-9 and 16-18, wherein each of the release members extends through one of the locking units and coaxially between one of the positioning members and one of the actuation members.

21. The delivery assembly of any one of examples 1-9 and 16-18, wherein the first coupling member of each of the plurality of locking units comprises a radially-outwardly biased fin and wherein each of the release members is disposed about a positioning member and a first coupling member.

22. A prosthetic valve comprising:
a radially expandable and compressible frame comprising a plurality of interconnected struts, each strut having a first end, a second end, and a length extending from the first end to the second end, each strut comprising a plurality of linear segments that are laterally offset from each other in a direction perpendicular to the lengths of the struts; and
a valvular structure mounted to the frame and configured to regulate the flow of blood through the prosthetic valve.

23. The prosthetic valve of example 22, wherein each of the plurality of struts is hingeably connected to at least another of the plurality of struts.

24. The prosthetic valve of example 22 or 23, further comprising a spacer disposed between a pair of connected struts.

25. The prosthetic valve of any of examples 22-24, wherein the struts are connected to each other by pins extending through the struts.

26. The prosthetic valve of any of examples 22-25, wherein the frame comprises a plurality of circumferentially spaced locking units configured to lock the frame in a radially expanded state.

27. A method of delivering a prosthetic valve, the method comprising:
inserting a distal end of an elongate delivery apparatus into a patient, the elongate delivery apparatus releasably coupled to the prosthetic valve, the prosthetic valve comprising an expandable frame comprising a plurality of locking units;
axially moving a plurality of elongate positioning members of the delivery apparatus to expand the prosthetic valve to an expanded state of a desired size;
removing a plurality of elongate release members from the plurality of locking units, causing the positioning members to decouple from the frame and the locking units to lock the frame in the expanded state; and
removing the elongate delivery apparatus from the patient.

28. The method of example 27, wherein removing the release members from the locking units allows first coupling members of the actuation members to decouple from corresponding second coupling members of the locking units.

29. The method of example 27 or 28, wherein:
axially moving a plurality of elongate actuation members of the delivery apparatus comprises axially moving a first plurality of actuation members relative to a second plurality of actuation members of the delivery apparatus to expand the prosthetic valve; and
removing the release members from the locking units allows the first and second actuation members to decouple from the frame.

30. An assembly comprising:
a prosthetic valve comprising a radially expandable and compressible annular frame;
at least one linear actuator assembly coupled to the frame and configured to apply a distally directed force and/or a proximally directed force to the frame to radially expand or compress the frame; and
at least one locking mechanism coupled to the frame comprising a first sleeve member connected to the frame at a first location, a second sleeve member having internal threads and being connected to the frame at a second location, and a first screw configured to engage the internal threads of the second sleeve member to retain the frame in a radially expanded state.

31. The assembly of example 30, wherein the at least one linear actuator assembly is releasably coupled to the frame.

32. The assembly of example 30, wherein the at least one linear actuator assembly comprises an actuator member configured to be releasably coupled to the frame.

33. The assembly of example 32, wherein the at least one linear actuator assembly comprises a first threaded member connected to a distal end portion of the actuator member, the first threaded member being configured to releasably engage a second threaded member connected to the frame.

34. The assembly of example 33, wherein the first threaded member comprises a second screw and the second threaded member comprises an internally threaded nut.

35. The assembly of any of examples 32-34, wherein the actuator member comprises a cable.

36. The assembly of any of examples 32-35, wherein the at least one linear actuator assembly further comprises a sleeve positioned annularly around the actuator member.

37. The assembly of any of examples 32-36, further comprising:
an annular stopper connected to the frame, wherein the actuator member extends through the stopper;
wherein the at least one linear actuator assembly comprises a support tube positioned annularly around the actuator member and the stopper is configured to engage a distal end of the support tube and prevent the support tube from moving distally beyond the stopper in an axial direction.

38. The assembly of any of examples 30-37, further comprising a locking tool configured to be releasably coupled to the first screw, the locking tool comprising a tool head configured to engage and produce rotation of the first screw when the locking tool is coupled to the first screw such that the first screw moves axially through the first sleeve member and the second sleeve member.

39. The assembly of example 38, wherein the first screw has a screw head at its proximal end and wherein a shape of the tool head is configured to correspond to a shape of the screw head such that the tool head is operable to couple with the screw head such that rotation of the tool head causes rotation of the first screw.

40. The assembly of example 39, wherein the screw head and the first sleeve member are configured such that the screw head is prevented from moving distally beyond the first sleeve member in an axial direction.

41. The assembly of any of examples 38-40, wherein the at least one locking mechanism further comprises an inner shaft extending partly within a lumen of the tool head, the inner shaft having a threaded surface at its distal end, the screw head having internal threads, and the inner shaft being configured such that its threaded surface engages the internal threads of the screw head.

42. The assembly of any of examples 39-41, wherein the first screw further comprises a rigid portion and a flexible portion positioned between the screw head and the rigid portion.

43. The assembly of example 42, wherein the flexible portion of the first screw comprises braded cable.

44. The assembly of example 42, wherein the flexible portion of the first screw comprises hypotube.

45. The assembly of any of examples 39-41, wherein the first screw further comprises a rigid portion connected to the screw head, a flexible portion connected to a distal end of the rigid portion, and a stopper connected to a distal end of the flexible portion.

46. The assembly of any of examples 39-45, further comprising a spring lock attached to the first sleeve member, wherein the spring lock is configured to exert a radially inward directed force against the screw head to resist rotation of the screw.

47. The assembly of any of examples 39-45, further comprising a spring lock attached to the screw head, wherein the spring lock is configured to exert a radially inward directed force against the first sleeve member to resist rotation of the screw.

48. The assembly of any of examples 39-45, further comprising a flange attached to the screw head, wherein the flange is configured to bend against the first sleeve member to resist rotation of the screw.

49. The assembly of any of examples 39-45, further comprising a ratchet lock attached to a proximal end of the first sleeve member, wherein the ratchet lock comprises teeth configured to allow rotation of the screw head in a first direction and prevent rotation of the screw head in a second direction.

50. The assembly of any of examples 39-45, further comprising a click lock attached to a proximal end of the first sleeve member, wherein the click lock comprises teeth configured to resist rotation of the screw by an amount less than 90 degrees and to click when the screw is rotated 90 degrees.

51. An assembly comprising:
 a prosthetic valve comprising a radially expandable and compressible annular frame; and
 at least one expansion and locking mechanism comprising:
  a linear actuator connected to the frame, wherein the linear actuator is configured to apply a distally directed force and/or a proximally directed force to the frame to radially expand or compress the frame; and
  a rotating member coaxially positioned relative to the linear actuator configured to retain the frame in a radially expanded state.

52. The assembly of example 51, further comprising:
 a first sleeve member connected to the frame at a first location; and
 a second sleeve member having internal threads and being connected to the frame at a second location;
 wherein the linear actuator is releasably coupled to the frame;
 wherein the rotating member is a screw configured to engage the internal threads of the second sleeve member; and
 wherein the linear actuator extends through a lumen of the screw.

53. The assembly of example 52, further comprising a locking tool that is configured to be releasably coupled to the screw and rotate the screw such that the screw moves axially through the first sleeve member and the second sleeve member when the locking tool is coupled to the screw.

54. The assembly of example 53, wherein the locking tool and the first sleeve member are configured such that the locking tool is prevented from moving distally beyond the first threaded member in an axial direction.

55. The assembly of any of examples 52-54, wherein the screw has a screw head at its proximal end and wherein the screw head and the first member are configured such that the screw head is prevented from moving distally beyond the first sleeve member in an axial direction 56. The assembly of example 51, wherein the linear actuator is an actuator screw having external threads and is connected to the frame at a first location;
 wherein the assembly further comprises a sleeve connected to the frame at a second location;
 wherein the actuator screw extends through a lumen of the sleeve;
 wherein the rotating member is a locking nut having internal threads configured to engage the threads of the actuator screw; and
 wherein the sleeve and the locking nut are configured such that the locking nut is prevented from moving distally beyond the sleeve in an axial direction.

57. The assembly of example 56, wherein the actuator screw comprises a first portion and a second portion, wherein a diameter of the second portion is less than a diameter of the first portion.

58. The assembly of example 57, wherein the assembly further comprises an annular actuator member having internal threads configured to engage the threads of the second portion of the actuator screw such that when the internal threads of the actuator member are engaged with the threads of the second portion of the actuator screw, axial movement of the actuator member results in axial movement of the actuator screw.

59. The assembly of any of examples 57-58, further comprising a locking tool positioned within a lumen of the sleeve, wherein the locking tool has a notched portion at its distal end configured to engage a corresponding notched portion at a proximal end of the locking nut such that rotation of the locking tool in a clockwise direction causes rotation of the locking nut in a clockwise direction.

60. The assembly of example 59, wherein the locking tool has an internally threaded surface to engage the threads of the actuator screw.

61. The assembly of example 59, further comprising a support tube positioned annularly around the locking tool, wherein a proximal end of the sleeve is configured to engage a distal end of the support tube such that the support tube is prevented from moving distally beyond the proximal end of the sleeve in an axial direction.

62. The assembly of any of examples 30-61, further comprising a skirt, wherein the frame comprises a plurality of rows of struts, and wherein the skirt is positioned inside of at least one row of struts and outside of at least another row of struts.

63. An implantable prosthetic valve comprising:
 an annular frame comprising a plurality of rows of struts and being radially collapsible and expandable between a radially collapsed configuration and a radially expanded configuration; and
 a skirt weaved around the struts such that the skirt is positioned inside of at least one row of struts and outside of at least another row of struts.

64. A method of implanting a prosthetic heart valve, the method comprising:
 inserting the prosthetic heart valve into a patient's vasculature, the prosthetic heart valve being coupled to a distal end portion of a linear actuator, wherein the prosthetic heart valve comprises a frame in a radially compressed state;
 actuating the linear actuator to expand the frame to a radially expanded state; and
 rotating a screw to advance the screw through first and second members on the frame to retain the prosthetic valve in the radially expanded state.

65. The method of example 64, wherein the act of rotating the screw comprises rotating a locking tool coupled to the screw, and then de-coupling the locking tool from the screw after the screw is advanced through the first and second members.

66. The method of any of examples 64-65, further comprising de-coupling the linear actuator from the frame.

67. The method of example 66, wherein the act of de-coupling the linear actuator comprises unscrewing a threaded portion of the linear actuator from a corresponding threaded portion of the frame.

68. The method of any of examples 64-67, wherein the act of actuating the linear actuator comprises applying a proximally directed force to a distal portion of the frame with a cable.

General Considerations

It should be understood that the disclosed embodiments can be adapted to deliver and implant prosthetic devices in any of the native annuluses of the heart (e.g., the pulmonary, mitral, and tricuspid annuluses), and can be used with any of various delivery approaches (e.g., retrograde, antegrade, transseptal, transventricular, transatrial, etc.). The disclosed embodiments can also be used to implant prostheses in other lumens of the body. Further, in addition to prosthetic valves, the delivery assembly embodiments described herein can be adapted to deliver and implant various other prosthetic devices such as stents and/or other prosthetic repair devices.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved. The technologies from any example can be combined with the technologies described in any one or more of the other examples. In view of the many possible embodiments to which the principles of the disclosed technology may be applied, it should be recognized that the illustrated embodiments are only preferred examples and should not be taken as limiting the scope of the disclosed technology.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

As used herein, the terms "integrally formed" and "unitary construction" refer to a construction that does not include any welds, fasteners, or other means for securing separately formed pieces of material to each other.

As used herein, operations that occur "simultaneously" or "concurrently" occur generally at the same time as one another, although delays in the occurrence of one operation relative to the other due to, for example, spacing, play or backlash between components in a mechanical linkage such as threads, gears, etc., are expressly within the scope of the above terms, absent specific contrary language.

In view of the many possible embodiments to which the principles of the disclosure may be applied, it should be recognized that the illustrated embodiments are only preferred examples and should not be taken as limiting the scope of the disclosure. Rather, the scope of the disclosure is defined by the following claims.

What is claimed is:

1. A prosthetic valve, comprising:
a radially expandable and compressible frame comprising a plurality of interconnected struts, each strut having a first end, a second end, and a length extending from the first end to the second end, each strut comprising a plurality of linear segments that are laterally offset from each other in a direction perpendicular to the lengths of the struts; and
a valvular structure mounted to the frame and configured to regulate the flow of blood through the prosthetic valve.

2. The prosthetic valve of claim 1, wherein each of the plurality of struts is hingeably connected to at least another of the plurality of struts.

3. The prosthetic valve of claim 1, further comprising a spacer disposed between a pair of connected struts.

4. The prosthetic valve of claim 1, wherein the struts are connected to each other by pins extending through the struts.

5. The prosthetic valve of claim 4, wherein each pin extends through overlapping apertures of two struts, wherein each aperture of the overlapping apertures is arranged in an intermediate segment of a respective strut, each intermediate segment arranged between adjacent linear segments of the respective strut.

6. The prosthetic valve of claim 5, wherein a width of each intermediate segment is greater than a width of the adjacent linear segments, the widths arranged perpendicular to the length of the respective strut.

7. The prosthetic valve of claim 1, wherein each linear segment is defined by two longitudinal edges of the linear segment with a central longitudinal axis arranged between the two longitudinal edges, wherein the central longitudinal axes of the plurality of linear segments of each strut are laterally offset from each other, and wherein a width of each linear segment of each strut varies along the length of the strut, the width arranged perpendicular to the length of the strut.

8. The prosthetic valve of claim 1, wherein the frame comprises a plurality of circumferentially spaced locking units configured to lock the frame in a radially expanded state.

9. The prosthetic valve of claim 1, further comprising at least one linear actuator assembly coupled to the frame and configured to radially expand the frame.

10. The prosthetic valve of claim 1, further comprising an annular skirt secured to an outer surface of an inflow end portion of the plurality of interconnected struts.

11. The prosthetic valve of claim 1, wherein the first end of each strut forms a first apex arranged at a first end of the frame and a second end of each strut forms a second apex arranged at an opposite, second end of the frame and wherein a width of the first end and the second end is greater than a width of each linear segment of the plurality of linear segments of each strut, the widths arranged perpendicular to the length of the strut.

12. A prosthetic valve, comprising:
a radially expandable and compressible annular frame comprising a plurality of interconnected struts, each strut having a first end portion arranged at an inflow end of the frame, a second end portion arranged at an outflow end of the frame, and a length extending from the first end to the second end, each strut comprising a plurality of linear segments that are laterally offset from each other in a direction perpendicular to the length of the strut and that are arranged end-to-end with adjacent ends interconnected to each other by intermediate segments of the strut; and
a valvular structure coupled to the frame and configured to regulate the flow of blood through the prosthetic valve.

13. The prosthetic valve of claim 12, wherein each intermediate segment and each of the first end portion and second end portion of each strut includes a respective aperture adapted to receive a fastener, wherein each linear segment has a first width, and wherein each intermediate segment and each of the first end portion and the second end portion of each strut has a second width that is wider than the first width, the first width and second width arranged perpendicular to the length of the strut.

14. The prosthetic valve of claim 13, wherein the plurality of struts are interconnected at a plurality of hinge joints and wherein each hinge joint of the plurality of hinge joints is formed by a fastener extending through apertures of overlapping intermediate segments of a pair of struts of the plurality of struts so that the pair of struts are hingeably connected to one another.

15. The prosthetic valve of claim 14, wherein a spacer is disposed between the overlapping intermediate segments of the pair of struts.

16. The prosthetic valve of claim 12, wherein the frame comprises a plurality of circumferentially spaced locking units configured to lock the frame in a radially expanded state and wherein each locking unit is secured to the frame via a fastener extending through an aperture formed in the locking unit and through corresponding apertures in corresponding, overlapping intermediate segments of struts of the plurality of interconnected struts.

17. A prosthetic valve, comprising:
an annular frame, radially expandable and compressible between a radially expanded state and a radially compressed state, the frame comprising a plurality of interconnected struts, each strut having a zig-zag pattern defined by a plurality of offset linear segments that have central longitudinal axes that are offset from one another in a direction perpendicular to a length of each strut, the central longitudinal axis of each linear segment defined between two longitudinal edges of the linear segment, the length of each strut defined between a first end portion that forms a portion of an apex at a first end of the frame and a second end portion that forms a portion of an apex at an opposite, second end of the frame, each linear segment of each strut arranged between one of the first end portion and the second end portion and an intermediate segment or between two adjacent intermediate segments; and
a valvular structure mounted to the frame and comprising a leaflet assembly.

18. The prosthetic valve of claim 17, wherein the plurality of interconnected struts are hingeably coupled to each other at hinge joints formed by pins extending through overlapping apertures in the struts, the overlapping apertures arranged in overlapping intermediate segments.

19. The prosthetic valve of claim 18, wherein a plurality of open cells are defined between the plurality of interconnected struts and wherein when the frame is in the radially compressed state, a gap is formed at a middle of each open cell, between two adjacent hinge joints.

20. The prosthetic valve of claim 17, wherein a width of each linear segment of a strut of the plurality of struts varies along the length of the strut, the width arranged perpendicular to the length of the strut.

* * * * *